United States Patent [19]
Haseba et al.

[11] Patent Number: 5,858,272
[45] Date of Patent: Jan. 12, 1999

[54] PHENYLDIOXANE DERIVATIVES, LIQUID CRYSTAL COMPOSITIONS, AND LIQUID CRYSTAL DISPLAY ELEMENTS

[75] Inventors: Yasuhiro Haseba; Shuichi Matsui; Kazutoshi Miyazawa; Hiroyuki Takeuchi; Yasusuke Hisatsune; Fusayuki Takeshita; Etsuo Nakagawa, all of Chiba, Japan

[73] Assignee: Chisso Corporation, Osaka-fu, Japan

[21] Appl. No.: 893,237

[22] Filed: Jul. 15, 1997

[30] Foreign Application Priority Data

Jul. 15, 1996 [JP] Japan ................................... 8-205188
May 22, 1997 [JP] Japan ................................... 9-148659

[51] Int. Cl.$^6$ ................................................. C09K 19/34
[52] U.S. Cl. .................................. 252/299.61; 252/299.01
[58] Field of Search .......................... 252/299.61, 299.01

[56] References Cited

U.S. PATENT DOCUMENTS 5,683,623  11/1997  Chan et al. ........................ 252/299.61

*Primary Examiner*—Shean C. Wu
*Attorney, Agent, or Firm*—Wenderoth, Lind & Ponack, L.L.P.

[57] ABSTRACT

There is provided an electrically and chemically stable liquid crystalline compound which exhibits a significantly large value of De and a high voltage holding ratio. The compound is a phenyldioxane derivative represented by formula (1):

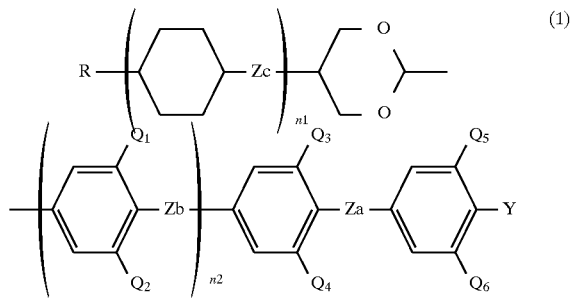

wherein R represents a C1–C20 alkyl group; each of n1 and n2 represents 0 or 1; each of $Q_1$ through $Q_6$ represents a hydrogen atom, a fluorine atom, or a chlorine atom, provided that $Q_3$ is a fluorine atom or a chlorine atom when n2 is 0, and that at least one of $Q_1$ and $Q_3$ is a fluorine atom or a chlorine atom when n2 is 1; each of Za and Zb represents a single bond, —COO—, or —CF$_2$O—; Zc represents a single bond or —CH$_2$CH$_2$—; Y represents a hydrogen atom, a halogen atom, or a C1–C5 halogenated alkyl group in which one or more non-adjacent methylene groups may be replaced by oxygen atoms or sulfur atoms; and each of the elements that constitute the compound may comprise isotopes of the element. The compound also exhibits excellent compatibility with previously known liquid crystalline compounds, and is advantageously used for low voltage driving of liquid crystal displays for TFTs. There are also provided liquid crystal compositions comprising the compound, as well as liquid crystal display elements constructed of the compositions.

30 Claims, No Drawings

PHENYLDIOXANE DERIVATIVES, LIQUID CRYSTAL COMPOSITIONS, AND LIQUID CRYSTAL DISPLAY ELEMENTS

BACKGROUND OF THE INVENTION

1. Field of the Invention

The present invention relates to liquid crystalline compounds and liquid crystal compositions. More particularly, the invention relates to phenyldioxane derivatives, which are liquid crystalline compounds suitable for use as components of liquid crystal compositions, inter alia liquid crystal compositions for TFT (thin film transistor) liquid crystal display elements, as well as to liquid crystal compositions containing the compounds, and to liquid crystal display elements formed through use of the liquid crystal compositions.

2. Description of the Related Art

Liquid crystal display elements utilize the optical anisotropy and the dielectric anisotropy of liquid crystal substances. Based on their display modes, liquid crystal display elements are classified into various types such as TN (twisted nematic) mode, DS (dynamic scattering) mode, guest-host mode, DAP (deformation of vertical aligned phases) mode, and STN (super-twisted nematic) mode. Liquid crystal materials suitable for these types of liquid crystal display elements have different characteristics. Recently, liquid crystal display elements are required to have improved display quality, resulting in increased demand for active-matrix-mode display elements such as a TFT (thin film transistor) liquid crystal display element.

Liquid crystal materials used for these display elements must be stable against moisture, air, heat, light, etc. Further, they must exhibit liquid crystal phases within as broad a temperature range as possible, around room temperature; must have a low viscosity, good compatibility, a large dielectric anisotropy value ($\Delta\epsilon$), and an optimal birefringence value ($\Delta n$); and must exhibit a high voltage holding ratio. Especially, liquid crystal materials used for TFT liquid crystal display elements must have a high voltage holding ratio. However, at the present, no single compound satisfies all of the above-mentioned requirements. Therefore, liquid crystal compositions that are obtained by mixing several kinds of liquid crystalline and non-liquid crystalline compounds are currently used.

Recently, there has arisen a demand to drive TFT liquid crystal display elements at low voltage. This in turn demands liquid crystalline compounds and liquid crystal compositions which have a higher $\Delta\epsilon$ as compared to conventional liquid crystal materials (hereinafter, the term "liquid crystalline compounds" is used as a term which encompasses compounds having liquid crystal phases and compounds that have liquid crystal phases even when mixed with other liquid crystals). Therefore, active efforts have been carried out to develop a liquid crystal material having a large $\Delta\epsilon$ while maintaining a high voltage holding ratio. Conventionally, as a liquid crystal material exhibiting a high voltage holding ratio, a fluorine-containing compound such as a compound expressed by the following formula (10) is generally known (Japanese Patent Publication (kokoku) No. 1-04496).

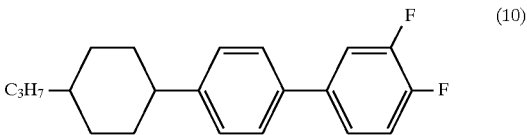

The compound of formula (10) has a higher specific resistance than do liquid crystalline compounds having a cyano group, and thus, it is mainly used for a component of liquid crystal compositions for TFT liquid crystal display elements. However, since the extrapolated $\Delta\epsilon$ of the compound is as small as 8.7, the compound cannot be used as a liquid crystal material for low voltage drive, such as 2.5 V drive, which is currently demanded.

The above-mentioned extrapolated $\Delta\epsilon$ is a value calculated from the $\Delta\epsilon$ of a composition containing a base liquid-crystal having a nematic phase and the formula (10) compound dissolved therein, the $\Delta\epsilon$ of the base liquid crystal, and the mixture ratio of the compound with respect to the composition. The extrapolated $\Delta\epsilon$ substantially reflects the $\Delta\epsilon$ of the formula (10) compound (in the following descriptions, $\Delta\epsilon$ used in relation to compounds has the same meaning).

As a liquid crystal material having a $\Delta\epsilon$ larger than that of the above-mentioned compound of formula (10), a trifluorophenyl derivative expressed by the following formula (11) is known (Japanese Patent Application Laid-Open (kokai) No. 2-233626).

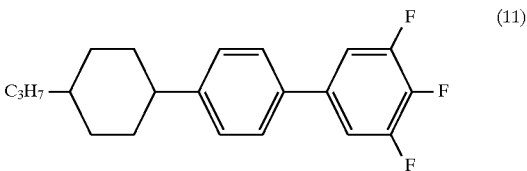

The $\Delta\epsilon$ of the formula (11) compound is 11.7, which is greater than the $\Delta\epsilon$ of the formula (10) compound. However, this compound also cannot satisfy the market needs for low voltage drive, for the same reason as described above.

Moreover, a trifluoromethylphenyl derivative expressed by the following formula (12) and a trifluoromethoxyphenyl derivative expressed by the following formula (13) are known (Japanese Patent Application Laid-Open No. (kokai) No. 4-506361).

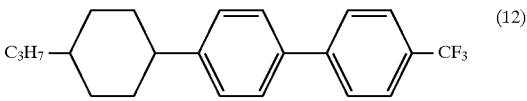

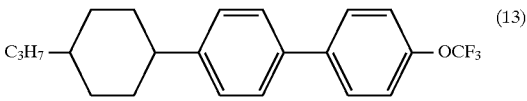

Since the $\Delta\epsilon$s of these compounds are not sufficiently large (for example, the $\Delta\epsilon$ of the formula (13) compound is 8.7 (IDY (The Institute of Television Engineers of Japan Techninal Report) 95), these compounds cannot satisfy the market needs for low voltage drive, for the same reason as described above.

There is also known a tricyclic compound expressed by the following formula (14) which corresponds to the above-mentioned formula (13) compound but having two fluorine atoms substituted at lateral positions of the central benzene ring (IDY (The Institute of Television Engineers of Japan Techninal Report) 95).

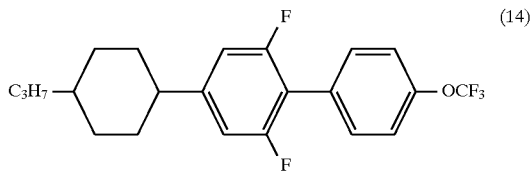

The $\Delta\epsilon$ of the formula (14) compound is 13.0, which is 4.3 greater than the $\Delta\epsilon$ of the formula (13) compound. However, this compound also cannot satisfy the market needs for low voltage drive, for the same reason as described above.

Also, a dioxane derivative expressed by the following formula (15) is known as a compound having a large $\Delta\epsilon$ (Japanese Patent Application Laid-Open No. (kokai) No. 2-233626).

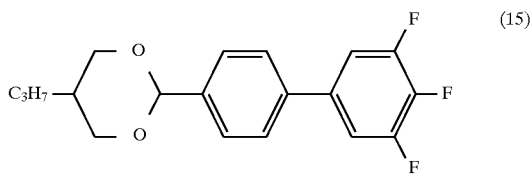

The $\Delta\epsilon$ of the formula (15) compound is as large as about 15. However, the $\Delta\epsilon$ of this compound is not sufficiently large to lower the drive voltage of TFT liquid crystal display elements to a required level. Also, since the voltage holding ratio of the compound at 100° C. is as low as 89%, the mixture ratio of the compound cannot be increased for the preparation of a liquid crystal composition for TFT liquid crystal display elements. Accordingly, there have been strong demand for a compound that can solve the above-described problems.

Lastly, a dioxane derivative expressed by the following formula (16) which resembles the compound (15) is also known. However, the $\Delta\epsilon$ of this compound has been found to be as small as 9.0 (Japanese Patent Publication (kokoku) No. 64-2114).

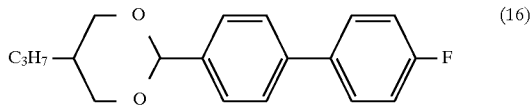

SUMMARY OF THE INVENTION

In view of the foregoing, an object of the present invention is to provide a liquid crystalline compound which has a considerably large $\Delta\epsilon$ and a high voltage holding ratio, which is stable electrically and chemically, which has a good compatibility with currently existing liquid crystalline compounds, and which is particularly suitable for TFT liquid crystal display elements that are driven at low voltage.

Another object of the present invention is to provide a liquid crystalline composition that contains the above liquid crystal compound.

Still another object of the present invention is to provide a liquid crystal display element formed through use of the above liquid crystal composition.

In an attempt to attain the above objects, the present inventors have carried out extensive studies and have found that a phenyldioxane derivative whose molecular structure includes a 1,3-dioxane-2,5-diyl group, and a 1,4-phenylene group in which a fluorine atom or a chlorine atom has substituted is a liquid crystalline compound which exhibits a significantly high value of $\Delta\epsilon$ and a high voltage holding ratio. Moreover, this compound has good compatibility with conventionally known liquid crystalline compounds, and is best suited as TFT liquid crystal materials for low voltage drive typified by 2.5 V drive. The invention has been accomplished based on this finding.

Accordingly, the present invention provides a phenyldioxane derivative expressed by the following formula (1):

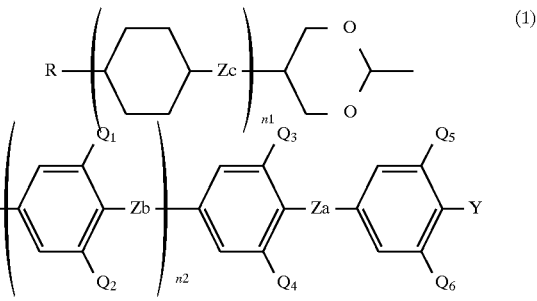

wherein R represents a C1–C20 alkyl group; each of n1 and n2 represents 0 or 1; each of $Q_1$ through $Q_6$ represents a hydrogen atom, a fluorine atom, or a chlorine atom, provided that $Q_3$ is a fluorine atom or a chlorine atom when n2 is 0, and that at least one of $Q_1$ and $Q_3$ is a fluorine atom or a chlorine atom when n2 is 1; each of Za and Zb represents a single bond, —COO—, or —CF$_2$O—; Zc represents a single bond or —CH$_2$CH$_2$—; Y represents a hydrogen atom, a halogen atom, or a C1–C5 halogenated alkyl group in which one or more non-adjacent methylene groups may be replaced by oxygen atoms or sulfur atoms; and each of the elements that constitute the compound may comprise isotopes of the element.

The present invention specifically provides a phenyldioxane derivative of formula (1) in which n1 and n2 are both 0, a phenyldioxane derivative of formula (1) in which n1 is 0 and n2 is 1, and a phenyldioxane derivative of formula (1) in which n1 is 1 and n2 is 0.

More specifically, the present invention provides a phenyldioxane derivative of formula (1) in which n1 and n2 are both 0 and $Q_3$ and $Q_4$ are both fluorine atoms, and a phenyldioxane derivative of formula (1) in which n1 and n2 are both 0, $Q_3$ is a fluorine atom, and $Q_4$ is a hydrogen atom.

The present invention also provides a liquid crystal composition comprising at least one species of phenyldioxane derivative as described above.

The present invention specifically provides a liquid crystal composition comprising a first component and a second component, the first component being at least one species of phenyldioxane derivative as described above, and the second component being at least one compound selected from the group consisting of formula (2) compounds, formula (3) compounds, and formula (4) compounds:

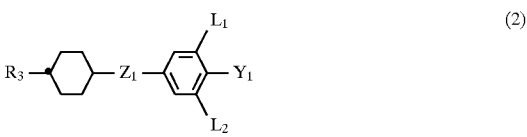

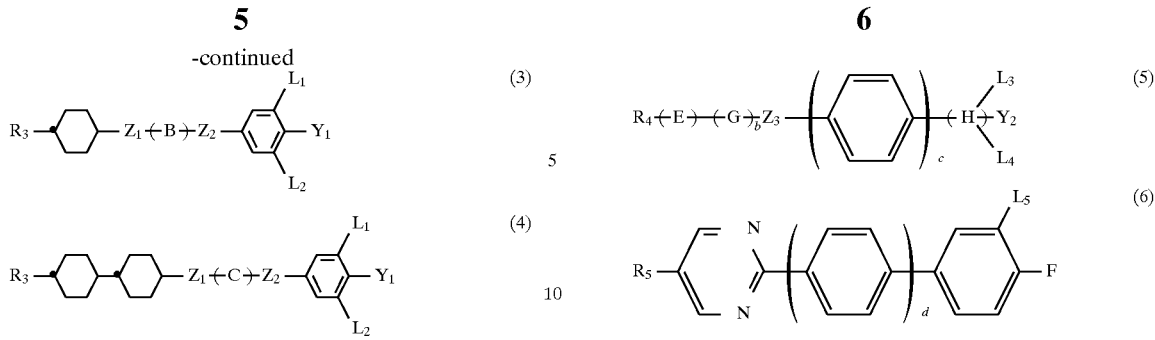

wherein $R_3$'s, $Y_1$'s, $L_1$'s, $L_2$'s, $Z_1$'s, and $Z_2$'s appearing in these formulas may respectively represent the same atom/group or different atoms/groups, $R_3$ represents a C1–C10 alkyl group in which one or more non-adjacent methylene groups may be replaced by oxygen atoms or —CH=CH— groups and hydrogen atoms may arbitrarily be substituted by fluorine atoms; $Y_1$ represents a fluorine atom, a chlorine atom, $OCF_3$, $OCF_2H$, $CF_3$, $CF_2H$, $CFH_2$, $OCF_2CF_2H$, or $OCF_2CFHCF_3$; each of $L_1$ and $L_2$ represents a hydrogen atom or a fluorine atom; each of $Z_1$ and $Z_2$ represents a 1,2-ethylene group, a 1,4-butylene group, —COO—, —$CF_2O$—, —$OCF_2$—, —CH=CH—, or a single bond; ring B represents trans-1,4-cyclohexylene, 1,3-dioxane-2,5-diyl, or 1,4-phenylene in which a hydrogen atom may be substituted by a fluorine atom; ring C represents trans-1,4-cyclohexylene or 1,4-phenylene in which a hydrogen atom may be substituted by a fluorine atom; and each of the elements that constitute the respective compounds of formulas (2), (3), and (4) may comprise isotopes of the element.

This composition may optionally contain as the third component at least one compound selected from the group consisting of formula (7) compounds, formula (8) compounds, and formula (9) compounds:

 (7)

 (8)

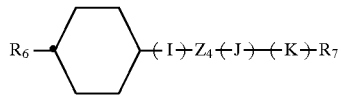 (9)

wherein $R_6$'s, $R_7$'s, I's, J's, and K's appearing in these formulas may respectively represent the same atom/group or different atoms/groups, each of $R_6$ and $R_7$ represents a C1–C10 alkyl group in which one or more non-adjacent methylene groups may be replaced by oxygen atoms or —CH=CH— groups and hydrogen atoms may arbitrarily be substituted by fluorine atoms; each of I, J, and K represents trans-1,4-cyclohexylene, pyrimidine-2,5-diyl, or 1,4-phenylene in which a hydrogen atom may be substituted by a fluorine atom; each of $Z_4$ and $Z_5$ represents —C≡C—, —COO—, —$CH_2CH_2$—, —CH=CH—, or a single bond; and each of the elements that constitute the respective compounds of formulas (7), (8), and (9) may comprise isotopes of the element.

The present invention specifically provides another liquid crystal composition comprising a first component and a second component, the first component being at least one species of phenyldioxane derivative as described above, and the second component being at least one compound selected from the group consisting of formula (5) compounds and formula (6) compounds:

wherein each of $R_4$ and $R_5$ represents a C1–C10 alkyl group in which one or more non-adjacent methylene groups may be replaced by oxygen atoms or —CH=CH— groups, and hydrogen atoms may arbitrarily be substituted by fluorine atoms; $Y_2$ represents —CN or —C≡C—CN; ring E represents trans-1,4-cyclohexylene, 1,4-phenylene, 1,3-dioxane-2,5-diyl, or pyrimidine-2,5-diyl; ring G represents trans-1,4-cyclo-hexylene, 1,4-phenylene in which hydrogen atoms may be substituted by fluorine atoms, or pyrimidine-2,5-diyl; ring H represents trans-1,4-cyclohexylene or 1,4-phenylene; $Z_3$ represents a 1,2-ethylene group, —COO—, or a single bond; each of $L_3$, $L_4$, and $L_5$ represents a hydrogen atom or a fluorine atom; each of b, c, and d represents 0 or 1; and each of the elements that constitute the respective compounds of formulas (5) and (6) may comprise isotopes of the element.

This composition may optionally contain as the third component at least one compound selected from the group consisting of the aforementioned formula (7) compounds, formula (8) compounds, and formula (9) compounds.

The present invention further provides a liquid crystal composition comprising first, second, and third components, the first component comprising at least one species of phenyldioxane derivative as described above; part of the second component comprising at least one compound selected from the group consisting of the aforementioned formula (2) compounds, formula (3) compounds, and formula (4) compounds and the remaining part of the second component comprising at least one compound selected from the group consisting of the aforementioned formula (5) and formula (6) compounds; and the third component comprising at least one compound selected from the group consisting of the aforementioned formula (7) compounds, formula (8) compounds, and formula (9) compounds.

The liquid crystal compositions of the present invention may further contain an optically active compound.

The present invention also provides a liquid crystal display element comprising of any one of the liquid crystal compositions described above.

DESCRIPTION OF PREFERRED EMBODIMENTS

The liquid crystalline compound of the present invention, i.e., a phenyldioxane derivative of formula (1), has tri- to penta-cyclic cores including a dioxane ring, and a fluorine atom or a chlorine atom is substituted at a lateral position of a 1,4-phenylene group in the inner core(s). This structure realizes a considerably high value of Δε and good compatibility with previously known liquid crystalline compounds. Moreover, surprisingly enough, the voltage holding ratio of the compound has been found to be higher than that of a phenyldioxane derivative represented by formula (15) in which neither a fluorine atom nor a chlorine atom has substituted at lateral positions.

The above-mentioned advantages are first attained by the specific molecular structure of the liquid crystalline compound of the present invention, which includes a dioxane ring, and a 1,4-phenylene group having a fluorine atom substituted at a lateral position.

The liquid crystalline compounds of formula (1) of the present invention, being highly compatible with previously known liquid crystalline compounds and having high voltage holding ratios, can be incorporated in large amounts into a liquid crystal composition.

These features, in conjunction with high $\Delta\epsilon$ values, enable the compounds of the present invention to provide liquid crystal compositions which are useful for reducing voltage for driving TFT liquid crystal display elements.

In formula (1), R represents an alkyl group having 1 to 20 carbon atoms (C1–C20 alkyl). From the viewpoints of balancing the viscosity and clearing point of the compound, R is preferably a C1–C7 alkyl group and more preferably a C2–C5 alkyl group.

Each of the linking groups Za and Zb represents a single bond, —COO— or —CF$_2$O—. Of these, the single bond provides compounds which have relatively high clearing points, relatively low viscosity, and excellent compatibility with other liquid crystalline compounds or liquid crystal compositions and which are chemically and electrically stable; the group —COO— provides compounds having high clearing points and high values of $\Delta\epsilon$; and the group —CF$_2$O— provides chemically and electrically stable compounds having low viscosity and relatively high values of $\Delta\epsilon$.

The linking group Zc represents a single bond or a group —CH$_2$CH$_2$—. The former provides compounds having high clearing points and the latter provides compounds having good compatibility.

Each of n1 and n2 is 0 or 1. Specifically, there are cases in which n1 and n2 are both 0, those in which n1 is 0 and n2 is 1, and those in which n1 is 1 and n2 is 0. Compounds of the following formulas (1-a), (1-b), and (1-c) respectively correspond to these cases.

of $\Delta$n and high values of $\Delta\epsilon$; and compounds represented by formula (1-c) exhibit high clearing points and lower viscosity than do compounds of formula (1-b).

The terminal substituent Y represents a hydrogen atom, a halogen atom, or a C1–C5 halogenated alkyl group in which one or more non-adjacent methylene groups may be substituted by oxygen atoms or sulfur atoms.

When the halogen atom is F, there are obtained compounds having relatively high values of $\Delta\epsilon$, low viscosity, and good compatibility with other liquid crystalline compounds or liquid crystal compositions. In contrast, when the halogenated alkyl group is CF$_3$, the resulting compounds have considerably high values of $\Delta\epsilon$, and when it is OCF$_3$, the resulting compounds have low viscosity.

When the halogen atom is Cl, or when the halogenated alkyl group in which one or more non-adjacent methylene groups may be substituted by oxygen atom(s) is OCF$_2$CF$_2$H or OCF$_2$CFHCF$_3$, the resulting compounds have high values of $\Delta$n and high clearing points.

Preferred examples of halogenated alkyl groups in which one or more non-adjacent methylene groups may or may not be substituted by oxygen atom(s) include a difluoromethyl group, a difluorochloromethyl group, a 2,2,2-trifluoroethyl group, a 2-fluoroethyl group, a 3-fluoropropyl group, a 4-fluorobutyl group, a difluoromethoxy group, a difluorochloromethoxy group, a pentafluoroethoxy group, and a heptafluoropropoxy group.

Each of the lateral substituents Q$_1$ through Q$_6$ represents a hydrogen atom, a fluorine atom, or a chlorine atom. When n2 is 0, Q$_3$ is preferably a fluorine atom or a chlorine atom; and when n2 is 1, preferably at least one of Q$_1$ and Q$_3$ is a fluorine atom or a chlorine atom. In Q$_1$ through Q$_6$, as hydrogen atoms approach dominance, compounds exhibiting higher liquid crystal phase temperature ranges and lower viscosity are obtained, and as fluorine atoms approach dominance, compounds exhibiting higher values of $\Delta\epsilon$ are obtained.

As described above, the molecular structure of the compound of the present invention includes a dioxane ring, and

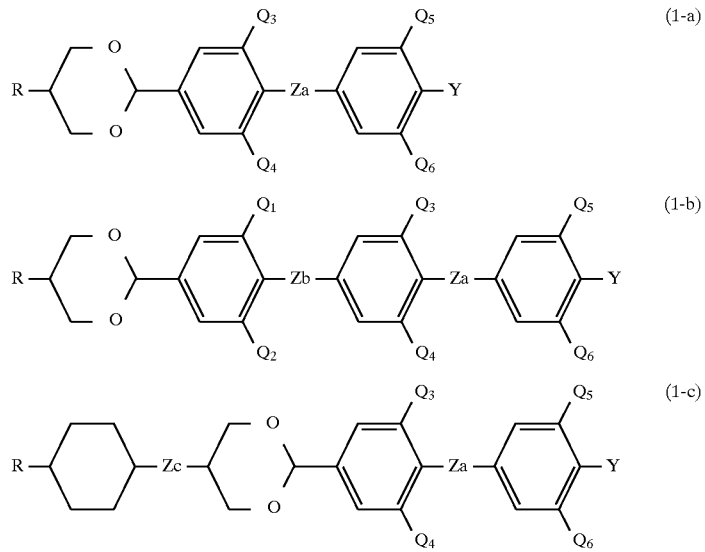

Of the above-described compounds, compounds represented by formula (1-a) exhibit low viscosity and good compatibility with other liquid crystalline compounds or liquid crystal compositions and have high values of $\Delta\epsilon$; compounds represented by formula (1-b) have high values a fluorine- or chlorine-substituted 1,4-phenylene group. When a fluorine atom or a chlorine atom is substituted at a lateral position of the 1,4-phenylene group located adjacent to the dioxane ring, the resulting compound is particularly preferred, as it exhibits a significantly high value of $\Delta\epsilon$.

Of substituted 1,4-phenylene groups, a 3-fluoro-1,4-phenylene group provide compounds exhibiting relatively high values of Δε, high liquid crystal phase temperature ranges, low viscosity, and good compatibility; and a 3,5-difluorophenylene group provides compounds having significantly high values of Δε and very good compatibility. In the compounds of the present invention, the elements that constitute the compounds may comprise isotopes of the elements.

The compounds of the present invention are particularly suitable as components of liquid crystal compositions for TFTs. The compounds are also advantageously used as components of liquid crystal compositions for other uses such as TN-mode display elements, guest-host-mode display elements, polymer-distribution-type liquid crystal display elements, dynamic scattering mode display elements, STN-mode display elements, inplane switching elements, OCB (optically compensated birefringence) mode elements, and R-OCB mode elements. Moreover, the compounds are useful for forming ferroelectric liquid crystals and antiferroelectric liquid crystals.

The liquid crystal composition of the present invention comprises at least one liquid crystalline compound of formula (1) as a first component.

The amount of the first component must be between 0.1 and 99.9% by weight with respect to the weight of the liquid crystal composition in order to obtain excellent characteristics. The amount is preferably between 1 and 50% by weight, and more preferably between 3 and 20% by weight.

Although the liquid crystal composition of the present invention may consist only of the aforementioned first component, preferably the composition contains, in addition to the first component (i.e., a liquid crystalline compound of formula (1)), a second component and further optionally a third component; the second component being a mixture of at least one compound selected from the group consisting of the compounds of above-described formulas (2), (3), and (4) (this compound is referred to as the second-A component) and/or at least one compound selected from the group consisting of the compounds of above-described formulas (5) and (6) (this compound is referred to as the second-B component); and the third component being at least one compound selected from the group consisting of the compounds of above-described formulas (7), (8), and (9). Moreover, optically active compounds and other known compounds may also be incorporated in order to adjust the threshold voltage, liquid crystal phase temperature range, Δε, Δn, viscosity, etc.

Of the aforementioned second-A components, examples of the compounds of formula (2) include the following formula (2-1) through (2-9) compounds, examples of the compounds of formula (3) include the following formula (3-1) through (3-69) compounds, and examples of the compounds of formula (4) include the following formula (4-1) through (4-24) compounds:

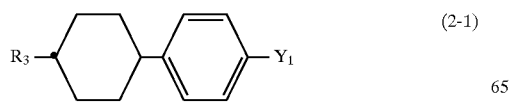
(2-1)

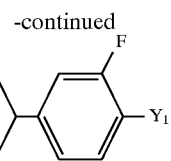
(2-2)

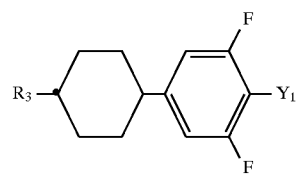
(2-3)

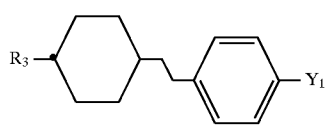
(2-4)

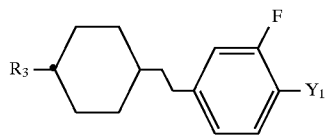
(2-5)

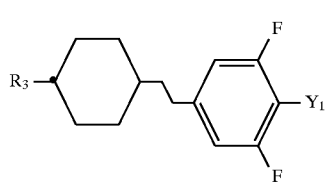
(2-6)

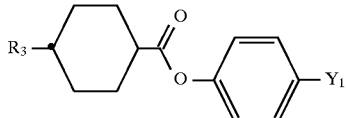
(2-7)

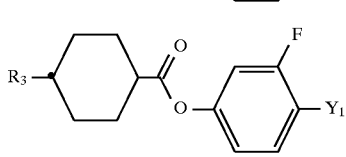
(2-8)

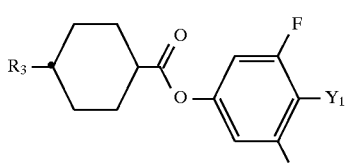
(2-9)

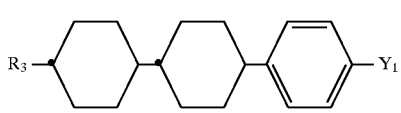
(3-1)

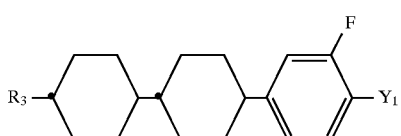
(3-2)

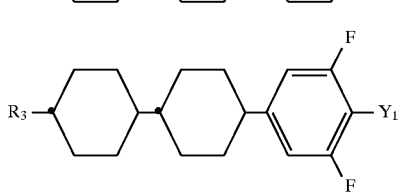
(3-3)

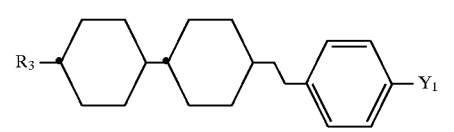 (3-4)
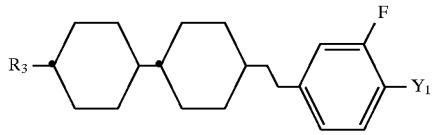 (3-5)
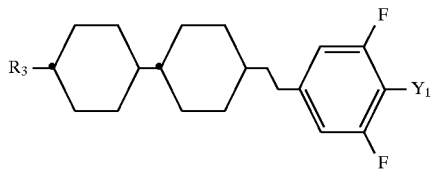 (3-6)
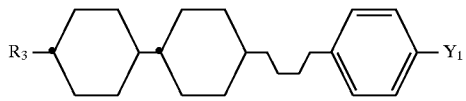 (3-7)
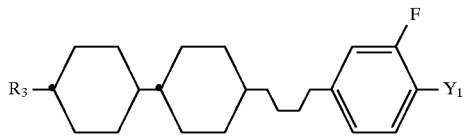 (3-8)
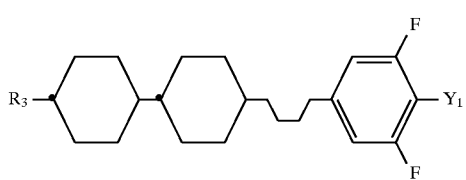 (3-9)
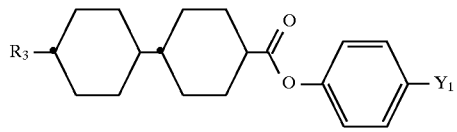 (3-10)
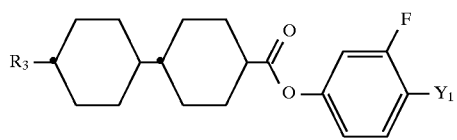 (3-11)
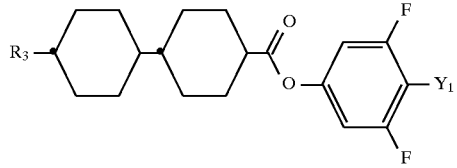 (3-12)
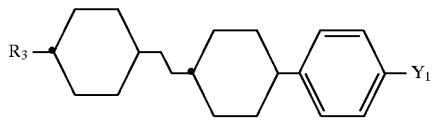 (3-13)
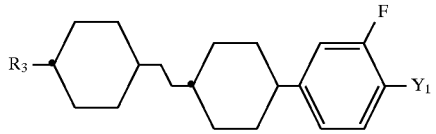 (3-14)
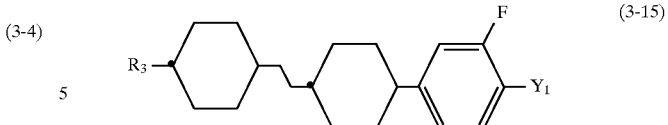 (3-15)
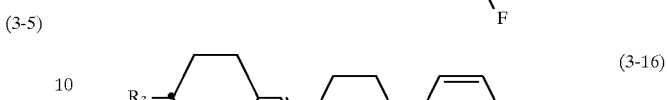 (3-16)
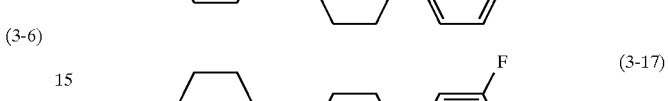 (3-17)
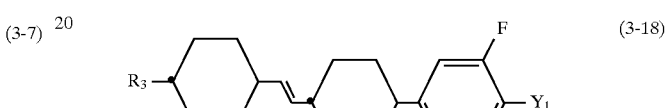 (3-18)
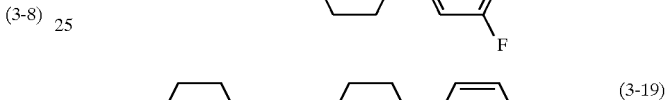 (3-19)
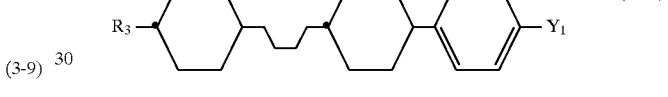 (3-20)
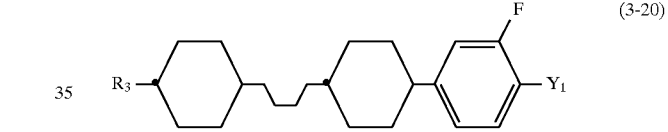 (3-21)
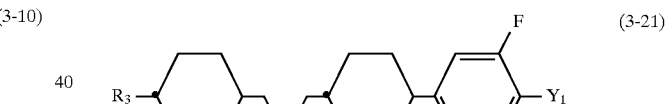 (3-22)
 (3-23)
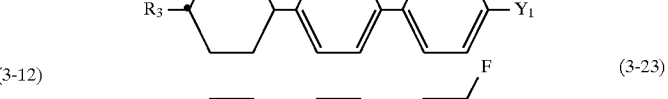 (3-24)
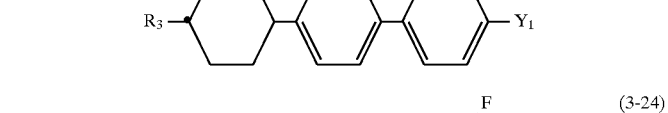 (3-25)

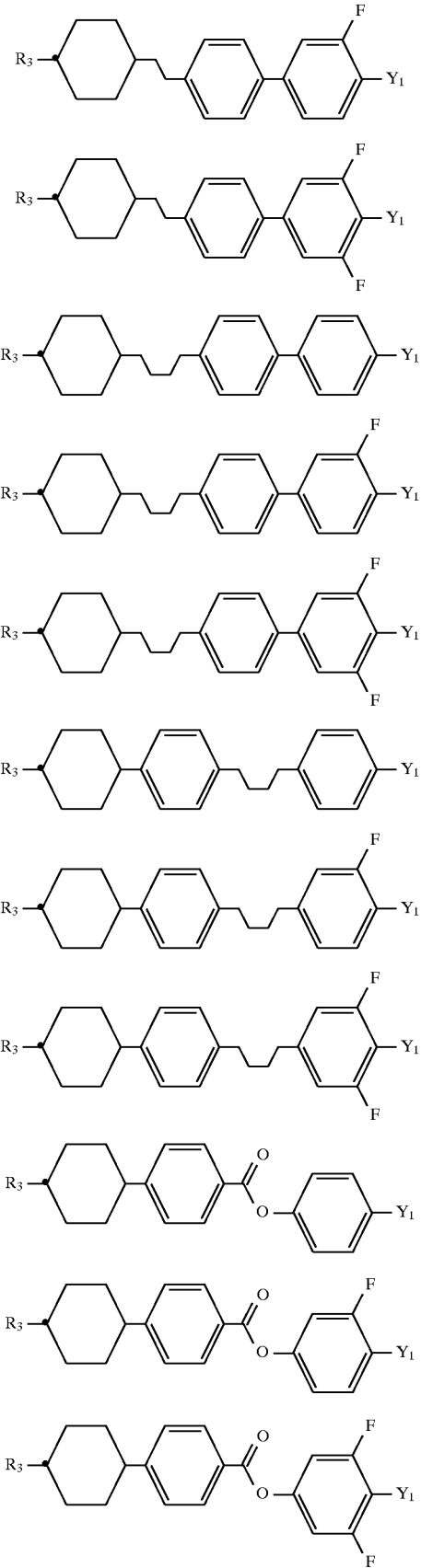
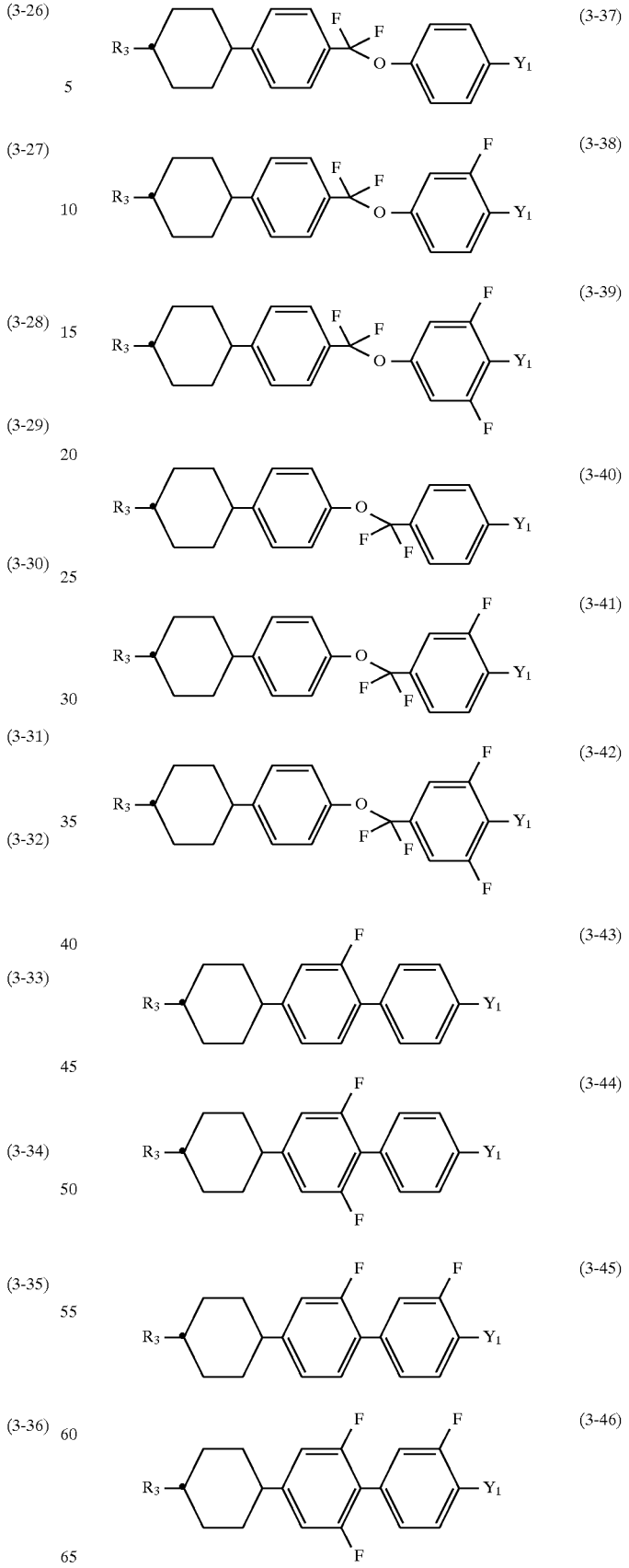

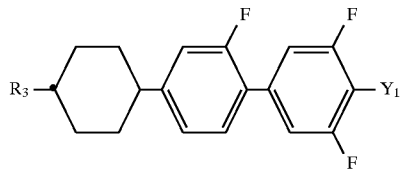 (3-47)
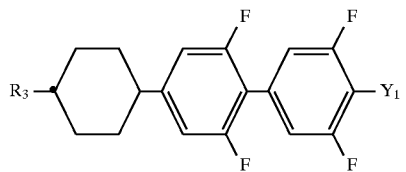 (3-48)
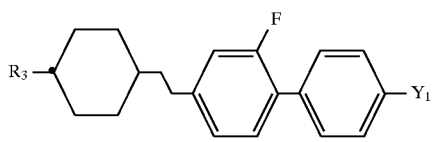 (3-49)
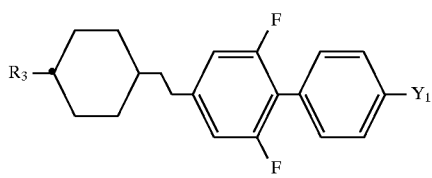 (3-50)
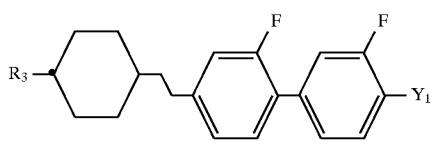 (3-51)
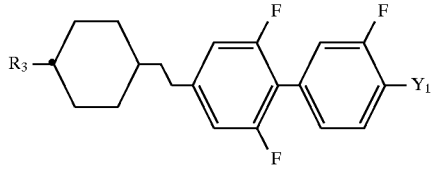 (3-52)
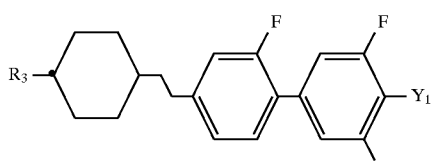 (3-53)
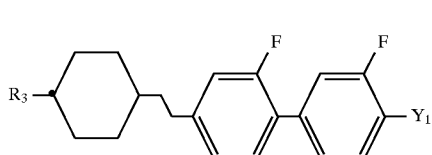 (3-54)
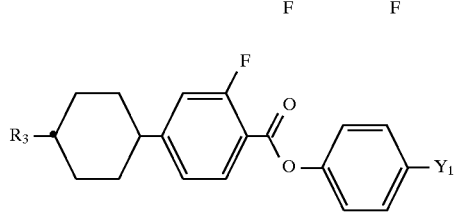 (3-55)
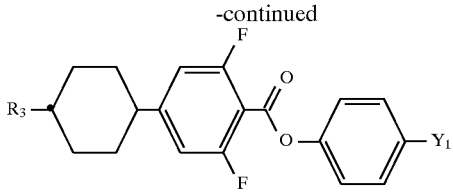 (3-56)
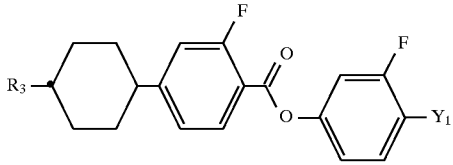 (3-57)
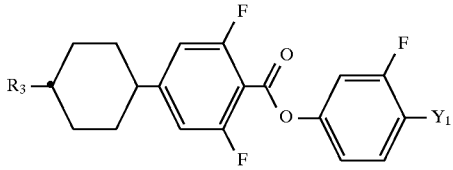 (3-58)
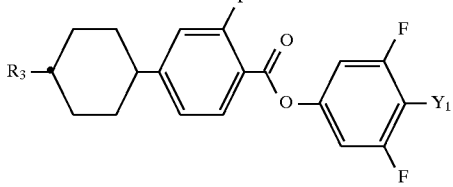 (3-59)
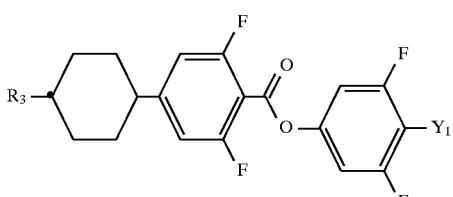 (3-60)
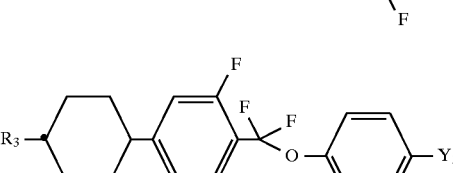 (3-61)
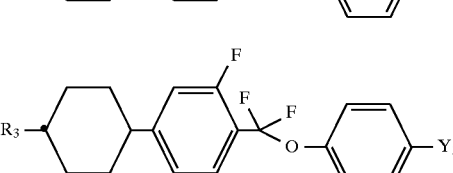 (3-62)
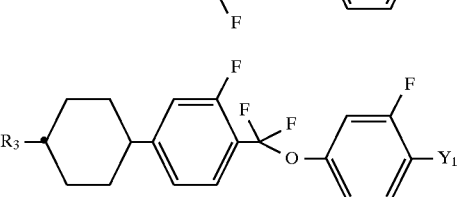 (3-63)
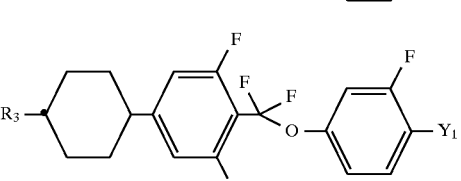 (3-64)
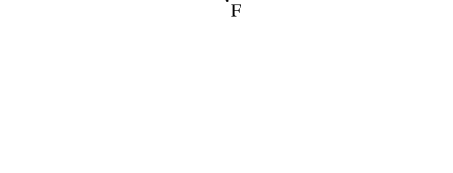

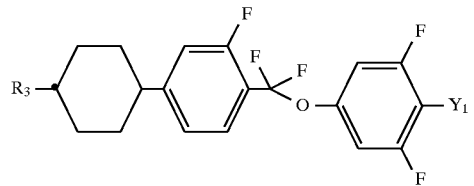
(3-65)
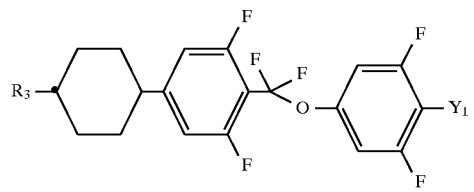
(3-66)
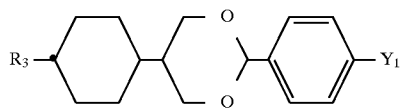
(3-67)
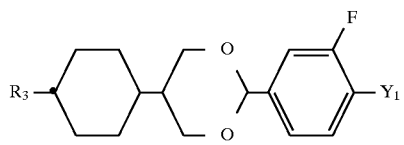
(3-68)
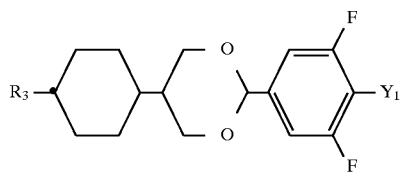
(3-69)
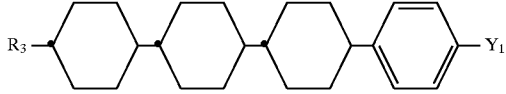
(4-1)
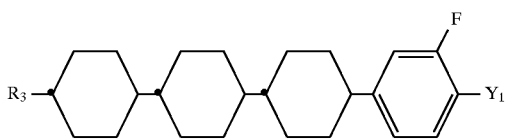
(4-2)
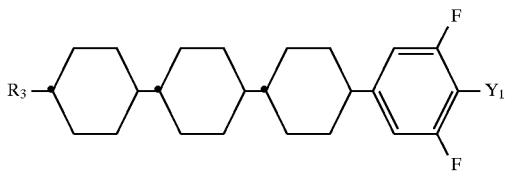
(4-3)
(4-4)
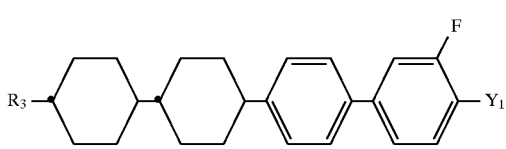
(4-5)
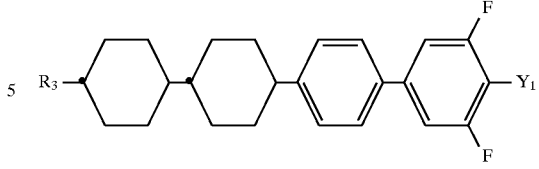
(4-6)
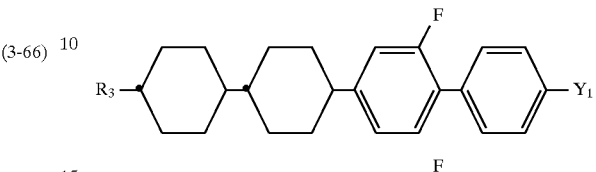
(4-7)
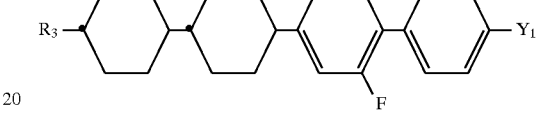
(4-8)
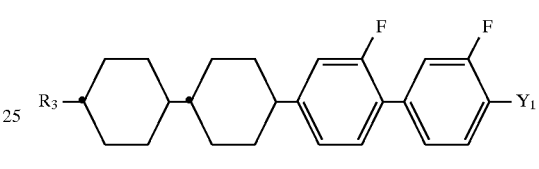
(4-9)
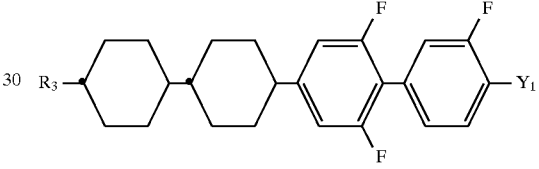
(4-10)
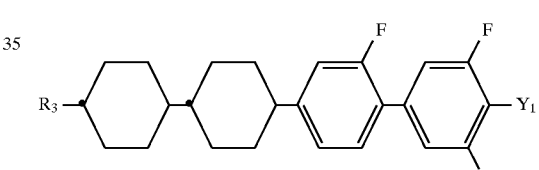
(4-11)
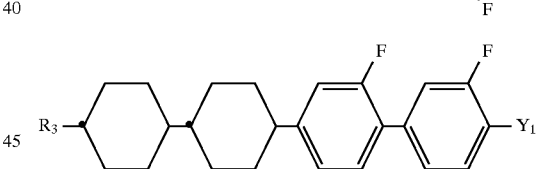
(4-12)
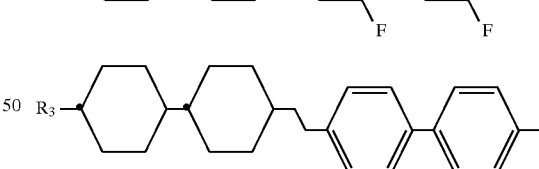
(4-13)
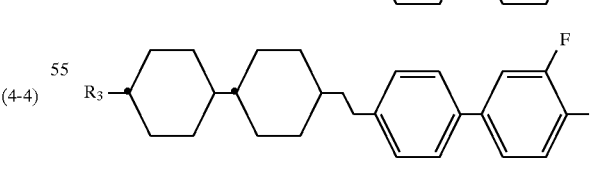
(4-14)
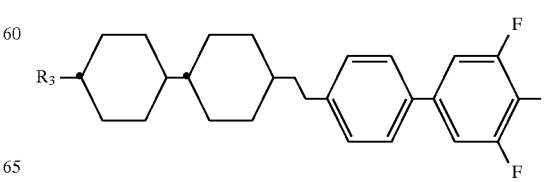
(4-15)

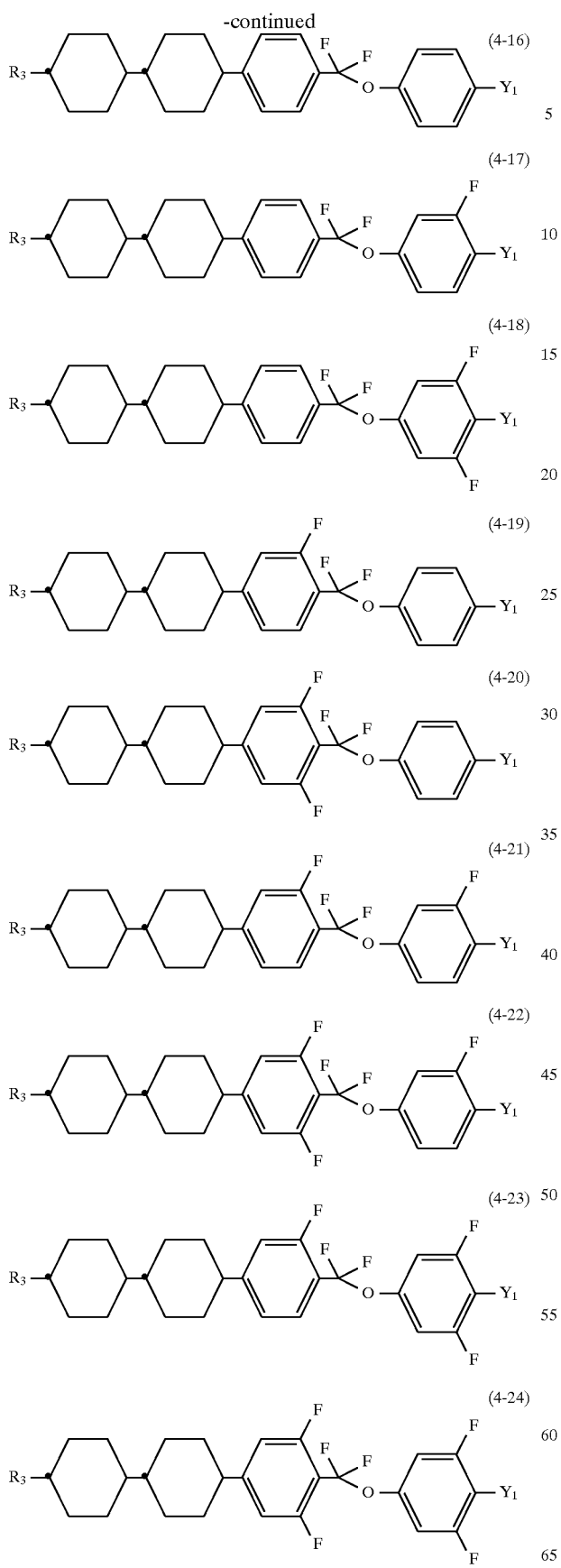

wherein $R_3$ and $Y_1$ have the same meanings as described above, and each of the elements that constitute the respective compounds may comprise isotopes of the element.

These compounds broadly expressed by formulas (2) through (4) are indispensable for preparing liquid crystal compositions for TFTs which require high levels of reliability as indicated by positive values of $\Delta\epsilon$, excellent thermal and chemical stability, and high voltage holding ratios (high specific resistance).

When liquid crystalline compositions for TFTs are prepared, the compounds of formulas (2) through (4) are incorporated in amounts of 1–99% by weight, preferably 10–97% by weight, and more preferably 40–95% by weight, based on the total weight of the liquid crystalline composition. Upon preparation, compounds of formulas (7) through (9) may also be incorporated.

The compounds of formulas (2) through (4) may also be used for preparing liquid crystal compositions suitable for STN-mode or TN-mode display elements. However, because these compounds do not exert notable effect of reducing the threshold voltage of liquid crystal compositions, the compounds are preferably used in amounts of not more than 50% by weight with respect to the total weight of the liquid crystal composition.

Next, of the aforementioned second-B components, examples of the compounds of formula (5) include the following formula (5-1) through (5-40) compounds, and examples of the compounds of formula (6) include the following formula (6-1) through (6-3) compounds:

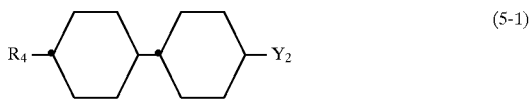

(5-1)

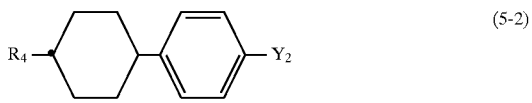

(5-2)

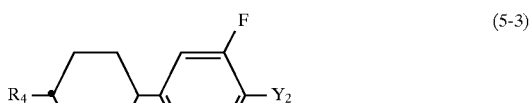

(5-3)

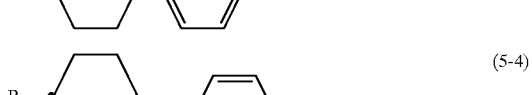

(5-4)

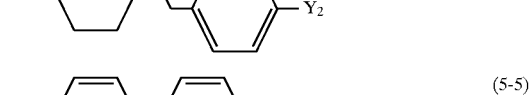

(5-5)

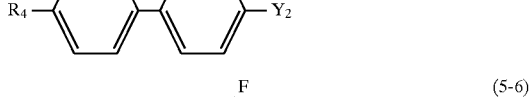

(5-6)

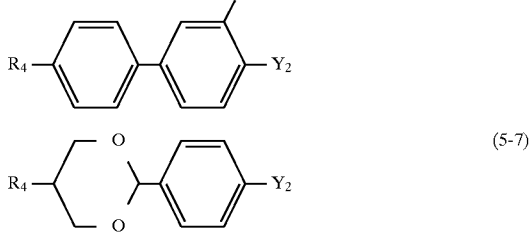

(5-7)

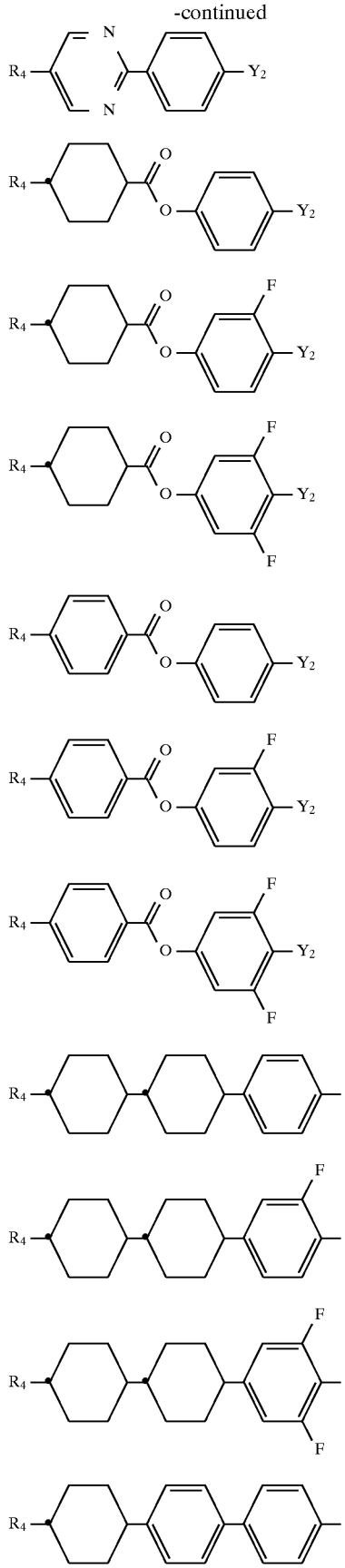

-continued

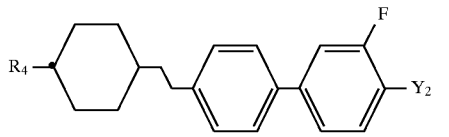 (5-30)

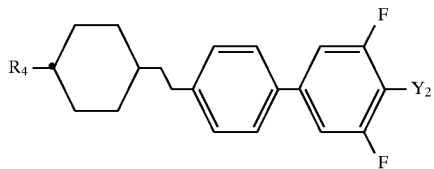 (5-31)

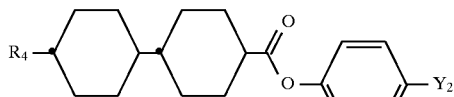 (5-32)

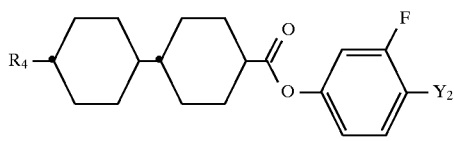 (5-33)

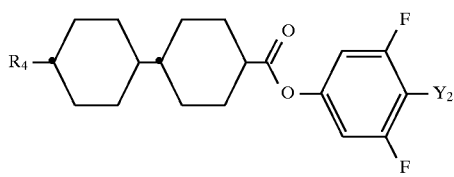 (5-34)

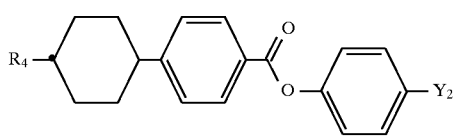 (5-35)

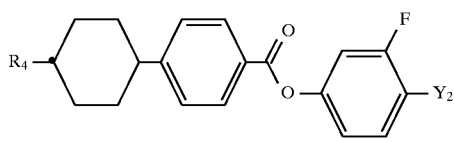 (5-36)

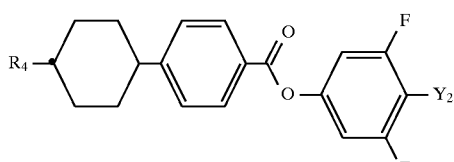 (5-37)

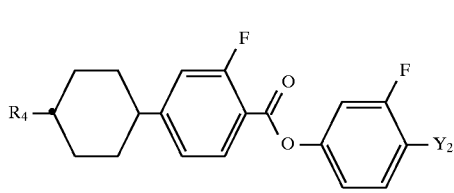 (5-38)

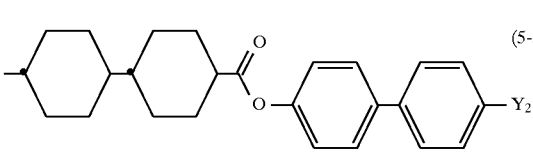 (5-39)

-continued

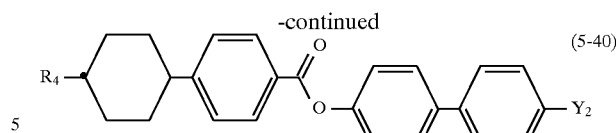 (5-40)

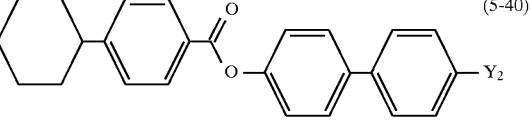 (6-1)

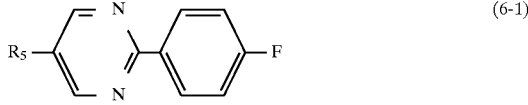 (6-2)

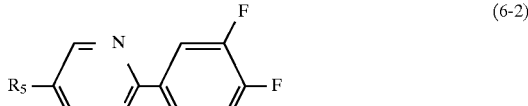 (6-3)

wherein $R_4$, $R_5$, and $Y_2$ have the same meanings as described above, and each of the elements that constitute the respective compounds may comprise isotopes of the element.

These compounds broadly expressed by formulas (5) and (6) have high positive values of $\Delta\epsilon$, and are used to reduce the threshold voltage of liquid crystal compositions. They are also used to adjust $\Delta n$ or to broaden the nematic range of liquid crystal compositions by, for example, elevating the clearing points of the compositions. In addition, they are used for improving the steepness of the threshold voltage of liquid crystal compositions for STN-mode or TN-mode display elements. Thus, these compounds are indispensable for the preparation of liquid crystal compositions for these particular uses.

When the compounds of formulas (5) and (6) are used in increased amounts, the threshold voltage of the resulting liquid crystal composition is reduced. However, viscosity of the resulting composition increases. Therefore, so long as the viscosity of the liquid crystal composition satisfies the required characteristics, it is advantageous that these compounds be used in as large amounts as possible so as to secure low voltage driving.

Thus, when liquid crystal compositions for STN-mode or TN-mode display elements are prepared, the compounds of formulas (5) or (6) are incorporated into the composition in amounts of 0.1–99.9% by weight, preferably 10–97% by weight, and more preferably 40–95% by weight.

Of the aforementioned third components, examples of the compounds of formula (7) include the following formula (7-1) through formula (7-11) compounds, examples of the compounds of formula (8) include the following formula (8-1) through (8-18) compounds, and examples of the compounds of formula (9) include the following formula (9-1) through (9-6) compounds.

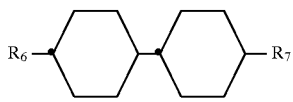 (7-1)

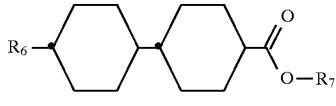 (7-2)

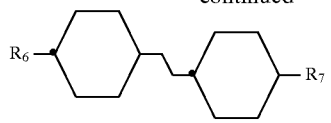 (7-3)
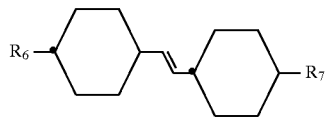 (7-4)
 (7-5)
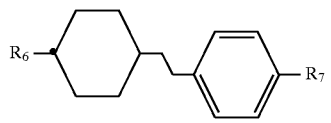 (7-6)
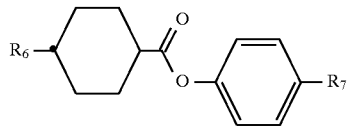 (7-7)
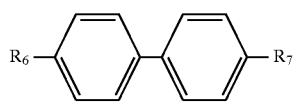 (7-8)
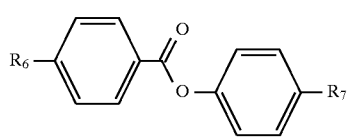 (7-9)
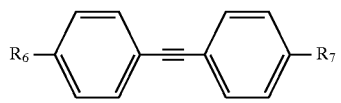 (7-10)
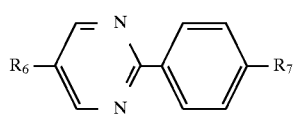 (7-11)
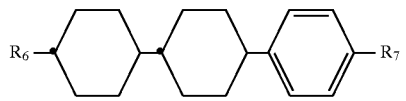 (8-1)
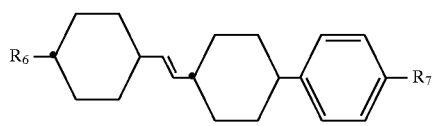 (8-2)
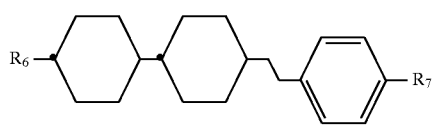 (8-3)
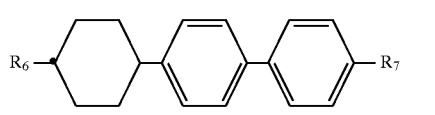 (8-4)
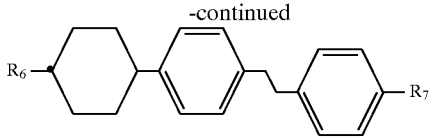 (8-5)
 (8-6)
 (8-7)
 (8-8)
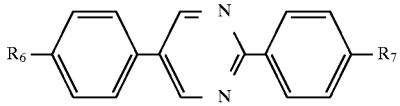 (8-9)
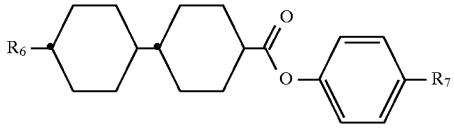 (8-10)
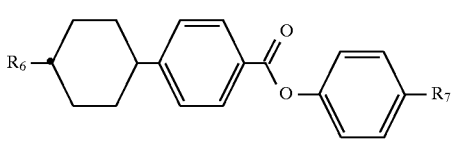 (8-11)
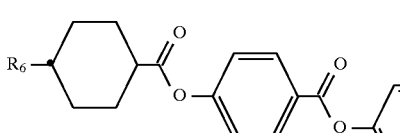 (8-12)
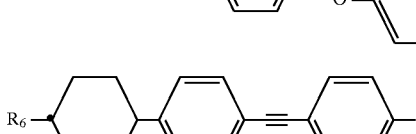 (8-13)
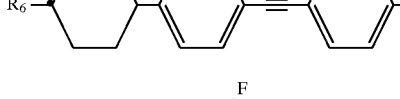 (8-14)
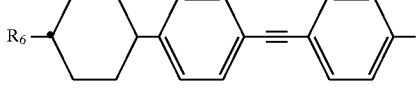 (8-15)
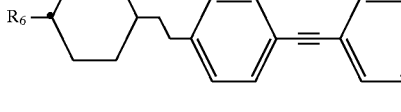 (8-16)
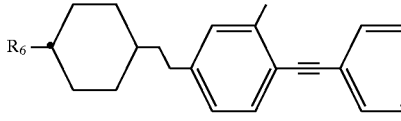

-continued

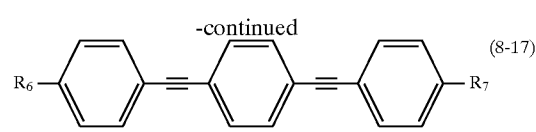 (8-17)

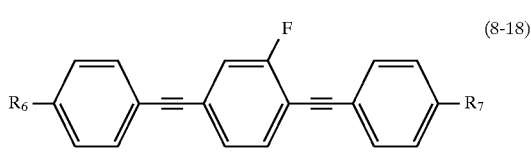 (8-18)

 (9-1)

 (9-2)

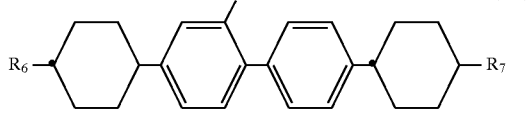 (9-3)

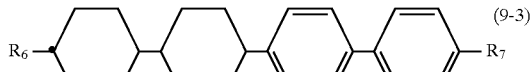 (9-4)

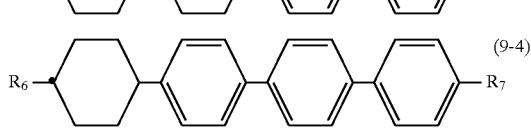 (9-5)

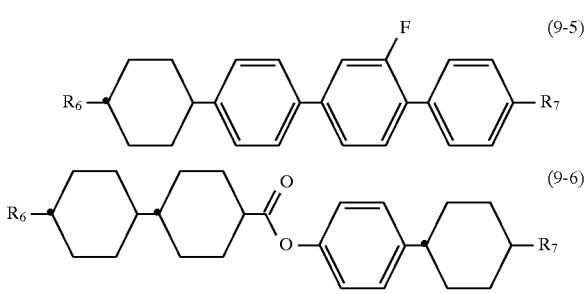 (9-6)

wherein $R_6$ and $R_7$ have the same meanings as described above, and each of the elements that constitute the respective compounds may comprise isotopes of the element.

These compounds broadly expressed by formulas (7) through (9) have small absolute values of $\Delta\epsilon$, and are close to neutral. Of these compounds, compounds of formula (7) are primarily used to adjust the viscosity or $\Delta n$ of liquid crystal compositions, whereas compounds of formulas (8) and (9) are used to broaden the nematic range of liquid crystal compositions by, for example, elevating the clearing point, or to adjust $\Delta n$.

When the compounds of formulas (7) through (9) are used in increased amounts, the threshold voltage of the resulting liquid crystal composition increases. However, viscosity of the resulting compound reduces. Therefore, so long as the threshold voltage of the liquid crystal composition satisfies the required characteristics, it is advantageous that these compounds be used in as large amounts as possible.

Thus, when liquid crystal compositions for TFTs are prepared, the compounds of formulas (7) through (9) are incorporated into the composition in amounts of 40% by weight or less, preferably 35% by weight or less, based on the total weight of the liquid crystal composition. In contrast, when liquid crystal compositions for STN-mode or TN-mode display elements are prepared, these compounds are incorporated into the composition in amounts of 70% by weight or less, preferably 60% by weight or less, based on the total weight of the liquid crystal composition.

Among optional components, optically active compounds are incorporated, excepting special cases such as the case in which the resultant compositions are used for preparing OCB-mode liquid crystal display elements, for the purpose of inducing the formation of the helical structure of the liquid crystal composition so as to adjust the twist angle, which in turn prevents occurrence of reverse twisting.

The optically active compounds are selected from among broad ranges of known compounds so long as the above purposes are achieved. Examples of preferred optically active compounds include the following compounds of formulas (Op-1) through (Op-8).

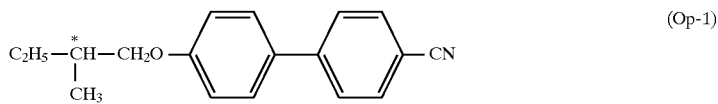 (Op-1)

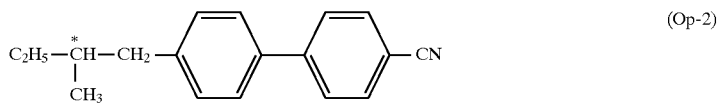 (Op-2)

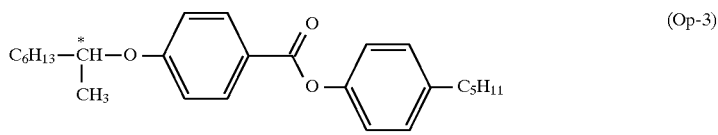 (Op-3)

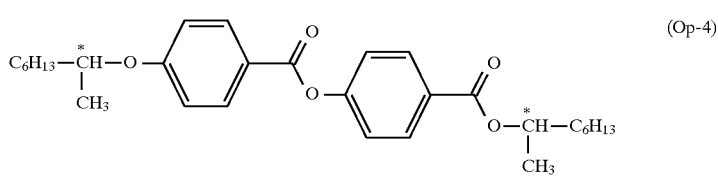 (Op-4)

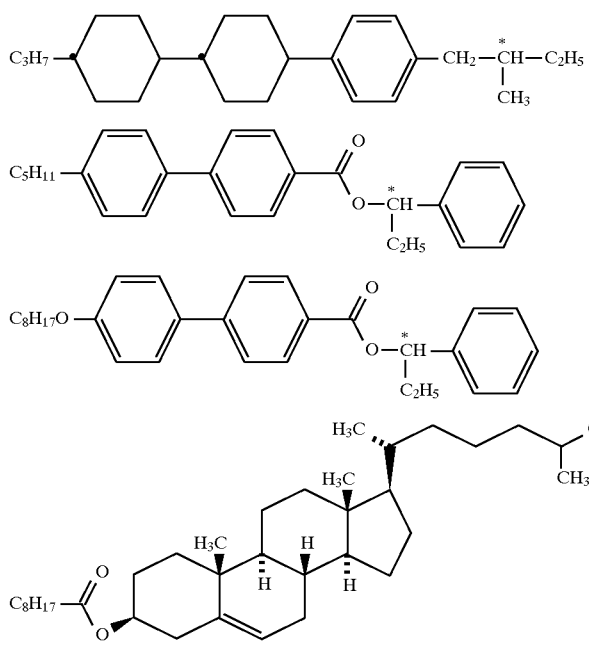

(Op-5)

(Op-6)

(Op-7)

(Op-8)

When these optically active compounds are incorporated, the pitch of the twist of liquid crystal compositions is regulated. The pitch of twist is preferably between 40 and 200 μm in the case where the liquid crystal composition is used for TFT-mode and TN-mode display elements, between 6 and 20 μm in the case where the composition is used for STN-mode display elements, and between 1.5 and 4 μm in the case where the composition is used for bistable TN-mode display elements.

Two or more different species of optically active compounds may be incorporated so as to control the temperature dependency of the pitch.

The liquid crystal compositions of the present invention are prepared by methods known per se, for example, by a method in which a variety of components are melted one another at high temperature.

If dichroic dyes such as merocyanine-type, styryl-type, azo-type, azomethine-type, azoxy-type, quinophthalone-type, anthraquinone-type, or tetrazine-type dyes are added during the preparation of a composition, the resulting liquid crystal composition can be used as a material of guest-host (GH) mode display elements. The liquid crystal compositions of the present invention can also be used for the preparation of NCAPs that are prepared by microcapsulating nematic liquid crystals as well as polymer dispersion-type liquid display elements (PDLCDs) typified by polymer network liquid crystal displays (PNLCDs) that are prepared by forming in the liquid crystal a three-dimensional network structure of a polymer. Moreover, the liquid crystal compositions of the present invention can be used for the preparation of ECB-mode or DS-mode display elements.

The nematic liquid crystal compositions of the present invention are prepared as described above. The following Composition Example Nos. 1 through 46 illustrate the examples of the compositions.

In each one of the Composition Examples, the compounds employed are represented as shown in Table 1 below.

The compound Nos. allotted to the compounds of the present invention are the same as those used in the section of working examples ("Examples") described hereinlater.

Unless otherwise indicated, the percentage of each compound denotes % by weight.

The physical properties of each composition are expressed by $T_{N1}$ (nematic phase-isotropic liquid phase transition point or clearing point), η (viscosity; measured at 20.0° C.), Δn1 (birefringence index; measured at 25.0° C.), Δε1 (dielectric anisotropy value; measured at 25.0° C.), and $V_{th}$ (threshold voltage; measured at 25.0° C.).

TABLE 1

| $R-(A_2)-Z_1\ldots-Z_n-(A_n)-X$ | |
|---|---|
| 1) Left terminal group R— | Symbol |
| $C_nH_{2n+1}-$ | n- |
| $C_nH_{2n+1}O-$ | nO— |
| $C_nH_{2n+1}OC_mH_{2m}-$ | nOm- |
| $CH_2=CH-$ | V— |
| $CH_2=CHC_nH_{2n}-$ | Vn- |
| $C_nH_{2n+1}CH=CHC_mH_{2m}-$ | nVm- |
| $C_nH_{2n+1}CH=CHC_mH_{2m}CH=CHC_kH_{2k}-$ | nVmVk- |
| 2) Ring structure $-(A_2)-, -(A_n)-$ | A Symbol |
|  | B |
| 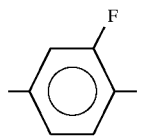 | B(F) |

TABLE 1-continued

R—(A₂)—Z₁ ... —Zₙ—(Aₙ)—X

| Structure | Symbol |
|---|---|
| (difluorobenzene, F at 2,6) | B(F, F) |
| (cyclohexane) | H |
| (pyrimidine) | Py |
| (dioxane) | D |
| (cyclohexene) | Ch |

3) Bonding group —Z₁—, —Zₙ—

| Group | Symbol |
|---|---|
| —C₂H₄— | 2 |
| —C₄H₈— | 4 |
| —COO— | E |
| —C≡C— | T |
| —CH=CH— | V |
| —CF₂O— | CF2O |
| —OCF₂— | OCF2 |
| —C₃H₆O— | 3O |

4) Right terminal group —X

| Group | Symbol |
|---|---|
| —F | -F |
| —Cl | -CL |
| —CN | -C |
| —CF₃ | -CF3 |
| —OCF₃ | -OCF3 |
| —OCF₂H | -OCF2H |
| —CₙH₂ₙ₊₁ | -n |
| —OCₙH₂ₙ₊₁ | -On |
| —COOCH₃ | -Eme |
| —CₙH₂ₙCH=CH₂ | -nV |
| —CₘH₂ₘCH=CHCₙH₂ₙ₊₁ | -mVn |
| —CₘH₂ₘCH=CHCₙH₂ₙF | -mVnF |
| —CH=CF₂ | -VFF |

5) Examples of representation

Ex. 1 3-H2B(F,F)B(F)-F

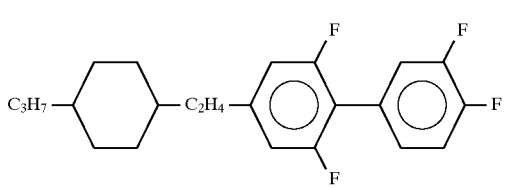

Ex. 2 3-HB(F)TB-2

(C₃H₇—cyclohexane—fluorobenzene—C≡C—benzene—C₂H₅)

Ex. 3 1V2-BEB(F,F)-C (CH₃CH=CHCH₂—benzene—COO—difluorobenzene—CN)

COMPOSITION EXAMPLE 1

A liquid crystal composition containing the following compounds was prepared.

| Compound | No. | % |
|---|---|---|
| 3-DB (F, F) B (F)—F | (No. 23) | 5.0% |
| 3-DB (F, F) B—F | (No. 22) | 5.0% |
| 1V2-BEB (F, F)—C | | 5.0% |
| 3-HB—C | | 25.0% |
| 1-BTB-3 | | 5.0% |
| 2-BTB-1 | | 5.0% |
| 3-HH-4 | | 6.0% |
| 3-HHB-1 | | 11.0% |
| 3-HHB-3 | | 9.0% |
| 3-H2BTB-2 | | 4.0% |
| 3-H2BTB-3 | | 4.0% |
| 3-H2BTB-4 | | 4.0% |
| 3-HB (F) TB-2 | | 6.0% |
| 3-HB (F) TB-3 | | 6.0% |

Physical properties of the composition were as follows:
$T_{N1}$=90.0° C.
$\eta$=21.5 mPa.s
$\Delta n1$=0.159
$\Delta \epsilon 1$=8.9
$V_{th}$=1.78 V

COMPOSITION EXAMPLE 2

A liquid crystal composition containing the following compounds was prepared.

| Compound | No. | % |
|---|---|---|
| 3-DB (F, F) B (F)—OCF3 | (No. 26) | 5.0% |
| 3-DB (F) B (F, F)—F | (No. 4) | 5.0% |
| V2-HB—C | | 12.0% |
| 1V2-HB—C | | 12.0% |
| 3-HB—C | | 18.0% |
| 3-HB (F)—C | | 5.0% |
| 2-BTB-1 | | 2.0% |
| 3-HH-4 | | 4.0% |
| 3-HH—VFF | | 6.0% |
| 2-HHB—C | | 3.0% |
| 3-HHB—C | | 6.0% |
| 3-HB (F) TB-2 | | 8.0% |
| 3-H2BTB-2 | | 5.0% |
| 3-H2BTB-3 | | 5.0% |
| 3-H2BTB-4 | | 4.0% |

Physical properties of the composition were as follows:
$T_{N1}$=85.7° C.

η=23.4 mPa.s
Δn1=0.156
Δε1=10.3
$V_{th}$=1.82 V

COMPOSITION EXAMPLE 3

A liquid crystal composition containing the following compounds was prepared.

| | | |
|---|---|---|
| 3-DB (F, F) B (F, F)—CF3 | (No. 30) | 3.0% |
| 3-DB (F, F) B—CL | (No. 32) | 3.0% |
| 2O1-BEB (F)—C | | 5.0% |
| 3O1-BEB (F)—C | | 11.0% |
| 4O1-BEB (F)—C | | 13.0% |
| 5O1-BBB (F)—C | | 13.0% |
| 2-HHB (F)—C | | 15.0% |
| 3-HHB (F)—C | | 15.0% |
| 3-HB (F) TB-2 | | 4.0% |
| 3-HB (F) TB-3 | | 4.0% |
| 3-HB (F) TB-4 | | 4.0% |
| 3-HHB-1 | | 6.0% |
| 3-HHB—O1 | | 4.0% |

Physical properties of the composition were as follows:
$T_{N1}$=91.5° C.
η=87.8 mPa.s
Δn1=0.150
Δε1=31.0
$V_{th}$=0.87 V

COMPOSITION EXAMPLE 4

A liquid crystal composition containing the following compounds was prepared.

| | | |
|---|---|---|
| 3-DB (F, F) B (F)—F | (No. 23) | 2.0% |
| 3-DB (F, F) B—CL | (No. 32) | 2.0% |
| 3-DB (F) B (F, F)—F | (No. 4) | 2.0% |
| 5-PyB—F | | 4.0% |
| 3-PyB (F)—F | | 4.0% |
| 2-BB—C | | 5.0% |
| 5-BB—C | | 5.0% |
| 2-PyB-2 | | 2.0% |
| 3-PyB-2 | | 2.0% |
| 4-PyB-2 | | 2.0% |
| 6-PyB—O5 | | 3.0% |
| 6-PyB—O6 | | 3.0% |
| 6-PyB—O7 | | 3.0% |
| 6-PyB—O8 | | 3.0% |
| 3-PyBB—F | | 6.0% |
| 4-PyBB—F | | 4.0% |
| 5-PyBB—F | | 6.0% |
| 3-HHB-1 | | 6.0% |
| 3-HHB-3 | | 8.0% |
| 2-H2BTB-2 | | 4.0% |
| 2-H2BTB-3 | | 4.0% |
| 2-H2BTB-4 | | 5.0% |
| 3-H2BTB-2 | | 5.0% |
| 3-H2BTB-3 | | 5.0% |
| 3-H2BTB-4 | | 5.0% |

Physical properties of the composition were as follows:
$T_{N1}$=93.0° C.
η=36.4 mPa.s
Δn1=0.197
Δε1=6.6
$V_{th}$=2.22 V

COMPOSITION EXAMPLE 5

A liquid crystal composition containing the following compounds was prepared.

| | | |
|---|---|---|
| 3-DB (F, F) B—F | (No. 22) | 2.0% |
| 3-DB (F, F) B (F)—OCF3 | (No. 26) | 2.0% |
| 3-DB (F, F) B (F, F)—CF3 | (No. 29) | 2.0% |
| 3-DB—C | | 10.0% |
| 4-DB—C | | 10.0% |
| 2-BEB—C | | 6.0% |
| 3-BEB—C | | 4.0% |
| 3-PyB (F)—F | | 6.0% |
| 3-HEB—O4 | | 8.0% |
| 4-HEB—O2 | | 6.0% |
| 5-HEB—O1 | | 6.0% |
| 3-HEB—O2 | | 5.0% |
| 5-HEB—O2 | | 4.0% |
| 5-HEB-5 | | 5.0% |
| 4-HEB-5 | | 5.0% |
| 1O—BEB-2 | | 4.0% |
| 3-HHB-1 | | 6.0% |
| 3-HHEBB—C | | 3.0% |
| 3-HBEBB—C | | 3.0% |
| 5-HBEBB—C | | 3.0% |

Physical properties of the composition were as follows:
$T_{N1}$=68.1° C.
η=40.3 mPa.s
Δn1=0.116
Δε1=11.0
$V_{th}$=1.35 V

COMPOSITION EXAMPLE 6

A liquid crystal composition containing the following compounds was prepared.

| | | |
|---|---|---|
| 3-DB (F, F) B (F)—F | (No. 23) | 5.0% |
| 3-HB—C | | 18.0% |
| 5-HB—C | | 3.0% |
| 1O1-HB—C | | 5.0% |
| 3-HB (F)—C | | 10.0% |
| 2-PyB-2 | | 2.0% |
| 3-PyB-2 | | 2.0% |
| 4-PyB-2 | | 2.0% |
| 1O1-HH-3 | | 7.0% |
| 2-BTB—O1 | | 7.0% |
| 3-HHB-1 | | 7.0% |
| 3-HHB—F | | 4.0% |
| 3-HHB—O1 | | 4.0% |
| 3-HHB-3 | | 8.0% |
| 3-H2BTB-2 | | 3.0% |
| 3-H2BTB-3 | | 3.0% |
| 2-PyBH-3 | | 4.0% |
| 3-PyBH-3 | | 3.0% |
| 3-PyBB-2 | | 3.0% |

Physical properties of the composition were as follows:
$T_{N1}$=79.5° C.
η=19.4 mPa.s
Δn1=0.139
Δε1=8.2
$V_{th}$=1.73 V

COMPOSITION EXAMPLE 7

A liquid crystal composition containing the following compounds was prepared.

| | | |
|---|---|---|
| 3-DB (F, F) B—F | (No. 22) | 5.0% |
| 3-DB (F, F) B (F)—OCF3 | (No. 26) | 5.0% |
| 2O1-BEB (F)—C | | 5.0% |

-continued

| | | |
|---|---|---|
| 3O1-BEB (F)—C | | 6.0% |
| 5O1-BEB (F)—C | | 4.0% |
| 1V2-BEB (F, F)—C | | 10.0% |
| 3-HH—EMe | | 10.0% |
| 3-HB—O2 | | 18.0% |
| 3-HHEB—F | | 3.0% |
| 5-HHEB—F | | 3.0% |
| 3-HBEB—F | | 4.0% |
| 2O1-HBEB (F)—C | | 2.0% |
| 3-HB (F) EB (F)—C | | 2.0% |
| 3-HBEB (F, F)—C | | 2.0% |
| 3-HHB—F | | 4.0% |
| 3-HHB—O1 | | 4.0% |
| 3-HHB-3 | | 9.0% |
| 3-HEBEB—F | | 2.0% |
| 3-HEBEB-1 | | 2.0% |

Physical properties of the composition were as follows:

$T_{N1}$=75.1° C.

$\eta$=36.5 mPa.s $\Delta n1$=0.114

$\Delta \epsilon 1$=23.3

$V_{th}$=1.00 V

COMPOSITION EXAMPLE 8

A liquid crystal composition containing the following compounds was prepared.

| | | |
|---|---|---|
| 3-DB (F, F) B—CL | (No. 32) | 3.0% |
| 5-BEB (F)—C | | 5.0% |
| V—HB—C | | 8.0% |
| 5-PyB—C | | 6.0% |
| 4-BB-3 | | 11.0% |
| 3-HH-2V | | 10.0% |
| 5-HH—V | | 11.0% |
| V—HHB-1 | | 7.0% |
| V2-HHB-1 | | 15.0% |
| 3-HHB-1 | | 9.0% |
| 1V2-HBB-2 | | 10.0% |
| 3-HHEBH-3 | | 5.0% |

Physical properties of the composition were as follows:

$T_{N1}$=91.4° C.

$\eta$=16.5 mPa.s $\Delta n1$=0.115

$\Delta \epsilon 1$=4.8

$V_{th}$=2.36 V

COMPOSITION EXAMPLE 9

A liquid crystal composition containing the following compounds was prepared.

| | | |
|---|---|---|
| 3-DB (F, F) B—F | (No. 22) | 4.0% |
| 3-DB (F, F) B—CL | (No. 32) | 4.0% |
| 2O1-BEB (F)—C | | 5.0% |
| 3O1-BEB (F)—C | | 12.0% |
| 1V2-BEB (F, F)—C | | 16.0% |
| 3-HB—O2 | | 10.0% |
| 3-HH-4 | | 3.0% |
| 3-HHB—F | | 3.0% |
| 3-HHB-1 | | 8.0% |
| 3-HHB—O1 | | 4.0% |
| 3-HBEB—F | | 4.0% |
| 3-HHEB—F | | 7.0% |
| 5-HHEB—F | | 3.0% |
| 3-H2BTB-2 | | 4.0% |
| 3-H2BTB-3 | | 4.0% |
| 3-H2BTB-4 | | 4.0% |
| 3-HB (F) TB-2 | | 5.0% |

Physical properties of the composition were as follows:

$T_{N1}$=88.9° C.

$\eta$=40.9 mPa.s $\Delta n1$=0.146

$\Delta \epsilon 1$=28.5

$V_{th}$=0.98 V

COMPOSITION EXAMPLE 10

A liquid crystal composition containing the following compounds was prepared.

| | | |
|---|---|---|
| 3-DB (F, F) B (F)—F | (No. 23) | 2.0% |
| 3-DB (F, F) B (F, F)—CF3 | (No. 30) | 2.0% |
| 2-BEB—C | | 12.0% |
| 4-BEB—C | | 6.0% |
| 3-HB—C | | 2.8.0% |
| 3-HEB—O4 | | 12.0% |
| 4-HEB—O2 | | 8.0% |
| 5-HEB—O1 | | 8.0% |
| 3-HEB—O2 | | 6.0% |
| 5-HEB—O2 | | 5.0% |
| 3-HHB-1 | | 7.0% |
| 3-HHB—O1 | | 4.0% |

Physical properties of the composition were as follows:

$T_{N1}$=61.2° C.

$\eta$=26.6 mPa.s $\Delta n1$=0.110

$\Delta \epsilon 1$=10.1

$V_{th}$=1.33 V

COMPOSITION EXAMPLE 11

A liquid crystal composition containing the following compounds was prepared.

| | | |
|---|---|---|
| 3-DB (F, F) B (F, F)—CF3 | (No. 30) | 2.0% |
| 3-DB (F) B (F, F)—F | (No. 4) | 2.0% |
| 2-BEB—C | | 10.0% |
| 5-BB—C | | 8.0% |
| 7-BB—C | | 7.0% |
| 1-BTB-3 | | 7.0% |
| 2-BTB-1 | | 10.0% |
| 1O-BEB-2 | | 10.0% |
| 1O-BEB-5 | | 12.0% |
| 2-HHB-1 | | 4.0% |
| 3-HHB—F | | 4.0% |
| 3-HHB-1 | | 7.0% |
| 3-HHB—O1 | | 4.0% |
| 3-HHB-3 | | 13.0% |

Physical properties of the composition were as follows:

$T_{N1}$=6.6.1° C.

$\eta$=21.0 mPa.s $\Delta n1$=0.157

$\Delta \epsilon 1$=6.9

$V_{th}$=1.72 V

COMPOSITION EXAMPLE 12

A liquid crystal composition containing the following compounds was prepared.

| | | |
|---|---|---|
| 3-DB (F, F) B (F)—F | (No. 23) | 3.0% |
| 3-DB (F, F) B (F)—OCF3 | (No. 26) | 3.0% |
| 2-HHB (F)—F | | 17.0% |
| 3-HHB (F)—F | | 17.0% |
| 5-HHB (F)—F | | 16.0% |
| 2-H2HB (F)—F | | 10.0% |
| 3-H2HB (F)—F | | 5.0% |
| 5-H2HB (F)—F | | 10.0% |
| 2-HBB (F)—F | | 6.0% |
| 5-HBB (F)—F | | 13.0% |

Physical properties of the composition were as follows:
$T_{N1}$=97.8° C.
$\eta$=26.7 mPa.s
$\Delta n1$=0.094
$\Delta \epsilon 1$=6.1
$V_{th}$=2.03 V

COMPOSITION EXAMPLE 13

A liquid crystal composition containing the following compounds was prepared.

| | | |
|---|---|---|
| 3-DB (F, F) B—F | (No. 22) | 3.0% |
| 3-DB (F, F) B (F, F)—CF3 | (No. 30) | 3.0% |
| 7-HB (F)—F | | 5.0% |
| 5-H2B (F)—F | | 5.0% |
| 3-HB—O2 | | 10.0% |
| 3-HH-4 | | 5.0% |
| 2-HHB (F)—F | | 10.0% |
| 3-HHB (F)—F | | 10.0% |
| 5-HHB (F)—F | | 10.0% |
| 3-H2HB (F)—F | | 5.0% |
| 5-HBB (F)—F | | 6.0% |
| 2-H2BB (F)—F | | 5.0% |
| 3-H2BB (F)—F | | 6.0% |
| 3-HHB-1 | | 8.0% |
| 3-HHB—O1 | | 5.0% |
| 3-HHB-3 | | 4.0% |

Physical properties of the composition were as follows:
$T_{N1}$=87.1° C.
$\eta$=18.9 mPa.s
$\Delta n1$=0.093
$\Delta \epsilon 1$=4.3
$V_{th}$=2.41 V

COMPOSITION EXAMPLE 14

A liquid crystal composition containing the following compounds was prepared.

| | | |
|---|---|---|
| 3-DB (F, F) B—CL | (No. 32) | 5.0% |
| 3-DB (F) B (F, F)—F | (No. 4) | 5.0% |
| 7-HB (F)—F | | 3.0% |
| 3-HB—O2 | | 7.0% |
| 2-HHB (F)—F | | 10.0% |
| 3-HHB (F)—F | | 10.0% |
| 5-HHB (F)—F | | 10.0% |
| 2-HBB (F)—F | | 9.0% |
| 3-HBB (F)—F | | 9.0% |
| 5-HBB (F)—F | | 16.0% |
| 2-HBB—F | | 4.0% |
| 3-HBB—F | | 4.0% |
| 5-HBB—F | | 3.0% |
| 3-HBB (F, F)—F | | 5.0% |

Physical properties of the composition were as follows:
$T_{N1}$=84.3° C.
$\eta$=27.9 mPa.s
$\Delta n1$=0.117
$\Delta \epsilon 1$=6.9
$V_{th}$=1.82 V

COMPOSITION EXAMPLE 15

A liquid crystal composition containing the following compounds was prepared.

| | | |
|---|---|---|
| 3-DB (F, F) B (F)—F | (No. 23) | 15.0% |
| 3-DB (F, F) B—F | (No. 22) | 10.0% |
| 3-DB (F, F) B (F)—OCF3 | (No. 26) | 5.0% |
| 3-DB (F, F) B (F, F)—CF3 | (No. 30) | 5.0% |
| 7-HB (F, F)—F | | 2.0% |
| 3-H2HB (F, F)—F | | 12.0% |
| 4-H2HB (F, F)—F | | 10.0% |
| 3-HHB (F, F)—F | | 10.0% |
| 4-HHB (F, F)—F | | 5.0% |
| 3-HH2B (F, F)—F | | 15.0% |
| 5-HBB (F, F)—F | | 11.0% |

Physical properties of the composition were as follows:
$T_{N1}$=61.7° C.
$\eta$=35.4 mPa.s
$\Delta n1$=0.094
$\Delta \epsilon 1$=13.1
$V_{th}$=1.24 V

COMPOSITION EXAMPLE 16

A liquid crystal composition containing the following compounds was prepared.

| | | |
|---|---|---|
| 3-DB (F, F) B—F | (No. 22) | 7.0% |
| 3-DB (F, F) B (F, F)—CF3 | (No. 30) | 5.0% |
| 3-DB (F) B (F, F)—F | (No. 4) | 6.0% |
| 7-HB (F, F)—F | | 3.0% |
| 3-H2HB (F, F)—F | | 12.0% |
| 4-H2HB (F, F)—F | | 10.0% |
| 3-HHB (F, F)—F | | 10.0% |
| 4-HHB (F, F)—F | | 5.0% |
| 3-HBB (F, F)—F | | 10.0% |
| 3-HHEB (F, F)—F | | 7.0% |
| 4-HHEB (F, F)—F | | 3.0% |
| 5-HHEB (F, F)—F | | 3.0% |
| 3-HBEB (F, F)—F | | 5.0% |
| 5-HBEB (F, F)—F | | 3.0% |
| 3-HDB (F, F)—F | | 5.0% |
| 3-HHBB (F, F)—F | | 6.0% |

Physical properties of the composition were as follows:
$T_{N1}$=72.9° C.
$\eta$=39.8 mPa.s
$\Delta n1$=0.094
$\Delta \epsilon 1$=14.9
$V_{th}$=1.28 V

COMPOSITION EXAMPLE 17

A liquid crystal composition containing the following compounds was prepared.

| | | |
|---|---|---|
| 3-DB (F, F) B—F | (No. 22) | 5.0% |
| 3-HB—CL | | 10.0% |
| 5-HB—CL | | 4.0% |
| 7-HB—CL | | 4.0% |

-continued

| | | |
|---|---|---|
| 1O1-HH-5 | | 5.0% |
| 2-HBB (F)—F | | 8.0% |
| 3-HBB (F)—F | | 8.0% |
| 5-HBB (F)—F | | 14.0% |
| 4-HHB—CL | | 8.0% |
| 5-HHB—CL | | 8.0% |
| 3-H2HB (F)—CL | | 4.0% |
| 3-HBB (F, F)—F | | 5.0% |
| 5-H2BB (F, F)—F | | 9.0% |
| 3-HB (F) VB-2 | | 4.0% |
| 3-HB (F) VB-3 | | 4.0% |

Physical properties of the composition were as follows:
$T_{N1}=91.1°$ C.
$\eta=21.3$ mPa.s
$\Delta n1=0.128$
$\Delta \epsilon 1=5.2$
$V_{th}=2.26$ V

COMPOSITION EXAMPLE 18

A liquid crystal composition containing the following compounds was prepared.

| | | |
|---|---|---|
| 3-DB (F, F) B (F)—F | (No. 23) | 5.0% |
| 3-DB (F, F) B—CL | (No. 32) | 5.0% |
| 3-DB (F) B (F, F)—F | (No. 4) | 5.0% |
| 3-HHB (F, F)—F | | 9.0% |
| 3-H2HB (F, F)—F | | 8.0% |
| 4-H2HB (F, F)—F | | 8.0% |
| 5-H2HB (F, F)—F | | 8.0% |
| 3-HBB (F, F)—F | | 21.0% |
| 5-HBB (F, F)—F | | 5.0% |
| 3-H2BB (F, F)—F | | 10.0% |
| 5-HHBB (F, F)—F | | 3.0% |
| 3-HH2BB (F, F)—F | | 3.0% |
| 5-HHEBB—F | | 2.0% |
| 1O1-HBBH-4 | | 4.0% |
| 1O1-HBBH-5 | | 4.0% |

Physical properties of the composition were as follows:
$T_{N1}=93.8°$ C.
$\eta=39.5$ mPa.s
$\Delta n1=0.116$
$\Delta \epsilon 1=10.8$
$V_{th}=1.46$ V

COMPOSITION EXAMPLE 19

A liquid crystal composition containing the following compounds was prepared.

| | | |
|---|---|---|
| 3-DB (F, F) B—F | (No. 22) | 4.0% |
| 3-DB (F, F) B (F)—OCF3 | (No. 26) | 4.0% |
| 5-HB—F | | 12.0% |
| 6-HB—F | | 9.0% |
| 7-HB—F | | 7.0% |
| 2-HHB—OCF3 | | 7.0% |
| 3-HHB—OCF3 | | 11.0% |
| 4-HHB—OCF3 | | 7.0% |
| 5-HHB—OCF3 | | 5.0% |
| 3-HH2B—OCF3 | | 4.0% |
| 5-HH2B—OCF3 | | 4.0% |
| 3-HHB (F, F)—OCF3 | | 5.0% |
| 3-HBB (F)—F | | 2.0% |
| 5-HBB (F)—F | | 10.0% |
| 3-HH2B (F)—F | | 3.0% |
| 3-HB (F) BH-3 | | 3.0% |
| 5-HBBH-3 | | 3.0% |

Physical properties of the composition were as follows:
$T_{N1}=84.5°$ C.
$\eta=16.0$ mPa.s
$\Delta n1=0.090$
$\Delta \epsilon 1=5.5$
$V_{th}=2.18$ V

COMPOSITION EXAMPLE 20

A liquid crystal composition containing the following compounds was prepared.

| | | |
|---|---|---|
| 3-DB (F) B (F, F)—F | (No. 4) | 5.0% |
| 5-H4HB (F, F)—F | | 7.0% |
| 5-H4HB—OCF3 | | 15.0% |
| 3-H4HB (F, F)—CF3 | | 8.0% |
| 5-H4HB (F, F)—CF3 | | 5.0% |
| 3-HB—CL | | 6.0% |
| 5-HB—CL | | 4.0% |
| 2-H2BB (F)—F | | 5.0% |
| 3-H2BB (F)—F | | 10.0% |
| 5-HVHB (F, F)—F | | 5.0% |
| 3-HHB—OCF3 | | 5.0% |
| 3-H2HB—OCF3 | | 5.0% |
| V-HHB (F)—F | | 5.0% |
| 3-HChB (F)—F | | 5.0% |
| 5-HHEB—OCF3 | | 2.0% |
| 3-HBEB (F, F)—F | | 5.0% |
| 5-HH—V2F | | 3.0% |

Physical properties of the composition were as follows:
$T_{N1}=69.2°$ C.
$\eta=25.7$ mPa.s
$\Delta n1=0.091$
$\Delta \epsilon 1=8.8$
$V_{th}=1.65$ V

COMPOSITION EXAMPLE 21

A liquid crystal composition containing the following compounds was prepared.

| | | |
|---|---|---|
| 3-DB (F, F) B (F)—F | (No. 23) | 10.0% |
| 3-DB (F, F) B—F | (No. 22) | 10.0% |
| 2-HHB (F)—F | | 2.0% |
| 3-HHB (F)—F | | 2.0% |
| 5-HHB (F)—F | | 2.0% |
| 2-HBB (F)—F | | 6.0% |
| 3-HBB (F)—F | | 6.0% |
| 5-HBB (F)—F | | 10.0% |
| 2-H2BB (F)—F | | 9.0% |
| 3-H2BB (F)—F | | 9.0% |
| 3-HBB (F, F)—F | | 5.0% |
| 5-HBB (F, F)—F | | 19.0% |
| 1O1-HBBH-4 | | 5.0% |
| 1O1-HBBH-5 | | 5.0% |

Physical properties of the composition were as follows:
$T_{N1}=92.5°$ C.
$\eta=39.8$ mPa.s
$\Delta n1=0.133$
$\Delta \epsilon 1=8.9$
$V_{th}=1.70$ V

COMPOSITION EXAMPLE 22

A liquid crystal composition containing the following compounds was prepared.

| | | |
|---|---|---|
| 3-DB (F, F) CF2OB (F)—OCF3 | (No. 86) | 5.0% |
| 3-H2DB (F, F) B (F)—F | (No. 266) | 5.0% |
| 2O1-BEB (F)—C | | 5.0% |
| 3O1-BEB (F)—C | | 15.0% |
| 4O1-BEB (F)—C | | 13.0% |
| 5O1-BEB (F)—C | | 8.0% |
| 2-HHB (F)—C | | 10.0% |
| 3-HHB (F)—C | | 15.0% |
| 3-HB (F) TB-2 | | 4.0% |
| 3-HB (F) TB-3 | | 4.0% |
| 3-HB (F) TB-4 | | 4.0% |
| 3-HHB-1 | | 8.0% |
| 3-HHB—O1 | | 4.0% |

Physical properties of the composition were as follows:

$T_{N1}$=89.8° C.

$\eta$=88.5 mPa.s $\Delta n1$=0.149

$\Delta \epsilon 1$=31.4

$V_{th}$=0.84 V

COMPOSITION EXAMPLE 23

A liquid crystal composition containing the following compounds was prepared.

| | | |
|---|---|---|
| 5-DB (F, F) B (F)—OCF2C2CF2H | (No. 36) | 4.0% |
| 3-H2DB (F, F) B (F)—F | (No. 266) | 4.0% |
| 3-HB—C | | 16.0% |
| 5-HB—C | | 3.0% |
| 1O1-HB—C | | 10.0% |
| 3-HB (F)—C | | 10.0% |
| 2-PyB-2 | | 2.0% |
| 3-PyB-2 | | 2.0% |
| 4-PyB-2 | | 2.0% |
| 1O1-HH-3 | | 7.0% |
| 2-BTB—O1 | | 7.0% |
| 3-HHB-1 | | 7.0% |
| 3-HHB—F | | 4.0% |
| 3-HHB-3 | | 8.0% |
| 3-H2BTB-2 | | 3.0% |
| 3-H2BTB-3 | | 3.0% |
| 2-PyBH-3 | | 3.0% |
| 3-PyBH-3 | | 2.0% |
| 3-PyBB-2 | | 3.0% |

Physical properties of the composition were as follows:

$T_{N1}$=75.0° C.

$\eta$=23.5 mPa.s $\Delta n1$=0.138

$\Delta \epsilon 1$=9.6

$V_{th}$=1.61 V

COMPOSITION EXAMPLE 24

A liquid crystal composition containing the following compounds was prepared.

| | | |
|---|---|---|
| 3-DB (F, F) CF2OB (F)—OCF3 | (No. 86) | 5.0% |
| 5-DB (F, F) B (F)—OCF2CF2H | (No. 36) | 5.0% |
| 7-HB (F, F)—F | | 3.0% |
| 3-HB—O2 | | 7.0% |
| 2-HHB (F)—F | | 10.0% |
| 3-HHB (F)—F | | 10.0% |
| 5-HHB (F)—F | | 10.0% |
| 2-HBB (F)—F | | 9.0% |
| 3-HBB (F)—F | | 9.0% |
| 5-HBB (F)—F | | 16.0% |
| 2-HBB—F | | 4.0% |
| 3-HBB—F | | 4.0% |
| 5-HBB—F | | 3.0% |
| 3-HBB (F, F)—F | | 5.0% |

Physical properties of the composition were as follows:

$T_{N1}$=82.5° C.

$\eta$=27.5 mPa.s $\Delta n1$=0.115

$\Delta \epsilon 1$=7.6

$V_{th}$=1.74 V

COMPOSITION EXAMPLE 25

A liquid crystal composition containing the following compounds was prepared.

| | | |
|---|---|---|
| 3-DB (F, F) CF2OB (F)—OCF3 (No. 86) | | 5.0% |
| 5-H4HB (F, F)—F | | 7.0% |
| 5-H4HB—OCF3 | | 15.0% |
| 3-H4HB (F, F)—CF3 | | 8.0% |
| 5-H4HB (F, F)—CF3 | | 5.0% |
| 3-HB—CL | | 6.0% |
| 5-HB—CL | | 4.0% |
| 2-H2BB (F)—F | | 5.0% |
| 3-H2BB (F)—F | | 10.0% |
| 5-HVHB (F, F)—F | | 5.0% |
| 3-HHB—OCF3 | | 5.0% |
| 3-H2HB—OCF3 | | 5.0% |
| V-HHB (F)—F | | 5.0% |
| 3-HChB (F)—F | | 5.0% |
| 5-HHEB—OCF3 | | 2.0% |
| 3-HBEB (F, F)—F | | 5.0% |
| 5-HH—V2F | | 3.0% |

Physical properties of the composition were as follows:

$T_{N1}$=68.1° C.

$\eta$=25.0 mPa.s $\Delta n1$=0.091

$\Delta \epsilon 1$=9.1

$V_{th}$=1.57 V

COMPOSITION EXAMPLE 26

A liquid crystal composition containing the following compounds was prepared.

| | | |
|---|---|---|
| 3-DB (F) EB (F)—F (No. 43) | | 5.0% |
| 3-DB (F, F) B (F)—CF3 (No. 29) | | 5.0% |
| 1V2-BEB (F, F)—C | | 5.0% |
| 3-HB—C | | 25.0% |
| 1-BTB-3 | | 5.0% |
| 2-BTB-1 | | 5.0% |
| 3-HH-4 | | 6.0% |
| 3-HHB-1 | | 11.0% |
| 3-HHB-3 | | 9.0% |
| 3-H2BTB-2 | | 4.0% |
| 3-H2BTB-3 | | 4.0% |
| 3-H2BTB-4 | | 4.0% |
| 3-HB (F) TB—2 | | 6.0% |
| 3-HB (F) TB—3 | | 6.0% |

Physical properties of the composition were as follows:

$T_{N1}$=92.0° C.

$\eta$=21.3 mPa.s $\Delta n1$=0.165

Δε1=10.2
$V_{th}$=1.82 V

COMPOSITION EXAMPLE 27

A liquid crystal composition containing the following compounds was prepared.

| | |
|---|---|
| 3-DB (F) EB (F) —F (No. 43) | 5.0% |
| 3-DB (F, F) BB (F, F) —F (No. 143) | 5.0% |
| V2-HB—C | 12.0% |
| 1V2-HB—C | 12.0% |
| 3-HB—C | 18.0% |
| 3-HB (F) —C | 5.0% |
| 2-BTB-1 | 2.0% |
| 3-HH-4 | 4.0% |
| 3-HH—VFF | 6.0% |
| 2-HHB—C | 3.0% |
| 3-HHB—C | 6.0% |
| 3-HB (F) TB-2 | 8.0% |
| 3-H2BTB-2 | 5.0% |
| 3-H2BTB-3 | 5.0% |
| 3-H2BTB-4 | 4.0% |

Physical properties of the composition were as follows:
$T_{N1}$=93.5° C.
η=23.8 mPa.s
Δn1=0.161
Δε1=10.3
$V_{th}$=1.83 V

COMPOSITION EXAMPLE 28

A liquid crystal composition containing the following compounds was prepared.

| | |
|---|---|
| 3-DB (F, F) B (F) —CF3 (No. 29) | 6.0% |
| 3-DB (F, F) BB (F, F) —F (No. 143) | 5.0% |
| 5-PyB—F | 4.0% |
| 3-PyB (F) —F | 4.0% |
| 4-BB—C | 4.0% |
| 5-BB—C | 5.0% |
| 2-PyB-2 | 2.0% |
| 3-PyB-2 | 2.0% |
| 4-PyB-2 | 2.0% |
| 6-PyB—O5 | 3.0% |
| 6-PyB—O6 | 3.0% |
| 6-PyB—O7 | 3.0% |
| 6-PyB—O8 | 3.0% |
| 3-PyBB—F | 6.0% |
| 4-PyBB—F | 6.0% |
| 3-HHB-1 | 6.0% |
| 3-HHB-3 | 8.0% |
| 2-H2BTB-2 | 4.0% |
| 2-H2BTB-3 | 4.0% |
| 2-H2BTB-4 | 5.0% |
| 3-H2BTB-2 | 5.0% |
| 3-H2BTB-3 | 5.0% |
| 3-H2BTB-4 | 5.0% |

Physical properties of the composition were as follows:
$T_{N1}$=92.1° C.
η=39.1 mPa.s
Δn1=0.189
Δε1=7.1
$V_{th}$=2.19 V

COMPOSITION EXAMPLE 29

A liquid crystal composition containing the following compounds was prepared.

| | |
|---|---|
| 3-DB (F) EB (F) —F (No. 43) | 4.0% |
| 3-DB (F, F) B (F) —CF3 (No. 29) | 3.0% |
| 3-DB (F, F) BB (F, F) —F (No. 143) | 3.0% |
| 3-DB—C | 10.0% |
| 4-DB—C | 5.0% |
| 2-BEB—C | 7.0% |
| 3-BEB—C | 4.0% |
| 3-PyB (F) —F | 6.0% |
| 3-HEB-O4 | 8.0% |
| 4-HEB-O2 | 6.0% |
| 5-HEB-O1 | 6.0% |
| 3-HEB-O2 | 5.0% |
| 5-HEB-O2 | 4.0% |
| 5-HEB-5 | 5.0% |
| 4-HEB-5 | 5.0% |
| 1O-BEB-2 | 4.0% |
| 3-HHB-1 | 6.0% |
| 3-HHEBB—C | 3.0% |
| 3-HBEBB—C | 3.0% |
| 5-HBEBB—C | 3.0% |

Physical properties of the composition were as follows:
$T_{N1}$=73.3° C.
η=43.5 mPa.s
Δn1=0.119
Δε1=11.7
$V_{th}$=1.28

COMPOSITION EXAMPLE 30

A liquid crystal composition containing the following compounds was prepared.

| | |
|---|---|
| 3-DB (F, F) B (F) —CF3 (No. 29) | 3.0% |
| 5-BEB (F) —C | 5.0% |
| V-HB—C | 8.0% |
| 5-PyB—C | 6.0% |
| 4-BB-3 | 11.0% |
| 3-HH-2V | 10.0% |
| 5-HH—V | 11.0% |
| V-HHB-1 | 7.0% |
| V2-HHB-1 | 15.0% |
| 3-HHB-1 | 9.0% |
| 1V2-HBB-2 | 10.0% |
| 3-HHEBH-3 | 5.0% |

Physical properties of the composition were as follows:
$T_{N1}$=91.1° C.
η=17.2 mPa.s
Δn1=0.115
Δε1=5.2
$V_{th}$=2.31 V

COMPOSITION EXAMPLE 31

A liquid crystal composition containing the following compounds was prepared.

| | |
|---|---|
| 3-DB (F, F) B (F) —CF3 (No. 29) | 4.0% |
| 3-DB (F, F) BB (F, F) —F (No. 143) | 4.0% |
| 2O1-BEB (F) —C | 5.0% |
| 3O1-BEB (F) —C | 7.0% |
| 5O1-BEB (F) —C | 4.0% |
| 1V2-BEB (F, F) —C | 16.0% |
| 3-HB-O2 | 10.0% |
| 3-HH-4 | 3.0% |
| 3-HHB—F | 3.0% |
| 3-HHB-1 | 8.0% |

-continued

| | |
|---|---|
| 3-HHB-O1 | 4.0% |
| 3-HBEB—F | 4.0% |
| 3-HHEB—F | 7.0% |
| 5-HHEB—F | 4.0% |
| 3-H2BTB-2 | 4.0% |
| 3-H2BTB-3 | 4.0% |
| 3-H2BTB-4 | 4.0% |
| 3-HB (F) TB-2 | 5.0% |

Physical properties of the composition were as follows:
$T_{N1}$=97.5° C.
$\eta$=31.1 mPa.s
$\Delta n1$=0.093
$\Delta\epsilon1$=7.2
$V_{th}$=2.01 V

COMPOSITION EXAMPLE 32

A liquid crystal composition containing the following compounds was prepared.

| | |
|---|---|
| 3-DB (F, F) B (F) —CF3 (No. 29) | 5.0% |
| 3-DB (F, F) BB (F, F) —F (No. 143) | 5.0% |
| 2-HHB (F) —F | 17.0% |
| 3-HHB (F) —F | 17.0% |
| 5-HHB (F) —F | 16.0% |
| 2-H2HB (F) —F | 10.0% |
| 3-H2HB (F) —F | 5.0% |
| 5-H2HB (F) —F | 10.0% |
| 2-HBB (F) —F | 6.0% |
| 5-HBB (F) —F | 9.0% |

Physical properties of the composition were as follows:
$T_{N1}$=97.5° C.
$\eta$=31.1 mPa.s
$\Delta n1$=0.093
$\Delta\epsilon1$=7.2
$V_{th}$=2.01 V

COMPOSITION EXAMPLE 33

A liquid crystal composition containing the following compounds was prepared.

| | |
|---|---|
| 3-DB (F) EB (F) —F (No. 29) | 5.0% |
| 3-DB (F, F) BB (F, F) —F (No. 143) | 5.0% |
| 7-HB (F) —F | 5.0% |
| 5-H2B (F) —F | 5.0% |
| 3-HB—O2 | 10.0% |
| 3-HH-4 | 5.0% |
| 2-HHB (F) —F | 10.0% |
| 3-HHB (F) —F | 10.0% |
| 3-H2HB (F) —F | 5.0% |
| 2-HBB (F) —F | 3.0% |
| 3-HBB (F) —F | 3.0% |
| 5-HBB (F) —F | 6.0% |
| 2-H2BB(F) —F | 5.0% |
| 3-H2BB (F) —F | 6.0% |
| 3-HHB-1 | 8.0% |
| 3-HHB—O1 | 5.10% |
| 3-RHB-3 | 4.0% |

Physical properties of the composition were as follows:
$T_{N1}$=86.5° C.
$\eta$=23.5 mPa.s
$\Delta n1$=0.099
$\Delta\epsilon1$=5.3
$V_{th}$=2.18 V

COMPOSITION EXAMPLE 34

A liquid crystal composition containing the following compounds was prepared.

| | |
|---|---|
| 3-DB (F, F) B—CL (No. 32) | 5.0% |
| 3-DB (F) B (F, F) —F (No. 4) | 10.0% |
| 3-DB (F) EB (F) —F (No. 43) | 10.0% |
| 3-DB (F, F) BB (F, F) —F (No. 143) | 5.0% |
| 7-HB (F, F) —F | 4.0% |
| 3-H2HB (F, F) —F | 12.0% |
| 4-H2HB (F, F) —F | 10.0% |
| 3-HHB (F, F) —F | 10.0% |
| 3-HH2B (F, F) —F | 15.0% |
| 3-HBB (F, F) —F | 7.0% |
| 5-HBB (V, F) —F | 12.0% |

Physical properties of the composition were as follows:
$T_{N1}$=66.4° C.
$\eta$=36.1 mPa.s
$\Delta n1$=0.091
$\Delta\epsilon1$=12.6
$V_{th}$=1.42 V

COMPOSITION EXAMPLE 35

A liquid crystal composition containing the following compounds was prepared.

| | |
|---|---|
| 3-DB (F, F) B (F) —F (No. 23) | 5.0% |
| 3-DB (F) EB (E) —F (No. 43) | 5.0% |
| 3-DB (F, F) BB (F, F) —F (No. 143) | 5.0% |
| 7-HB (F, F) —F | 5.0% |
| 3-H2HB (F, F) —F | 12.0% |
| 4-H2HB (F, F) —F | 10.0% |
| 3-HHB (F, F) —F | 10.0% |
| 4-HHB (F, F) —F | 5.0% |
| 3-HBB (F, F) —F | 10.0% |
| 8-HHEB (F, F) —F | 8.0% |
| 4-HHEB (F, F) —F | 3.0% |
| 5-HHEB (F, F) —F | 3.0% |
| 3-HBEB (F, F) —F | 5.0% |
| 5-HBEB (F, F) —F | 3.0% |
| 3-HDB (F, F) —F | 5.0% |
| 3-HHBB (F, F) —F | 6.0% |

Physical properties of the composition were as follows:
$T_{N1}$=78.0° C.
$\eta$=39.2 mPa.s
$\Delta n1$=0.092
$\Delta\epsilon1$=14.5
$V_{th}$=1.34 V

COMPOSITION EXAMPLE 36

A liquid crystal composition containing the following compounds was prepared.

| | |
|---|---|
| 3-DB (F) EB (F) —F (No. 43) | 10.0% |
| 3-DB (F, F) B (F) —CF3 (No. 29) | 5.0% |
| 3-DB (F, F) BB (F, F) —F (No. 143) | 5.0% |
| 2-HHB (F) —F | 2.0% |
| 3-HHB (F) —F | 2.0% |
| 5-HHB (F) —F | 2.0% |
| 2-HBB (F) —F | 6.0% |

| | |
|---|---|
| 3-HBB (F) —F | 6.0% |
| 5-HBB (F) —F | 10.0% |
| 2-H2BB (F) —F | 9.0% |
| 3-H2BB (F) —F | 9.0% |
| 3-HBB (F, F) —F | 5.0% |
| 5-HBB (F, F) —F | 19.0% |
| 1O1-HBBH-4 | 5.0% |
| 1O1-HBBH-5 | 5.0% |

Physical properties of the composition were as follows:

$T_{N1}=103.2°$ C.

$\eta=42.5$ mPa.s $\Delta n1=0.134$ $\Delta\epsilon1=10.8$ $V_{th}=1.78$ V

COMPOSITION EXAMPLE 37

A liquid crystal composition containing the following compounds was prepared.

| | |
|---|---|
| 3-DB (F, F) B (F) —CF3 (No. 29) | 5.0% |
| 5-HDB (F, F) B (F) —OCF3 (No. 196) | 5.0% |
| 3-DB (F) B (F) —OCF2H (No. 281) | 5.0% |
| 3-HHB (F, F) —F | 9.0% |
| 3-H2HB (F, F) —F | 8.0% |
| 4-H2HB (F, F) —F | 8.0% |
| 5-H2HB (F, F) —F | 8.0% |
| 3-HBB (F, F) —F | 21.0% |
| 5-HBB (F, F) —F | 5.0% |
| 3-H2BB (F, F) —F | 10.0% |
| 5-HHBB (F, F) —F | 3.0% |
| 3-HH2BB (F, F) —F | 3.0% |
| 5-HHEBB—F | 2.0% |
| 1O1-HBBH-4 | 4.0% |
| 1O1-HBBH-5 | 4.0% |

COMPOSITION EXAMPLE 38

A liquid crystal composition containing the following compounds was prepared.

| | |
|---|---|
| 3-DB (F) EB (F) —F (No. 43) | 4.0% |
| 3-DB (F) B (F) —OCF2H (No. 281) | 3.0% |
| 3-DB (F, F) B—OCF2CFHCF3 (No. 38) | 3.0% |
| 5-DB (F) B (F, F) EB (F) —CF3 (No. 233) | 2.0% |
| 5-HB—F | 12.0% |
| 6-HB—F | 9.0% |
| 7-HB—F | 7.0% |
| 2-HHB—OCF3 | 7.0% |
| 3-HHB—OCF3 | 9.0% |
| 4-HHB—OCF3 | 7.0% |
| 5-HHB—OCF3 | 5.0% |
| 3-HH2B—OCF3 | 4.0% |
| 5-HH2B—OCF3 | 4.0% |
| 3-HHB (F, F) —OCF3 | 5.0% |
| 5-HBB (F) —F | 10.0% |
| 3-HH2B (F) —F | 3.0% |
| 3-HB (F) BH-3 | 3.0% |
| 5-HBBH-3 | 3.0% |

COMPOSITION EXAMPLE 39

A liquid crystal composition containing the following compounds was prepared.

| | |
|---|---|
| 3-DB (F, Cl) B (F) —OCF3 (No. 331) | 3.0% |
| 3-DB (F, F) B (F) —OCF3 (No. 26) | 3.0% |
| 2-HHB (F) —F | 17.0% |
| 3-HHB (F) —F | 17.0% |
| 5-HHB (F) —F | 16.0% |
| 2-H2HB (F) —F | 10.0% |
| 3-H2HB (F) —F | 5.0% |
| 5-H2HB (F) —F | 10.0% |
| 2-HBB (F) —F | 6.0% |
| 5-HBB (F) —F | 13.0% |

COMPOSITION EXAMPLE 40

A liquid crystal composition containing the following compounds was prepared.

| | |
|---|---|
| 3-DB (F, F) B (F) —F (No. 23) | 3.0% |
| 3-DB (F, F) B (F —OCF3 (No. 26) | 3.0% |
| 2-HHB (F) —F | 17.0% |
| 3-HHB (F) —F | 16.5% |
| 5-HHB (F) —F | 16.0% |
| 2-H2HB (F) —F | 10.0% |
| 3-H2HB (F) —F | 5.0% |
| 5-H2HB (F) —F | 10.0% |
| 2-HBB (F) —F | 6.0% |
| 5-HBB (F) —F | 13.0% |

Optically-active compound of the aforementioned formula (Op-4)

Physical properties of the composition were as follows:

$T_{N1}=97.6°$ C.

$\eta=26.7$ mPa.s $\Delta n1=0.095$ $\Delta\epsilon1=6.1$ $V_{th}=2.04$ V

Pitch=14 $\mu$m

COMPOSITION EXAMPLE 41

A liquid crystal composition containing the following compounds was prepared.

| | |
|---|---|
| 3-DB (F, F) EB (F) —F (No. 63) | 15.0% |
| 3-HB—C | 20.0% |
| 5-HB—C | 31.0% |
| 7-HB—C | 21.0% |
| 5-HBB—C | 13.0% |

Physical properties of the composition were as follows:

$T_{N1}=67.6°$ C.

$\eta=31.4$ mPa.s $\Delta n1=0.130$ $\Delta\epsilon1=13.6$ $V_{th}=1.38$ V

COMPOSITION EXAMPLE 42

A liquid crystal composition containing the following compounds was prepared.

| | |
|---|---|
| 3-DB (F, F) EB (F) —F (No. 63) | 6.0% |
| 3-DB (F, F) B (F) —CF3 (No. 29) | 4.0% |
| 1V2-BEB (F, F) —C | 5.0% |
| 3-HB—C | 25.0% |

-continued

| | |
|---|---|
| 1-BTB-3 | 5.0% |
| 2-BTB-1 | 5.0% |
| 3-HH-4 | 6.0% |
| 3-HHB-1 | 11.0% |
| 3-HHB-3 | 9.0% |
| 3-H2BTB-2 | 4.0% |
| 3-H2BTB-3 | 4.0% |
| 3-H2BTB-4 | 4.0% |
| 3-HB (F) TB-2 | 6.0% |
| 3-HB (F) TB-3 | 6.0% |

Physical properties of the composition were as follows:
$T_{N1}$=91.5° C.
$\eta$=21.6 mPa.s
$\Delta n1$=0.161
$\Delta \epsilon 1$=10.4
$V_{th}$=1.79 V

COMPOSITION EXAMPLE 43

A liquid crystal composition containing the following compounds was prepared.

| | |
|---|---|
| 3-DB (F, F) EB (F) —F (No. 63) | 4.0% |
| 3-DB (F, F) BB (F, F) —F (No. 143) | 4.0% |
| 2O1-BEB (F) —C | 5.0% |
| 3O1-BEB (F) —C | 7.0% |
| 5O1-BEB (F) —C | 4.0% |
| 1V2-BEB (F, F) —C | 16.0% |
| 3-HB-O2 | 10.0% |
| 3-HH-4 | 3.0% |
| 3-HHB—F | 3.0% |
| 3-HHB-1 | 8.0% |
| 3-HHB—O1 | 4.0% |
| 3-HBEB—F | 4.0% |
| 3-HHEB—F | 7.0% |
| 5-HHEB—F | 4.0% |
| 3-H2BTB-2 | 4.0% |
| 3-H2BTB-3 | 4.0% |
| 3-H2BTB-4 | 4.0% |
| 3-HB (F) TB-2 | 5.0% |

Physical properties of the composition were as follows:
$T_{N1}$=93.0° C.
$\eta$=42.7 mPa.s
$\Delta n1$=0.144
$\Delta \epsilon 1$=27.8
$V_{th}$=1.03 V

COMPOSITION EXAMPLE 44

A liquid crystal composition containing the following compounds was prepared.

| | |
|---|---|
| 3-DB (F, F) EB (F) —F (No. 63) | 5.0% |
| 3-DB (F, F) BB (F, F) —F (No. 143) | 5.0% |
| 2-HHB (F) —F | 17.0% |
| 3-HHB (F) —F | 17.0% |
| 5-HHB (F) —F | 16.0% |
| 2-H2HB (F) —F | 10.0% |
| 3-H2HB (F) —F | 5.0% |
| 5-H2HB (F) —F | 10.0% |
| 2-HBB (F) —F | 6.0% |
| 3-HBB (F) —F | 6.0% |
| 5-HBB (F) —F | 3.0% |

Physical properties of the composition were as follows:
$T_{N1}$=98.1° C.
$\eta$=29.9 mPa.s
$\Delta n1$=0.093
$\Delta \epsilon 1$=6.5
$V_{th}$=2.08 V

COMPOSITION EXAMPLE 45

A liquid crystal composition containing the following compounds was prepared.

| | |
|---|---|
| 3-DB (F, F) EB (F) —F (No. 63) | 10.0% |
| 3-HB—CL | 10.0% |
| 5-HB—CL | 4.0% |
| 7-HB—CL | 4.0% |
| 1O1-HH—5 | 5.0% |
| 3-HBB (F) —F | 6.0% |
| 5-HBB (F) —F | 14.0% |
| 4-HHB—CL | 8.0% |
| 5-HHB—CL | 8.0% |
| 3-H2HB (F) —CL | 4.0% |
| 3-HBB (F, F) —F | 10.0% |
| 5-H2BB (F, F) —F | 9.0% |
| 3-HB (F) VB—2 | 4.0% |
| 3-HB (F) VB-3 | 4.0% |

Physical properties of the composition were as follows:
$T_{N1}$=92.7° C.
$\eta$=23.2 mPa.s
$\Delta n1$=0.120
$\Delta \epsilon 1$=6.5
$V_{th}$=2.04 V

COMPOSITION EXAMPLE 46

A liquid crystal composition containing the following compounds was prepared.

| | |
|---|---|
| 3-DB (F, F) EB (F) —F (No. 63) | 10.0% |
| 3-DB (F, F) B (F) —OCF3 (No. 26) | 5.0% |
| 3-H2HB (F, F) —F | 7.0% |
| 5-H2HB (F, F) —F | 8.0% |
| 3-HHB (F, F) —F | 10.0% |
| 4-HHB (F, F) —F | 5.0% |
| 3-HH2B (F, F) —F | 9.0% |
| 5-HH2B (F, F) —F | 9.0% |
| 3-HBB (F, F) —F | 15.0% |
| 3-HBEB (F, F) —F | 2.0% |
| 4-HBEB (F, F) —F | 2.0% |
| 5-HBEB (F, F) —F | 2.0% |
| 3-HHEB (F, F) —F | 10.0% |
| 4-HHEB (F, F) —F | 3.0% |
| 5-HHEB (F, F) —F | 3.0% |

Physical properties of the composition were as follows:
$T_{N1}$=77.9° C.
$\eta$=34.6 mPa.s
$\Delta n1$=0.089
$\Delta \epsilon 1$=13.8
$V_{th}$=1.54 V The compounds expressed by formula (1) of the present invention may be easily prepared through methods described by literature; for example, Experimental Chemistry (4th ed., Maruzen Co., Ltd.), J. Org. Chem., 42, 1821 (1977), and J. Chem. Soc. Perkin Trans. 2, 2041 (1989).

Synthesis of a compound of formula (1-a) (which corresponds to formula (1) in which n1=n2=0) wherein Za is a single bond A benzaldehyde derivative (19) is reacted with 2-alkyl-1,3-propanediol (18) in the presence of an acid catalyst, to thereby obtain a phenyldioxane derivative (20). Butyl lithium is reacted with the derivative (20) at about −50° C., to thereby obtain a lithiated compound (21). The butyl lithium is preferably sec-butyl lithium or t-butyl lithium in the case where the phenyldioxane derivative (20) is a monofluoro derivative ((F)=H), and preferably n-butyl lithium in the case where the derivative (20) is a difluoro derivative ((F)=F).

The thus-obtained lithiated compound (21) is subsequently subjected to a known process for synthesizing a homobiaryl derivative. This can be generally performed by either one of the following two methods.

The first is a method described in J. Org. Chem., 42, 1821 (1977). When this method is used and lithiated compound (21) is sequentially reacted with zinc chloride, Pd(0), and a compound (22), the target compound (24) can be obtained.

The other is a method described in J. Chem. Soc. Perkin Trans. 2, 2041 (1989). Based on this method, a compound obtained by iodinating a lithiated compound (21) and a boronic acid derivative (23)—which is obtained from the reaction between trialkyl borate and a Grignard reagent prepared from the compound (22)—is subjected to a coupling reaction in the presence of a catalyst such as Pd(0), to thereby obtain the target compound (24):

wherein R, $Q_5$, $Q_6$, and Y have the same meanings as described above.

Synthesis of a compound of formula (1-a) in which Za is —COO—

A carboxylic acid derivative (25) is obtained by reacting $CO_2$ with the lithiated compound (21) in accordance with the method described in page 16 of Experimental Chemistry, Vol. 22 (4th ed., Maruzen Co., Ltd.). The derivative (25) is allowed to react with a phenol derivative (26) in the presence of 4-dimethylaminopyridine and 1,3-dicyclohexylcarbodiimide (hereinafter referred to as DCC), to thereby obtain an ester (27) of the target compound.

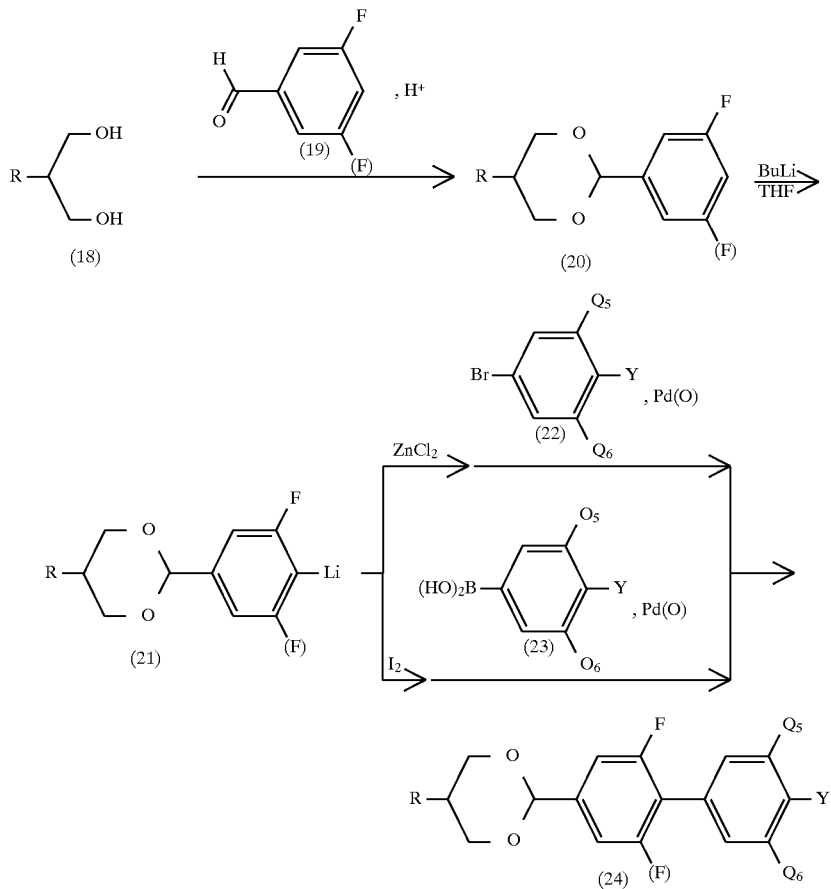

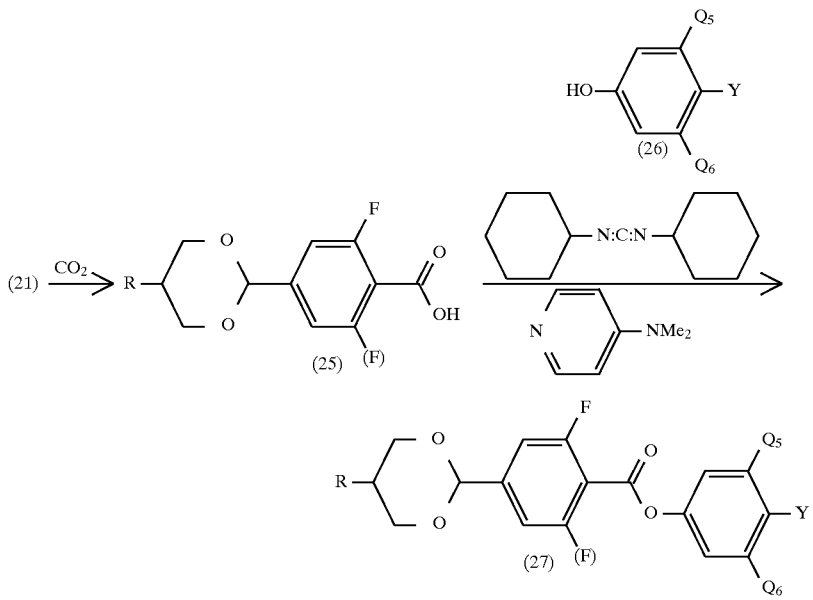

Synthesis of a compound of formula (1-a) in which Za is —$CF_2O$—

In accordance with the method described in Bull. Soc. Chim. Belg., 87, 293 (1978), the above-described ester (27) is reacted with a Lawson reagent to thereby obtain a thione ester (28). When the ester (28) was reacted with diethylaminosulfur trifluoride (hereinafter abbreviated as DAST) in methylene chloride or a glyme solvent, or in accordance with the method described in Japanese Patent Application Laid-Open (kokai) No. 6-263679, reacted with dihydrotrifluorotetrabutyl ammonium (hereinafter abbreviated as TBAH2F3) and N-iodosuccinic imide (hereinafter abbreviated as NIS) in methylene chloride or 1,2-dichloro-ethane, the target compound, difluoromethyl ether (29), can be obtained.

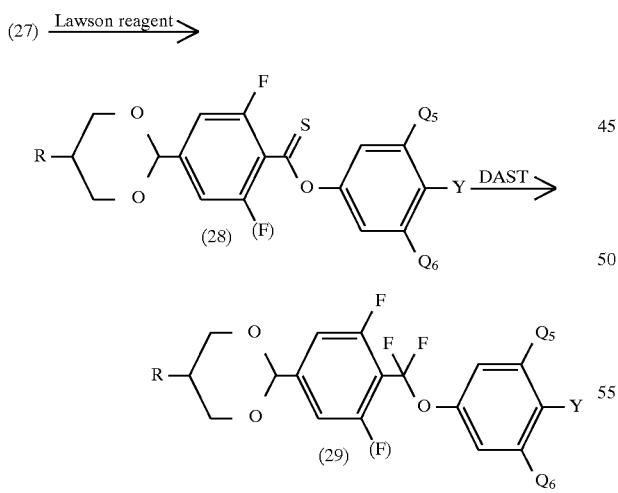

Synthesis of a compound of formula (1-b) (which corresponds to formula (1) in which n1=0, and n2=1))

This compound can be obtained by performing the process for synthesizing the aforementioned compound (1-a) excepting that a compound (24), ester (27), or difluoromethyl ether (29), in any one of which Y is a hydrogen atom, is used in place of the phenyldioxane derivative (20).

Synthesis of a compound of formula (1-c) (which corresponds to formula (1) in which n1=1, and n2=0))

First, a compound (30) is sequentially reacted with lithium diisopropylamide (hereinafter abbreviated as LDA) and methyl chlorocarbonate to thereby obtain a compound (31). When the compound (31) is reacted with lithium aluminum hydride (hereinafter abbreviated as LAH), 1,3-propanediol derivative (32) can be obtained.

Subsequently, a method similar to that described for the synthesis of the aforementioned compound (24), ester (27), or difluoroether (29) is repeated excepting that the 1,3-propanediol derivative (32) is used in place of the aforementioned compound (18), to thereby obtain the target compound (1-c).

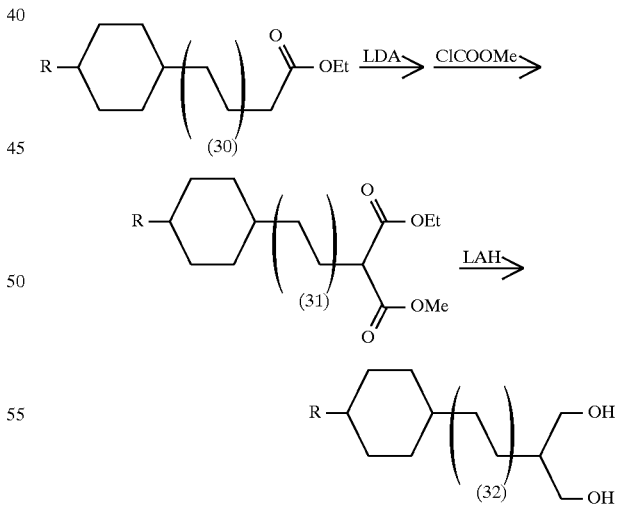

Hereinabove, general processes are described. In order to prepare specific compounds such as those of formulas (1-a) and (1-c) in which $Q_3$ is a fluorine atom and $Q_4$ is a hydrogen atom, or compounds of formula (1-b) in which $Q_1$ is a fluorine atom and $Q_2$ is a hydrogen atom, the following synthesis methods are particularly suitable, which, needless to say, may also be used for the manufacture of other compounds.

Briefly, a compound (33) is subjected to a coupling reaction with a boric acid derivative (23) in the presence of a catalyst such as Pd(0) to thereby obtain a compound (34), which is reacted with butyl lithium. Subsequently, piperidine-1-carboaldehyde, dimethylformamide, or a similar substance is reacted to obtain a compound (35). When the above method for the synthesis of compound (20) from compounds (18) and (19) is repeated through use of this compound in place of compound (19), the target compound (36) can be obtained. In this case, if compound (32) is used instead of compound (18), another target compound (37) can be obtained.

resultant compound, to thereby obtain a carboxylic acid (38). Through use of the carboxylic acid (38) instead of compound (25), the method for the synthesis of compound (27) is repeated, or alternatively, the carboxylic acid (38) is allowed to react with the phenol derivative (26) in the presence of concentrated sulfuric acid, to thereby obtain a compound (39) (see page 44 of Experimental Chemistry, Vol. 22 (4th ed., Maruzen Co., Ltd.)). The compound (39) is used instead of compound (34) in a method similar to that described for the synthesis of compound (35), to obtain the target compound (40), and then this compound (40) is used instead of compound (35) in a method similar to that

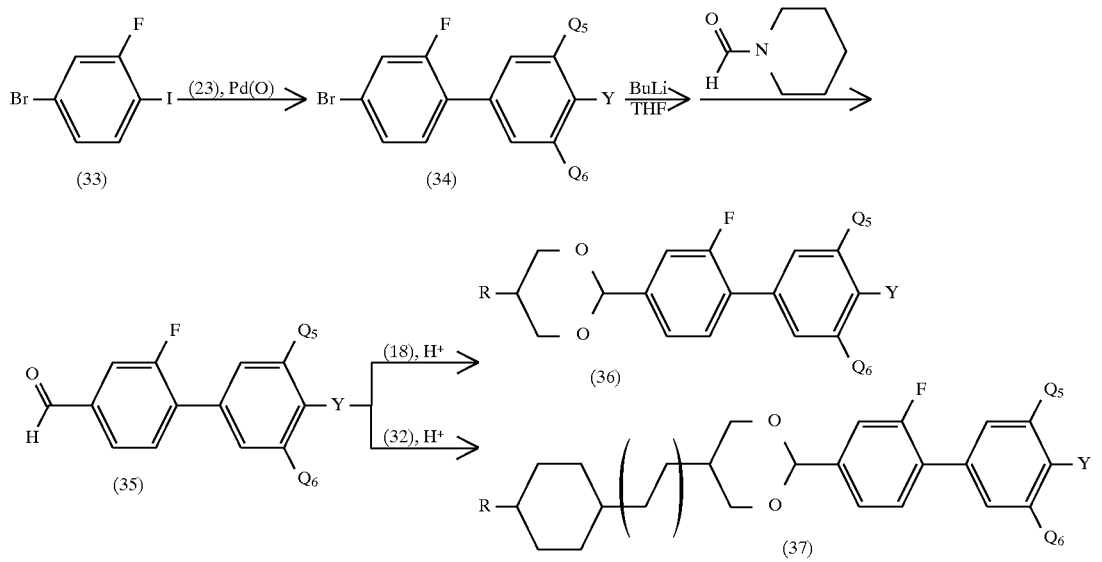

Also, a target compound (40) can be obtained by performing the following process. That is, a compound (33) is reacted with butyl lithium, and $CO_2$ is reacted with the described for the synthesis of compound (36) or (37), to thereby obtain the target compounds (41) and (42).

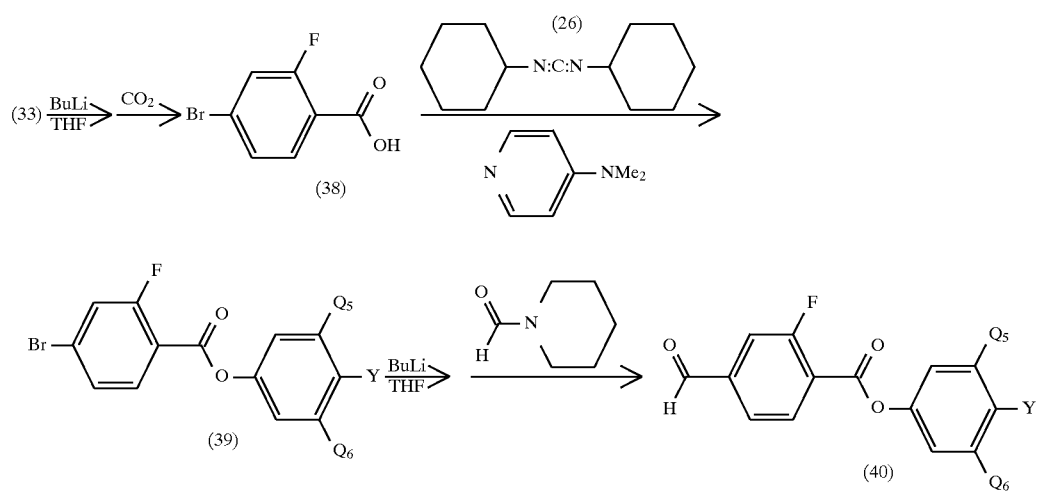

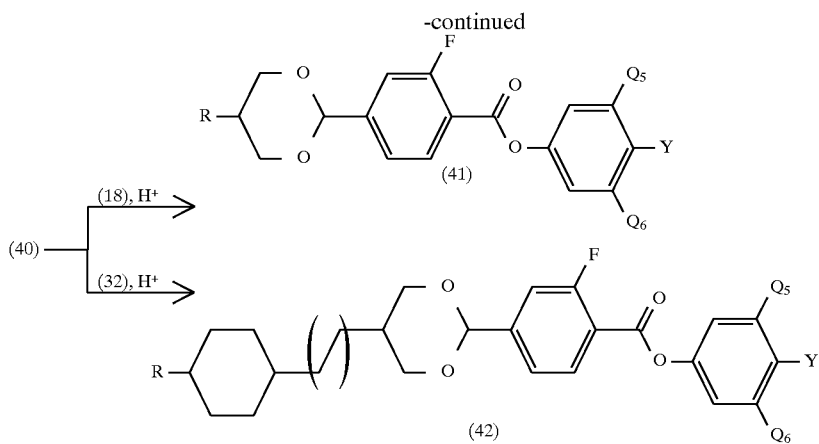

Independently, in a manner similar to that described for the synthesis of compound (29), excepting that compound (39) is used instead of compound (27), a compound (44) is obtained. Through use of compound (44) instead of compound (34), the methods for the synthesis of compounds (36) and (37) are repeated, to thereby obtain compounds (45) and (46).

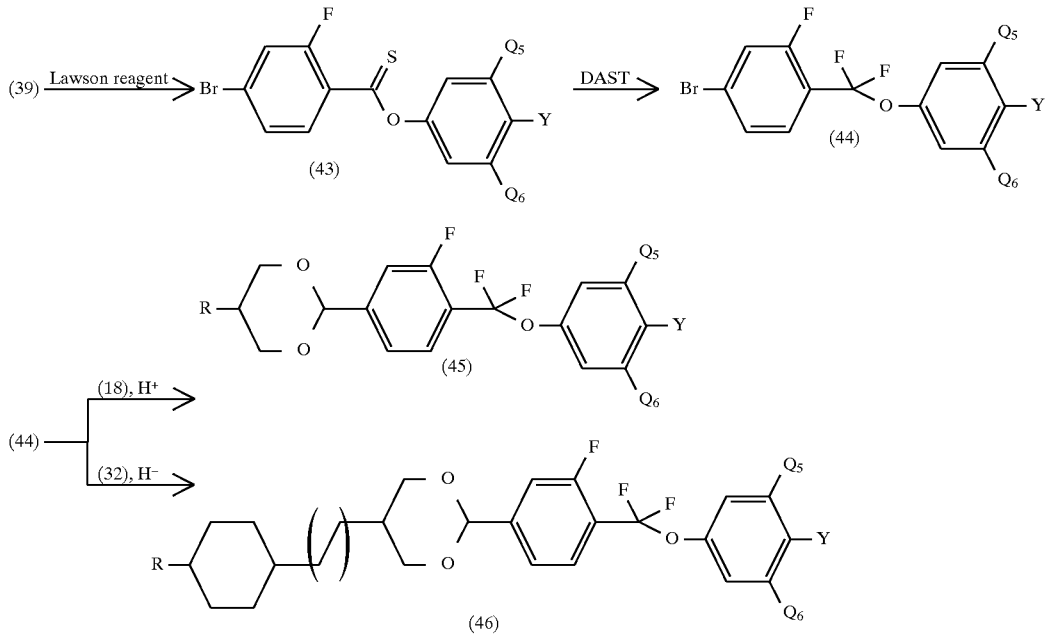

wherein R has the same meaning as described above.

EXAMPLES

The present invention will next be described in more detail by way of examples, which should not be construed as limiting the invention.

In the Examples, C, S, N, and I respectively represent crystal, smectic phase, nematic phase, and isotropic liquid phase.

Example 1

Preparation of 5-propyl-2-(4-(3,4-difluorophenyl)-3,5-difluorophenyl)-1,3-dioxane (Compound No. 23; which is a compound of formula (1), wherein R is n-propyl, $n1=n2=0$, Za is a single bond, each of $Q_3$, $Q_4$, and $Q_5$ is a fluorine atom, $Q_6$ is a hydrogen atom, and Y is a fluorine atom):

Step 1

2-Propyl-1,3-propanediol (83.2 g; 704 mmol) and 3,5-difluorobenzaldehyde (100 g; 704 mmol) were dissolved in toluene (1 liter), and p-toluenesulfonic acid (hereinafter referred to as PTS; 5 g) was added. The mixture was refluxed for 3 hours while being dehydrated with a Dean-Stark's device. The resultant reaction mixture was washed sequentially with saturated sodium bicarbonate solution and saturated brine and dried over magnesium sulfate. Subsequently, the solvent was evaporated. The residue was recrystallized twice from heptane, to thereby obtain 82.0 g (338 mmol) of 5-propyl-2-(3,5-difluorophenyl)-1,3-dioxane. The yield of the compound from 3,5-difluorobenzaldehyde was 48.0%.

Step 2

The product of Step 1 (5.0 g; 20.6 mmol) was dissolved in tetrahydrofuran (hereinafter referred to as THF; 50 ml), and the solution was cooled to −60° C. in a nitrogen atmosphere. A solution (16.1 ml; 25.8 mmol) of 1.60M n-butyl lithium in hexane was added dropwise thereto so that the temperature of the mixture did not exceed –55° C. The mixture was stirred for 1 hour with the temperature being maintained below –55° C. Subsequently, a solution (51.6 ml; 25.8 mmol) of 0.5M zinc chloride in THF was added dropwise so that the temperature of the mixture did not exceed –55° C. Thereafter, the mixture was warmed to room temperature and stirred for 30 minutes. Tetrakistriphenylphosphine palladium (0.5 g) and 1-bromo-3,4-difluorobenzene (4.98 g; 25.8 mmol) were added, and the mixture was refluxed for 3.5 hours. Water (100 ml) was added to the resultant reaction mixture, and the material produced was extracted with toluene. The extract was sequentially washed with 3 N-HCl saturated sodium bicarbonate solution, and saturated brine, and then dried over magnesium sulfate. Subsequently, the solvent was evaporated. The residue was purified by column chromatography (eluent: heptane/ethyl acetate=5/1). The solvent was evaporated, and the residue was recrystallized twice from heptane, to thereby obtain 1.18 g (3.33 mmol) of 5-propyl-2-(4-(3,4-difluorophenyl)-3,5-difluorophenyl)-1,3-dioxane. The yield of this compound from 5-propyl-2-(3,5-difluorophenyl)-1,3-dioxane was 16.2%.

1H-NMR (CDCl3) δ(ppm): 7.39~7.05 (m, 5H), 5.39 (s, 1H), 4.34~4.16 (m, 2H), 3.66~3.40 (m, 2H), 2.26~2.07 (m, 1H), 1.56~0.85 (m, 7H)

C-I 72.5° C.

Example 2

Preparation of 5-propyl-2-(4-(3,4,5-trifluorophenyl)-3-fluorophenyl)-1,3-dioxane (Compound No. 4; which is a compound of formula (1), wherein R is n-propyl, n1=n2=0, Za is a single bond, each of $Q_3$, $Q_5$, and $Q_6$ is a fluorine atom, $Q_4$ is a hydrogen atom, and Y is a fluorine atom):

Step 1

2-Propyl-1,3-propanediol (138.0 g; 1.17 mol) and 3-fluorobenzaldehyde (138.0 g; 1.11 mol) were dissolved in toluene (1.5 liters), and PTS (7 g) was added. The mixture was refluxed for 3 hours while being dehydrated with a Dean-Stark's device. The resultant reaction mixture was washed sequentially with saturated sodium bicarbonate solution and saturated brine, and then dried over magnesium sulfate. Subsequently, the solvent was evaporated. The residue was recrystallized twice from heptane, to thereby obtain 81.2 g (362 mmol) of 5-propyl-2-(3-fluorophenyl)-1,3-dioxane. The yield of the compound from 3-fluorobenzaldehyde was 32.6%.

Step 2

The product of Step 1 (10.0 g; 44.6 mmol) was dissolved in THF (100 ml), and the solution was cooled to –60° C. in a nitrogen atmosphere. A solution (47.4 ml; 53.6 mmol) of 1.13M s-butyl lithium in hexane was added dropwise thereto so that the temperature of the mixture did not exceed –55° C. The mixture was stirred for 1 hour with the temperature being maintained below –55° C. Subsequently, a solution (107.2 ml; 53.6 mmol) of 0.5M zinc chloride in THF was added dropwise so that the temperature of the mixture did not exceed –55° C. Thereafter, the mixture was warmed to room temperature and stirred for 1 hour. Tetrakis-triphenyl phosphine palladium (1.0 g) and 1-bromo-3,4,5-trifluorobenze ne (11.3 g; 53.6 mmol) were added, and the mixture was refluxed for 2.5 hours. Water (200 ml) was added to the resultant reaction mixture, and the material produced was extracted with toluene. The extract was sequentially washed with saturated aqueous ammonium chloride solution, saturated sodium bicarbonate solution, and saturated brine, and then dried over magnesium sulfate.

Subsequently, the solvent was evaporated. The residue was purified by column chromatography (eluent: toluene). The solvent was evaporated, and the residue was recrystallized twice from heptane, to thereby obtain 7.50 g (21.2 mmol) of 5-propyl-2-(4-(3,4,5-trifluorophenyl)-3-fluorophenyl)-1,3-dioxane. The yield of this compound from 5-propyl-2-(3-fluorophenyl)-1,3-dioxane was 47.5%.

1H-NMR (CDCl3) δ(ppm): 7.65~6.96 (m, 5H), 5.05 (s, 1H), 4.24~4.05 (m, 2H), 3.42~3.17 (m, 2H), 2.36~1.93 (m, 1H), 1.56~0.82 (m, 7H)

C-I 83.2° C.

Example 3

Preparation of 5-propyl-2-(4-(4-fluorophenyl)-3,5-difluorophenyl)-1,3-dioxane (Compound No. 22; which is a compound of formula (1), wherein R is n-propyl, n1=n2=0, Za is a single bond, each of $Q_3$ and $Q_4$ is a fluorine atom, each of $Q_5$ and $Q_6$ is a hydrogen atom, and Y is a fluorine atom):

Step 1

5-Propyl-2-(3,5-difluorophenyl)-1,3-dioxane (5.0 g; 20.6 mmol), which had been synthesized in Step 1 of Example 1, was dissolved in THF (50 ml), and the solution was cooled to –60° C. in a nitrogen atmosphere. A solution (16.1 ml; 25.8 mmol) of 1.60M n-butyl lithium in hexane was added dropwise thereto so that the temperature of the mixture did not exceed –55° C. The mixture was stirred for 1 hour with the temperature being maintained below –55° C. Subsequently, a solution (51.6 ml; 25.8 mmol) of 0.5M zinc chloride in THF was added dropwise so that the temperature of the mixture did not exceed –45° C. Thereafter, the mixture was warmed to room temperature and stirred for 30 minutes.

To the resulting solution, tetrakistriphenylphosphine palladium (0.5 g) and 4-fluorobromobenzene (4.51 g; 25.8 mmol) were added, and the mixture was refluxed for 4 hours and 20 minutes. Water (100 ml) was added to the resultant reaction mixture, and the material produced was extracted with toluene. The extract was sequentially washed with 3 N-HCl, saturated sodium bicarbonate solution and saturated brine and dried over magnesium sulfate. Subsequently, the solvent was evaporated. The residue was purified by column chromatography (eluent: toluene). The solvent was evaporated, and the residue was recrystallized twice from heptane, to thereby obtain 3.21 g (9.55 mmol) of 5-propyl-2-(4-(4-fluorophenyl)-3,5-difluorophenyl)-1,3-dioxane. The yield of this compound from 5-propyl-2-(3,5-difluorophenyl)-1,3-dioxane was 46.4%.

1H-NMR (CDCl3) δ(ppm): 7.62~7.13 (m, 6H), 5.49 (s, 1H), 4.44~4.26 (m, 2H), 3.76~3.51 (m, 2H), 2.31~2.17 (m, 1H), 1.52~0.95 (m, 7H)

C-I 87.4° C.

Example 4

Preparation of 5-propyl-2-(4-(3-fluoro-4-trifluoromethoxyphenyl)-3,5-difluorophenyl)-1,3-dioxane (Compound No. 26; which is a compound of formula (1), wherein R is n-propyl, n1=n2=0, Za is a single bond, each of $Q_3$, $Q_4$, and $Q_5$ is a fluorine atom, $Q_6$ is a hydrogen atom, and Y is $OCF_3$):

Step 1

5-Propyl-2-(3,5-difluorophenyl)-1,3-dioxane (5.0 g; 20.6 mmol), which had been synthesized in Step 1 of Example 1, was dissolved in THF (50 ml), and the solution was cooled to –60° C. in a nitrogen atmosphere. A solution (16.1 ml; 25.8 mmol) of 1.60M n-butyl lithium in hexane was added dropwise thereto so that the temperature of the mixture did not exceed −50° C. The mixture was stirred for 1 hour with the temperature being maintained below −50° C. Subsequently, a solution (51.6 ml; 25.8 mmol) of 0.5M zinc chloride in THF was added dropwise so that the temperature of the mixture did not exceed −50° C. Thereafter, the mixture was warmed to room temperature and stirred for 30 minutes.

To the resulting solution, tetrakistriphenylphosphine palladium (0.5 g) and 3-fluoro-4-trifluoromethoxybromobenzene (6.68 g; 25.8 mmol) were added, and the mixture was refluxed for 4 hours and 10 minutes. Water (100 ml) was added to the resultant reaction mixture, and the material produced was extracted with toluene. The extract was sequentially washed with 3 N-HCl, saturated sodium bicarbonate solution and saturated brine and dried over magnesium sulfate. Subsequently, the solvent was evaporated. The residue was purified by column chromatography (eluent: toluene). The solvent was evaporated, and the residue was recrystallized twice from heptane, to thereby obtain 4.57 g (10.9 mmol) of 5-propyl-2-(4-(3-fluoro-4-trifluoromethoxyphenyl)-3,5-difluorophenyl)-1,3-dioxane. The yield of this compound from 5-propyl-2-(3,5-difluorophenyl)-1,3-dioxane was 52.9%.

1H-NMR (CDCl3) δ(ppm): 7.58~7.14 (m, 5H), 5.49 (s, 1H), 4.43~4.26 (m, 2H), 3.75~3.51 (m, 2H), 2.30~2.16 (m, 1H), 1.51~0.95 (m, 7H)

C-S 67.8° C., S-I 71.8° C.

Example 5

Preparation of 5-propyl-2-(4-(3,5-difluoro-4-trifluoromethylphenyl)-3,5-difluorophenyl)-1,3-dioxane (Compound No. 30; which is a compound of formula (1), wherein R is n-propyl, n1=n2=0, Za is a single bond, each of $Q_3$, $Q_4$, $Q_5$, and $Q_6$ is a fluorine atom, and Y is $CF_3$):

Step 1

5-Propyl-2-(3,5-difluorophenyl)-1,3-dioxane (5.0 g; 20.6 mmol), which had been synthesized in Step 1 of Example 1, was dissolved in THF (50 ml), and the solution was cooled to −60° C. in a nitrogen atmosphere. A solution (16.1 ml; 25.8 mmol) of 1.60M n-butyl lithium in hexane was added dropwise thereto so that the temperature of the mixture did not exceed −45° C. The mixture was stirred for 1.5 hours with the temperature being maintained below −45° C. Subsequently, a solution (51.6 ml; 25.8 mmol) of 0.5M zinc chloride in THF was added dropwise so that the temperature, of the mixture did not exceed −50° C. Thereafter, the mixture was warmed to room temperature and stirred for 30 minutes. Tetrakistriphenylphosphine palladium (0.5 g) and 1-bromo-3,5-difluoro-4-trifluoromethylbenzene (6.73 g; 25.8 mmol) were added, and the mixture was refluxed for 2 hours and 20 minutes. Water (100 ml) was added to the resultant reaction mixture, and the material produced was extracted with toluene. The extract was sequentially washed with saturated aqueous ammonium chloride solution, saturated sodium bicarbonate solution, and saturated brine, and then dried over magnesium sulfate. Subsequently, the solvent was evaporated. The residue was purified by column chromatography (eluent: toluene). The solvent was evaporated, and the residue was recrystallized twice from heptane, to thereby obtain 2.1 g (5.0 mmol) of 5-propyl-2-(4-(3,5-difluoro-4-trifluoromethylphenyl)-3,5-difluorophenyl)-1,3-dioxane. The yield of this compound from 5-propyl-2-(3,5-difluorophenyl)-1,3-dioxane was 24.3%.

1H-NMR (CDCl3) δ(ppm): 7.26~7.08 (m, 4H), 5.40 (s, 1H), 4.34~4.16 (m, 2 H), 3.67~3.41 (m, 2H), 2.30~2.02 (m, 1H), 1.54~0.85 (m, 7H)

C-I 125.5° C.

Example 6

Preparation of 5-propyl-2-(4-(4-chlorophenyl)-3,5-difluorophenyl)-1,3-dioxane (Compound No. 32; which is a compound of formula (1), wherein R is n-propyl, n1=n2=0, Za is a single bond, each of $Q_3$ and $Q_4$ is a fluorine atom, each of $Q_5$ and $Q_6$ is a hydrogen atom, and Y is a chlorine atom):

Step 1

5-Propyl-2-(3,5-difluorophenyl)-1,3-dioxane (5.0 g; 20.6 mmol), which had been synthesized in Step 1 of Example 1, was dissolved in THF (50 ml), and the solution was cooled to −60° C. in a nitrogen atmosphere. A solution (16.1 ml; 25.8 mmol) of 1.60M n-butyl lithium in hexane was added dropwise thereto so that the temperature of the mixture did not exceed −55° C. The mixture was stirred for 50 minutes with the temperature being maintained below −55° C. Subsequently, a solution (51.6 ml; 25.8 mmol) of 0.5M zinc chloride in THF was added dropwise so that the temperature of the mixture did not exceed −50° C. Thereafter, the mixture was warmed to room temperature and stirred for 30 minutes. Tetrakistriphenylphosphine palladium (0.5 g) and 1-bromo-4-chlorobenzene (4.94 g; 25.8 mmol) were added, and the mixture was refluxed for 3 hours. Water (100 ml) was added to the resultant reaction mixture, and the material produced was extracted with toluene. The extract was sequentially washed with saturated ammonium chloride solution, saturated sodium bicarbonate solution and saturated brine and dried over magnesium sulfate. Subsequently, the solvent was evaporated. The residue was purified by column chromatography (eluent: toluene). The solvent was evaporated, and the residue was recrystallized twice from heptane, to thereby obtain 4.10 g (11.6 mmol) of 5-propyl-2-(4-(4-chlorophenyl)-3,5-difluorophenyl)-1,3-dioxane. The yield of this compound from 5-propyl-2-(3,5-difluorophenyl)-1,3-dioxane was 56.3%.

1H-NMR (CDCl3) δ(ppm): 7.40~7.09 (m, 6H), 5.39 (s, 1H), 4.34~4.16 (m, 2H), 3.66~3.41 (m, 2H), 2.30~1.96 (m, 1H), 1.54~0.85 (m, 7H)

C-I 102.5° C., (I-N 97.8° C., N-C 75.4° C.)

Example 7

Preparation of 3,4-difluorophenyl 4-(5-propyl-(1,3-dioxane)-2-yl)-2,6-difluorophenylcarboxylate (Compound No. 63; which is a compound of formula (1), wherein R is a propyl, n1=n2=0, Za=—COO—, each of $Q_3$, $Q_4$, and $Q_5$ is a fluorine atom, $Q_6$ is a hydrogen atom, and Y is a fluorine atom):

Step 1

5-Propyl-2-(3,5-difluorophenyl)-1,3-dioxane (20.0 g; 82.6 mmol), which had been synthesized in Step 1 of Example 1, was dissolved in THF (200 ml), and the solution was cooled to −60° C. in a nitrogen atmosphere. A solution (64.5 ml; 103.2 mmol) of 1.60M n-butyl lithium in hexane was added dropwise thereto so that the temperature of the mixture did not exceed −55° C. The mixture was stirred for 1 hour with the temperature being maintained below −55° C. The resultant reaction mixture was added to dry ice (500 g) and shaken for 10 minutes. Water (500 ml) was gradually added thereto, and the mixture was allowed to stand for 12 hours at room temperature. 6 N-HCl (200 ml) was added thereto and the material produced was extracted with ether.

The extract was dried over anhydrous magnesium sulfate. Subsequently, the solvent was evaporated, to thereby obtain 23.5 g (82.1 mmol) of 4-(5-propyl-(1,3-dioxane)-2-yl)-2,6-difluorophenylcarboxylic acid as a colorless solid. The yield of this compound was 99.4%.

Step 2

Methylene chloride (30 ml), 4-(5-propyl-(1,3-dioxane)-2-yl)-2,6-difluorophenylcarboxylic acid (5.4 g; 18.9 mmol) of Step 1, 3,4-difluorophenol (7.5 g; 57.7 mmol), and 4-dimethylaminopyridine (1.83 g; 15.0 mmol) were placed in a 200 ml three neck flask equipped with a calcium chloride tube. The mixture was cooled to 0° C. with stirring. Subsequently, a solution of dicyclohexylcarbodiimide (4.30 g; 20.8 mmol) in methylene chloride (20 ml) was added dropwise thereto over 5 minutes. The mixture was heated to room temperature and stirred for 3 hours with the temperature being maintained at room temperature, followed by filtration. The filtrate was washed with 0.5 N-HCl (100 ml) and filtered again. The filtrate was washed sequentially with saturated sodium bicarbonate solution and water, and then dried over anhydrous magnesium sulfate. The solvent was evaporated under reduced pressure. The residue was purified by column chromatography (eluent: toluene). The solvent was evaporated, and the residue was recrystallized twice from heptane, to thereby obtain 3.19 g (8.01 mmol) of 3,4-difluorophenyl 4-(5-propyl-(1,3-dioxane)-2-yl)-2,6-difluorophenylcarboxylate. The yield of this compound from 4-(5-propyl-(1,3-dioxane)-2-yl)-2,6-difluorophenylcarboxylic acid was 42.4%.

1H-NMR (CDCl3) δ(ppm): 7.37~7.05 (m, 5H), 5.39 (s, 1H), 4.34~4.16 (m, 2H), 3.66~3.40 (m, 2H), 2.31~1.96 (m, 1H), 1.57~0.85, (m, 7H)

C-I 63.6° C., (I-N 53.7° C., N-C 35.3° C.)

Example 8

Preparation of 5-propyl-2-(4-(4-(3,4,5-trifluorophenyl)phenyl)-3,5-difluorophenyl)-1,3-dioxane (Compound No. 143; which is a compound of formula (1), wherein R is a propyl group, n1=0, n2=1, each of Za and Zb is a single bond, each of $Q_1$, $Q_2$, $Q_5$, and $Q_6$ is a fluorine atom, each of $Q_3$ and $Q_4$ is a hydrogen atom, and Y is a fluorine atom):

Step 1

5-Propyl-2-(3,5-difluorophenyl)-1,3-dioxane (5.0 g; 20.6 mmol), which had been synthesized in Step 1 of Example 1, was dissolved in THF (50 ml), and the solution was cooled to −60° C. in a nitrogen atmosphere. A solution (16.1 ml; 25.8 mmol) of 1.60M n-butyl lithium in hexane was added dropwise thereto so that the temperature of the mixture did not exceed −55° C. The mixture was stirred for 50 minutes with the temperature being maintained below −55° C. Subsequently, a solution (51.6 ml; 25.8 mmol) of 0.5M zinc chloride in THF was added dropwise so that the temperature of the mixture did not exceed −50° C. Thereafter, the mixture was warmed to room temperature and stirred for 30 minutes.

To the resulting solution, tetrakistriphenylphosphine palladium (0.5 g) and 1-bromo-4-(3,4,5-trifluorophenyl)benzene (5.60 g; 19.5 mmol) were added, and the mixture was refluxed for 3 hours. Water (100 ml) was added to the resultant reaction mixture, and the material produced was extracted with toluene. The extract was sequentially washed with saturated aqueous ammonium chloride solution, satu-rated sodium bicarbonate solution, and saturated brine, and then dried over magnesium sulfate. Subsequently, the solvent was evaporated. The residue was purified by column chromatography (eluent: toluene). The solvent was evaporated, and the residue was recrystallized twice from heptane, to thereby obtain 3.50 g (7.81 mmol) of 5-propyl-2-(4-(4-(3,4,5-trifluorophenyl)phenyl)-3,5-difluorophenyl)-1,3-dioxane. The yield of this compound from 5-propyl-2-(3-(3,5-difluorophenyl)-1,3-dioxane was 40.1%.

1H-NMR (CDCl3) δ(ppm): 7.56 (s, 4H), 7.31~7.12 (m, 4H), 5.41 (s, 1H), 4.36~4.17 (m, 2H), 3.66~3.41 (m, 2H), 2.30~1.96 (m, 1H), 1.55~0.94 (m, 7H)

C-N 154.2° C., N-I 169.2° C.

Example 9

Preparation of 5-propyl-2-(4-(3-fluoro-4-trifluoromethylphenyl)-3,5-difluorophenyl)-1,3-dioxane (Compound No. 29; which is a compound of formula (1), wherein R is a propyl group, n1=n2=0, each of Za and Zb is a single bond, each of $Q_3$, $Q_4$, and $Q_5$ is a fluorine atom, $Q_6$ is a hydrogen atom, and Y is a trifluoromethyl group):

Step 1

5-Propyl-2-(3,5-difluorophenyl)-1,3-dioxane (5.0 g; 20.6 mmol), which had been synthesized in Step 1 of Example 1, was dissolved in THF (50 ml), and the solution was cooled to −60° C. in a nitrogen atmosphere. A solution (15.4 ml; 25.9 mmol) of 1.68M n-butyl lithium in hexane was added dropwise thereto so that the temperature of the mixture did not exceed −55° C. The mixture was stirred for 50 minutes with the temperature being maintained below −55° C. Subsequently, a solution (51.6 ml; 25.8 mmol) of 0.5M zinc chloride in THF was added dropwise so that the temperature of the mixture did not exceed −50° C. Thereafter, the mixture was warmed to room temperature and stirred for 30 minutes.

To the resulting solution, tetrakistriphenylphosphine palladium (0.5 g) and 1-bromo-3-fluoro-4-trifluoromethylbenzene (6.27 g; 25.8 mmol) were added, and the mixture was refluxed for 3 hours. Water (100 ml) was added to the resultant reaction mixture, and the material produced was extracted with toluene. The extract was sequentially washed with saturated ammonium chloride solution, saturated sodium bicarbonate solution and saturated brine and dried over magnesium sulfate. Subsequently, the solvent was evaporated. The residue was purified by column chromatography (eluent: toluene). The solvent was evaporated, and the residue was recrystallized twice from ethanol, to thereby obtain 4.36 g (10.8 mmol) of 5-propyl-2-(4-(3-fluoro-4-trifluoromethylphenyl)-3,5-difluorophenyl)-1,3-dioxane. The yield of this compound from 5-propyl-2-(3,5-difluorophenyl)-1,3-dioxane was 52.4%.

1H-NMR (CDCl3) δ(ppm): 7.76~7.59 (m, 2H), 7.38~7.08 (m, 3H), 5.40 (s, 1H), 4.34~4.16 (m, 2H), 3.66~3.41 (m, 2H), 2.35~1.97 (m, 1H), 1.50~0.93 (m, 7H)

C-I 96.4° C.

Based on the descriptions in Examples 1–9 and DESCRIPTION OF PREFERRED EMBODIMENTS, the following compounds Nos. 1–350 are prepared. The following formulas include those of the compounds obtained in Examples 1–9.

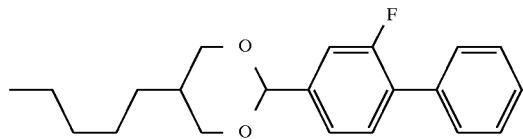  No. 1
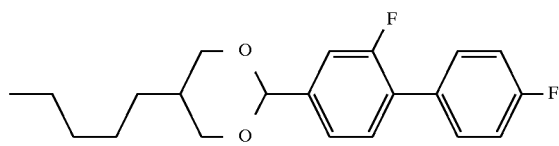  No. 2
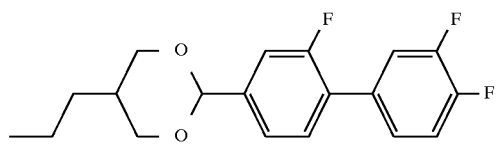  No. 3
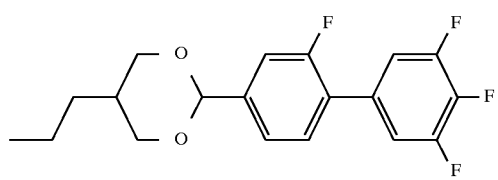  No. 4
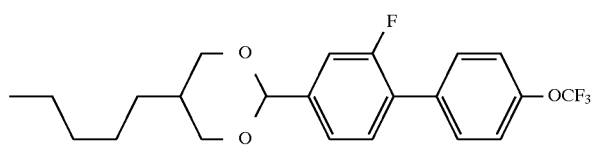  No. 5
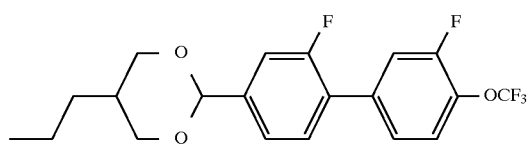  No. 6
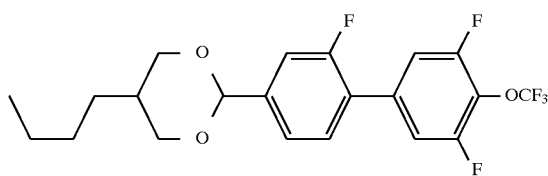  No. 7
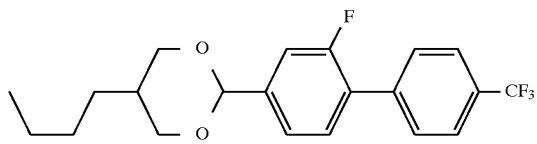  No. 8
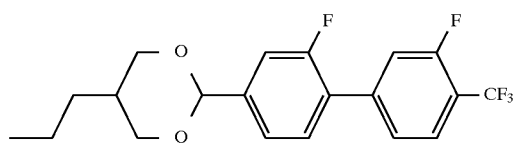  No. 9
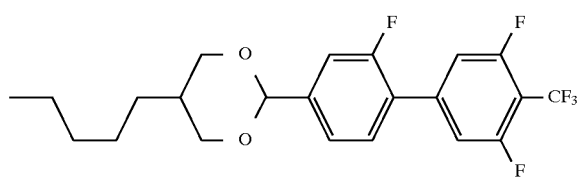  No. 10

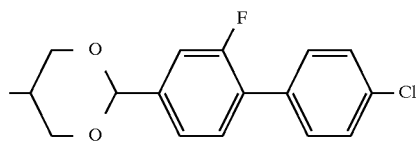 No. 11
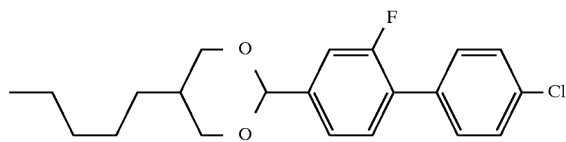 No. 12
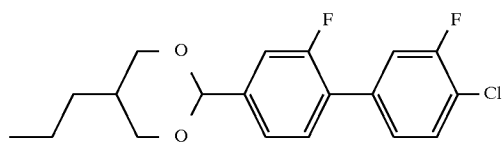 No. 13
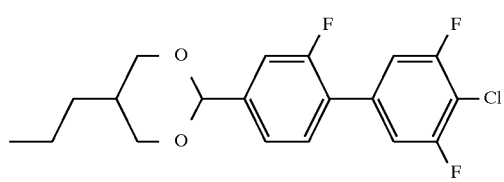 No. 14
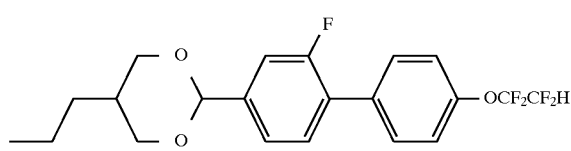 No. 15
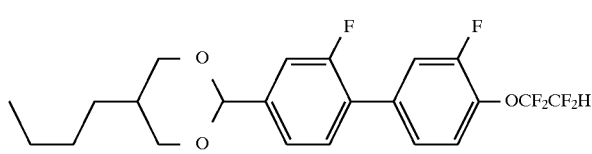 No. 16
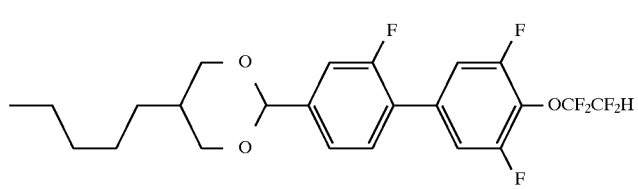 No. 17
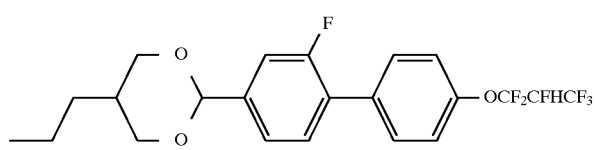 No. 18
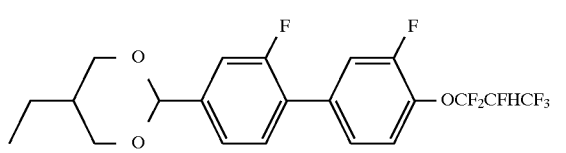 No. 19
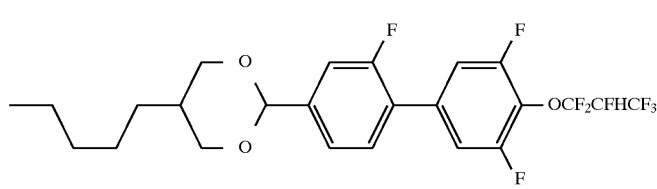 No. 20

-continued
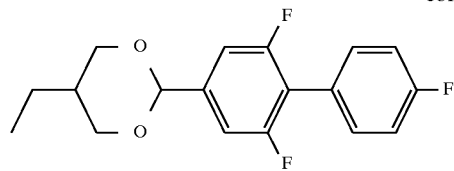 No. 21
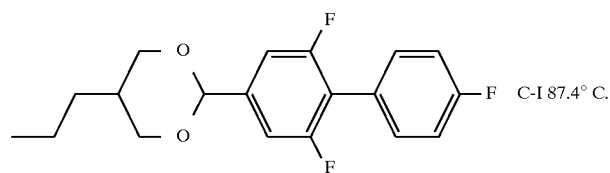 C-I 87.4° C. No. 22
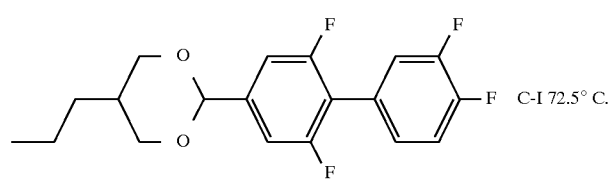 C-I 72.5° C. No. 23
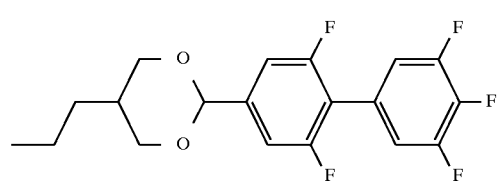 No. 24
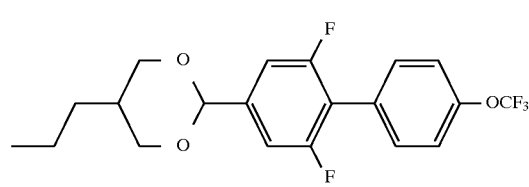 No. 25
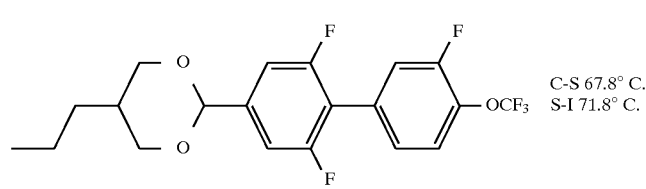 C-S 67.8° C. S-I 71.8° C. No. 26
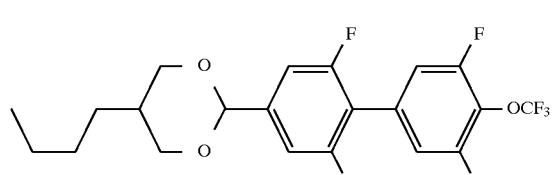 No. 27
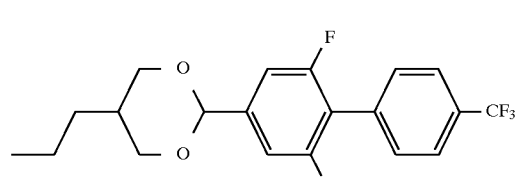 No. 28
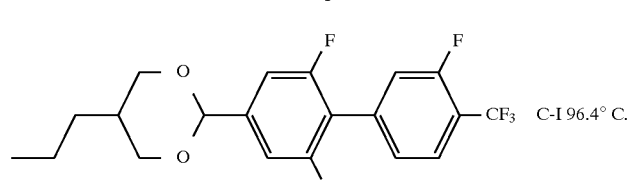 C-I 96.4° C. No. 29

-continued
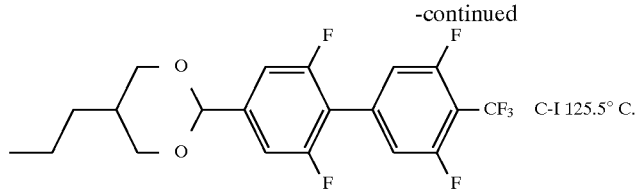 C-I 125.5° C.
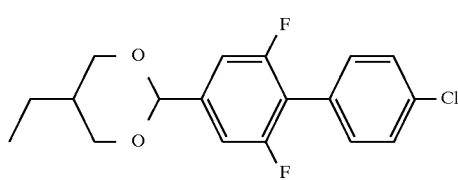
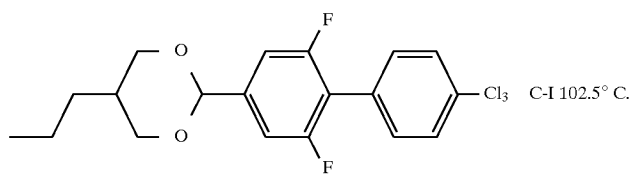 C-I 102.5° C.
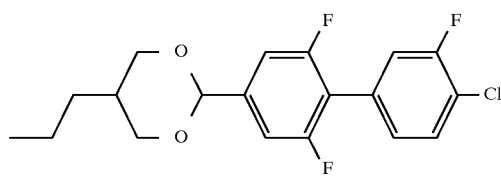
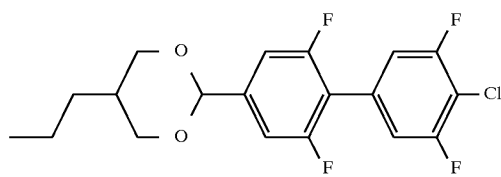
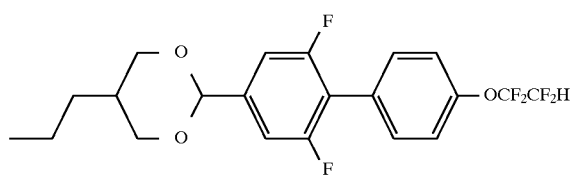
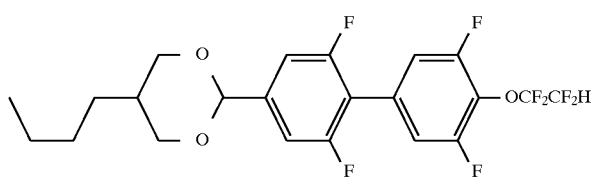
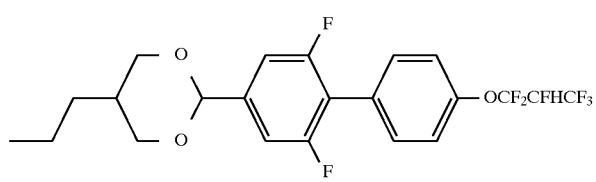
No. 30
No. 31
No. 32
No. 33
No. 34
No. 35
No. 36
No. 37
No. 38

-continued
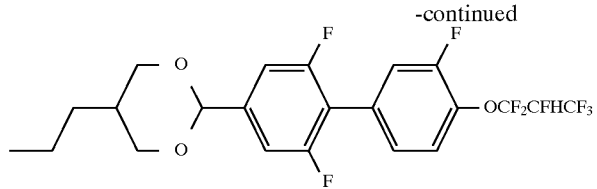
No. 39
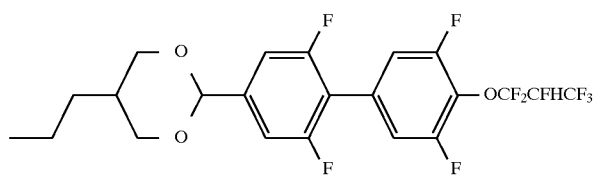
No. 40
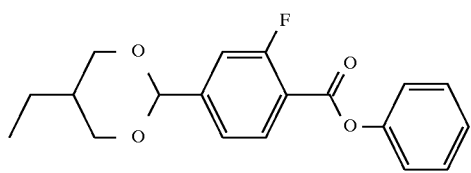
No. 41
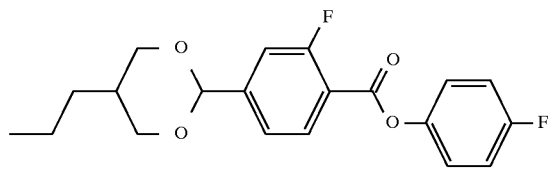
No. 42
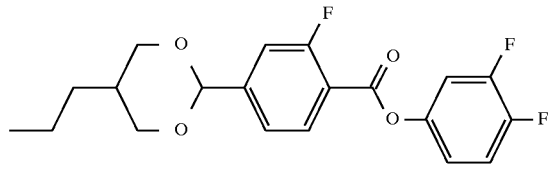
No. 43
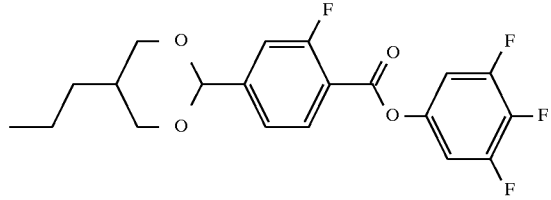
No. 44
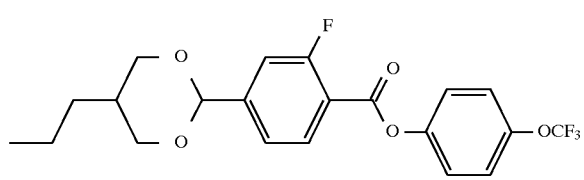
No. 45
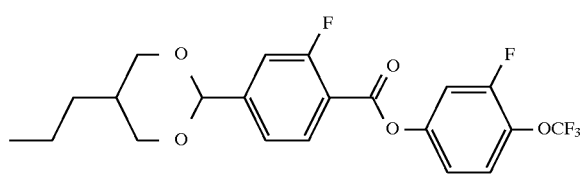
No. 46
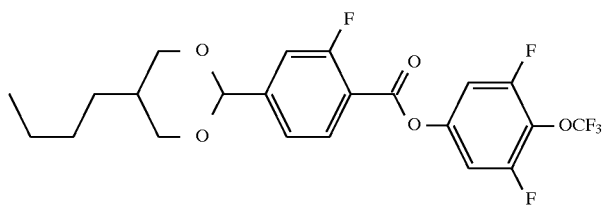
No. 47

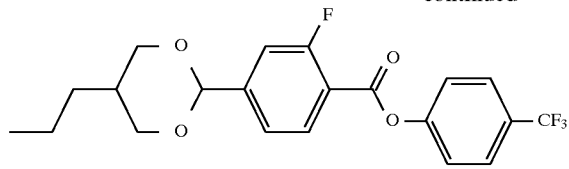
No. 48
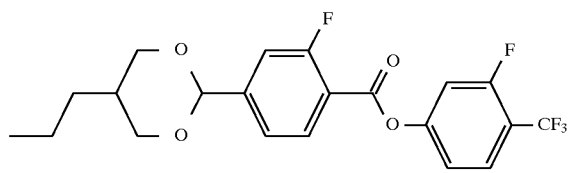
No. 49
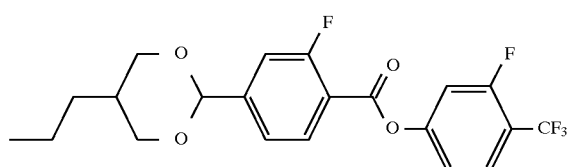
No. 50
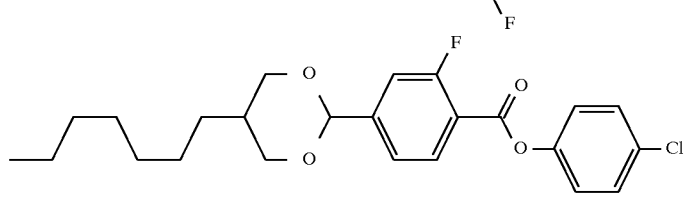
No. 51
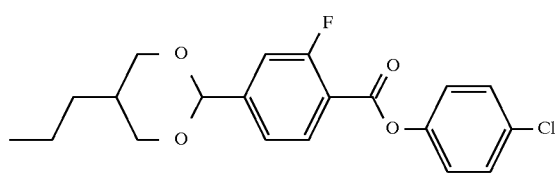
No. 52
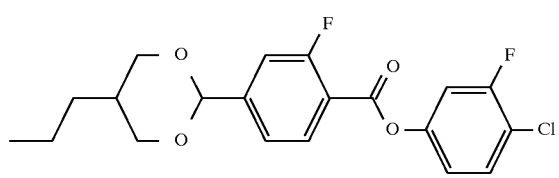
No. 53
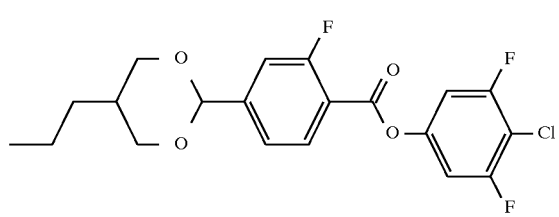
No. 54
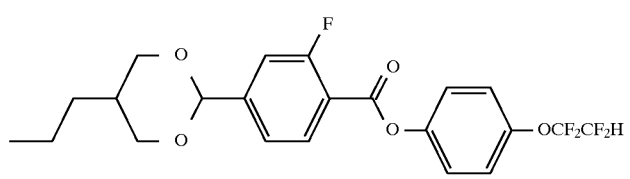
No. 55
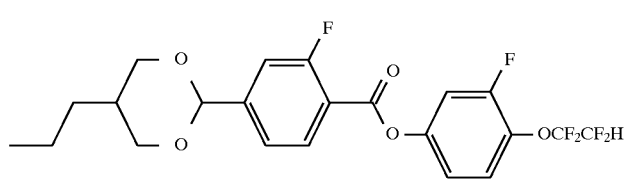
No. 56

-continued
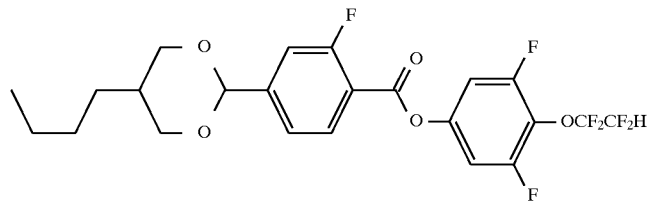
No. 57
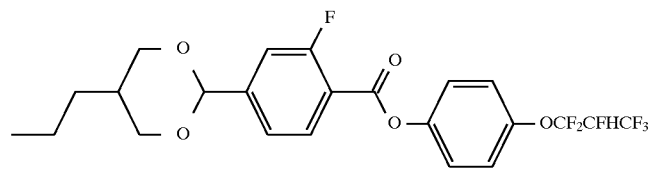
No. 58
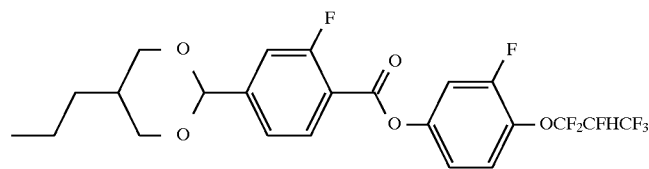
No. 59
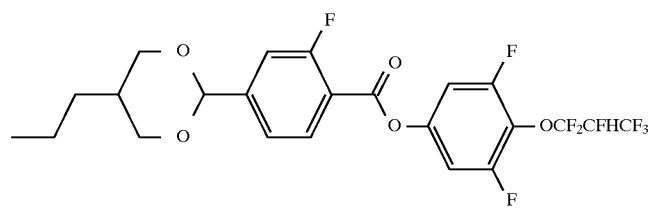
No. 60
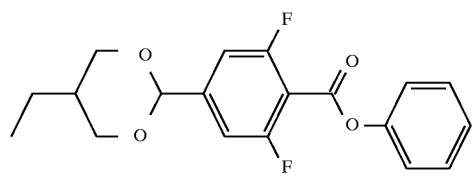
No. 61
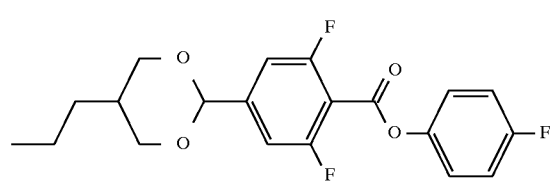
No. 62
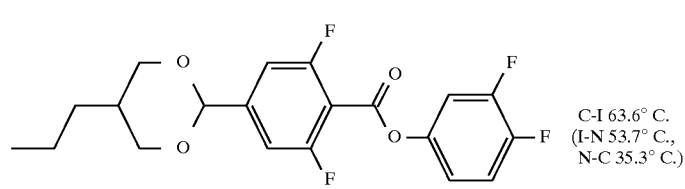
No. 63
C-I 63.6° C.
(I-N 53.7° C.,
N-C 35.3° C.)
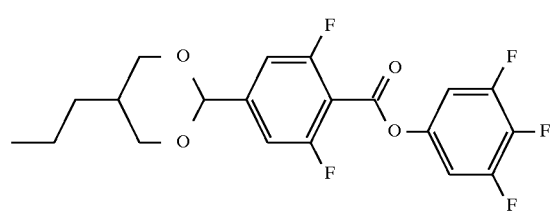
No. 64

-continued
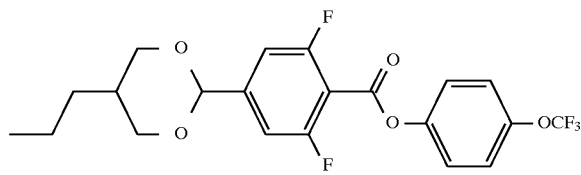 No. 65
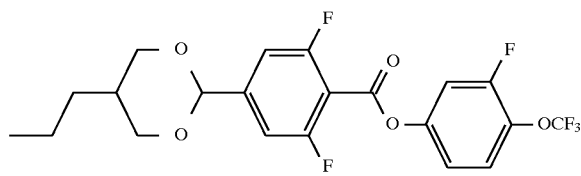 No. 66
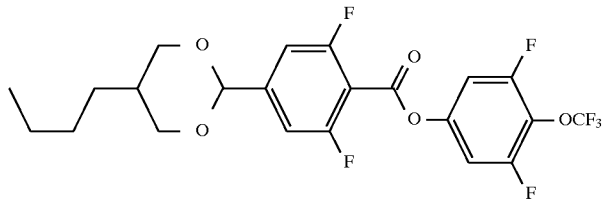 No. 67
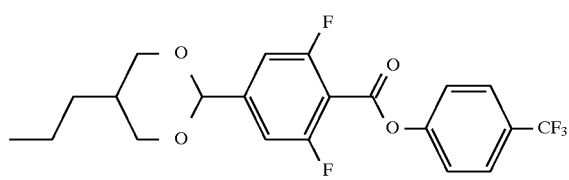 No. 68
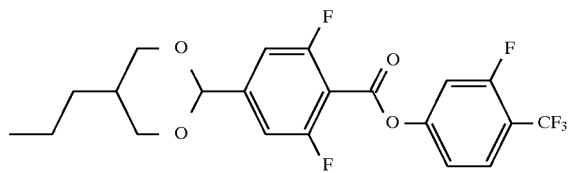 No. 69
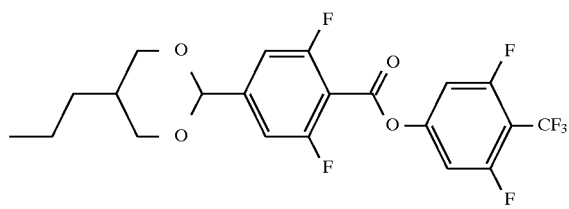 No. 70
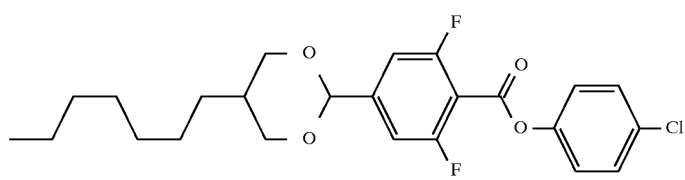 No. 71
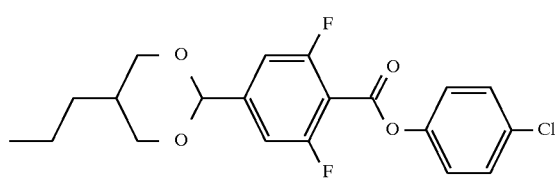 No. 72

-continued
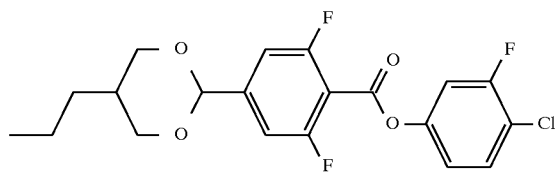
No. 73
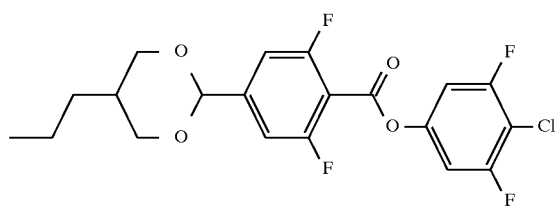
No. 74
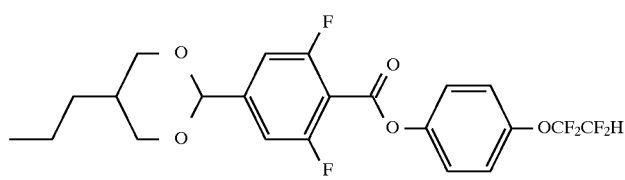
No. 75
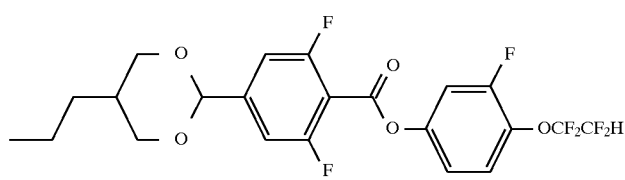
No. 76
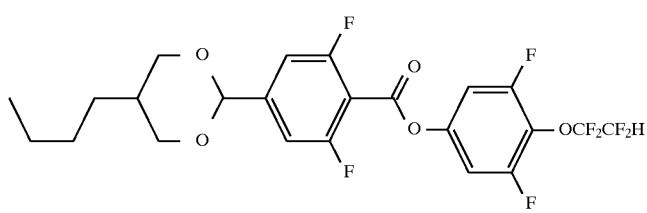
No. 77
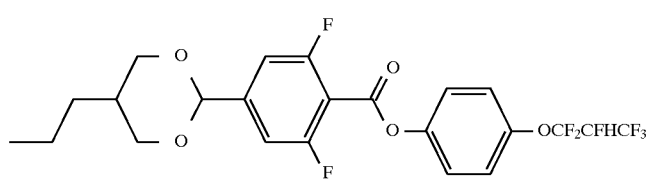
No. 78
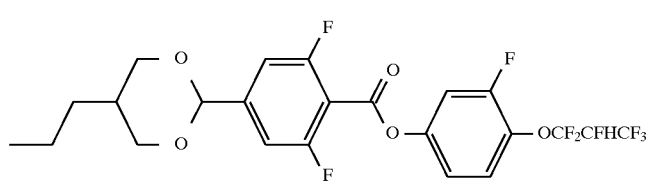
No. 79
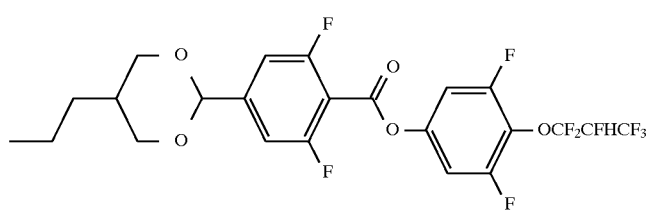
No. 80

-continued
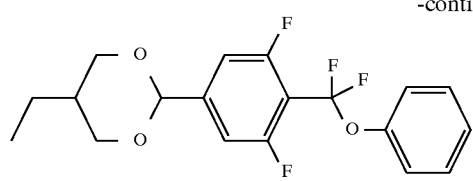
No. 81
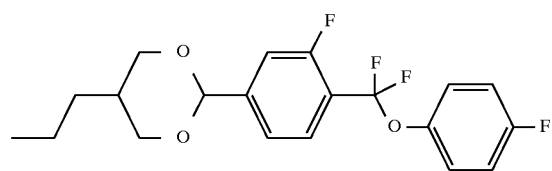
No. 82
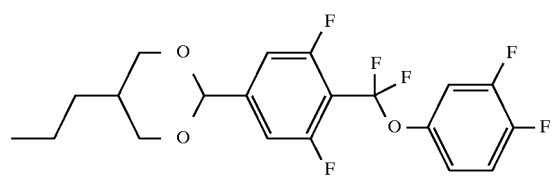
No. 83
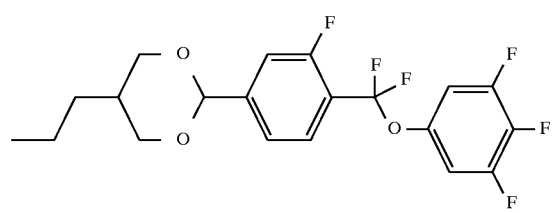
No. 84
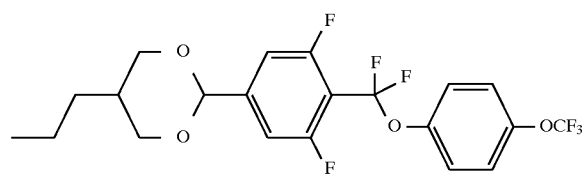
No. 85
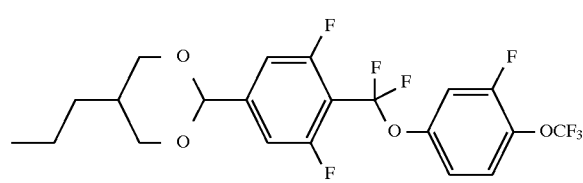
No. 86
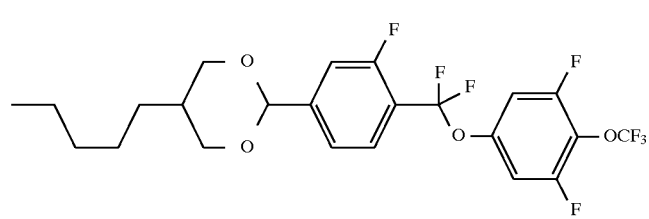
No. 87
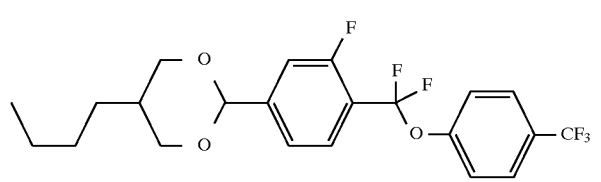
No. 88
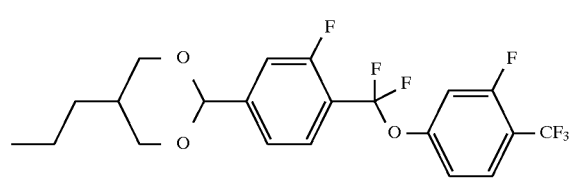
No. 89

-continued
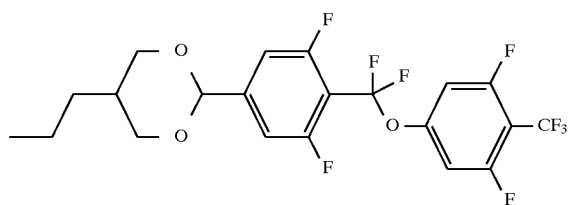
No. 90
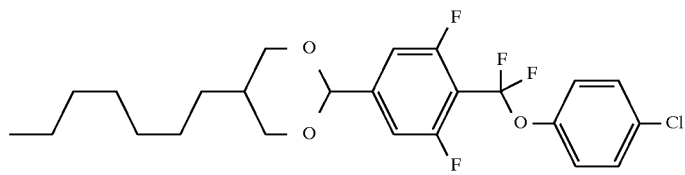
No. 91
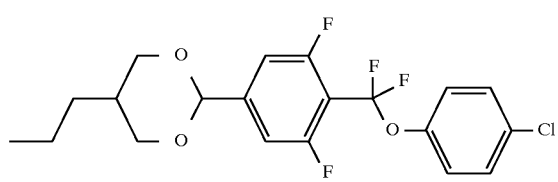
No. 92
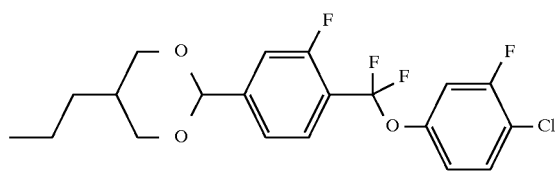
No. 93
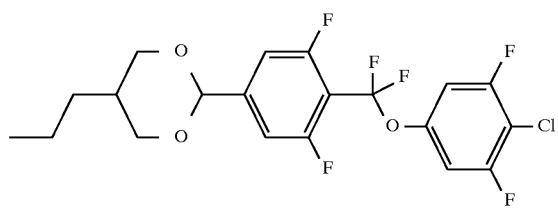
No. 94
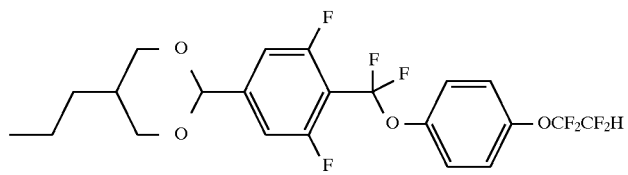
No. 95
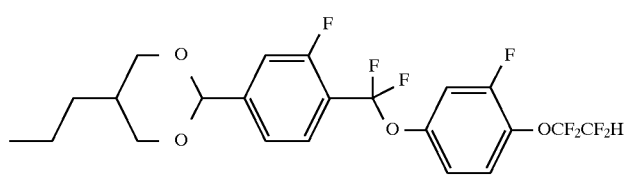
No. 96
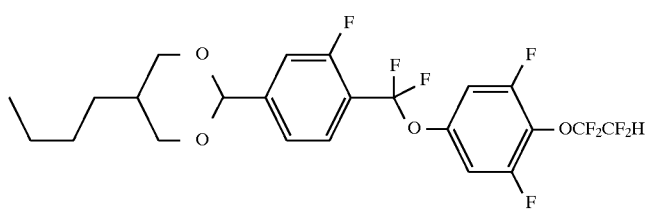
No. 97

-continued
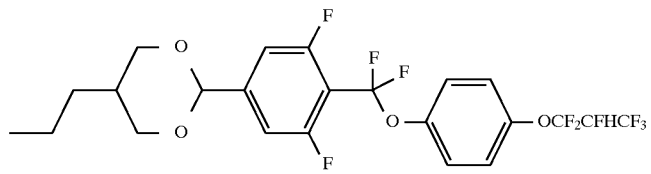
No. 98
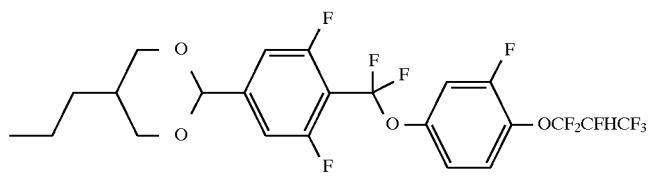
No. 99
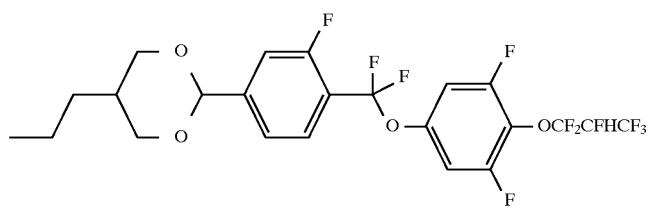
No. 100
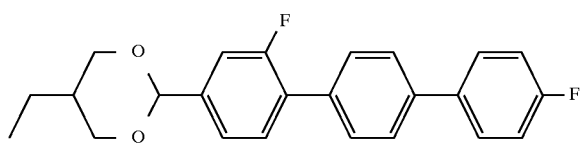
No. 101
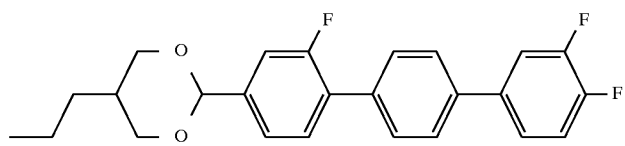
No. 102
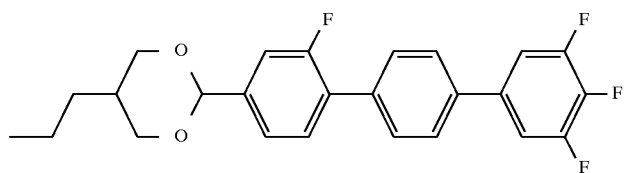
No. 103
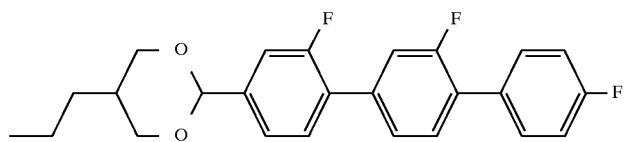
No. 104
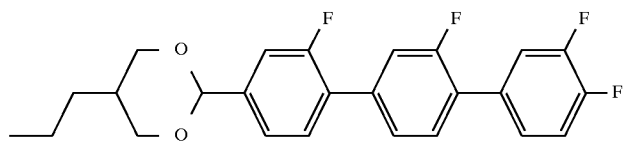
No. 105
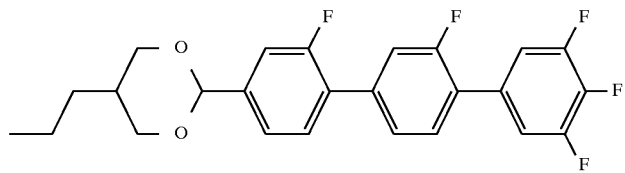
No. 106

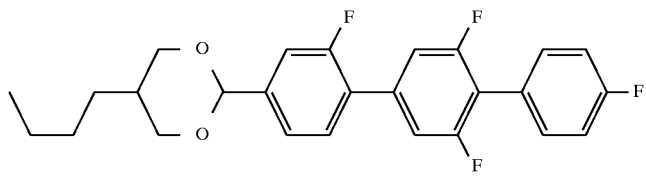
No. 107
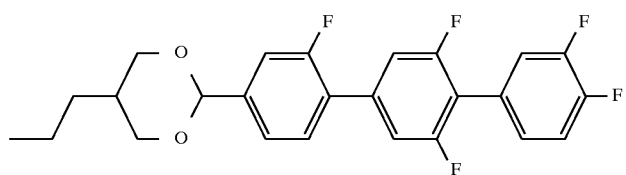
No. 108
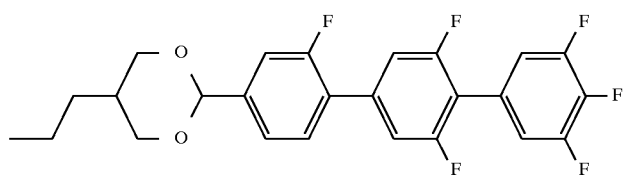
No. 109
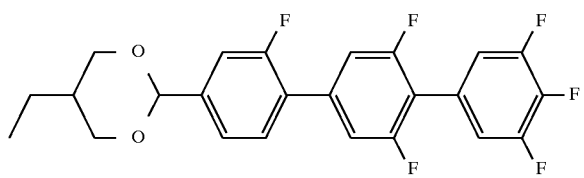
No. 110
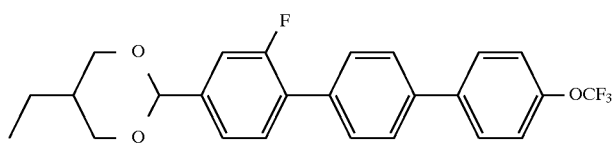
No. 111
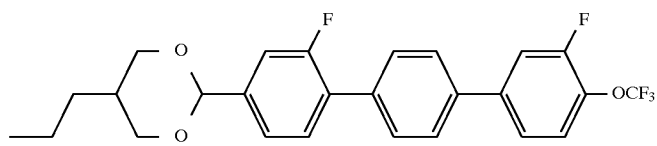
No. 112
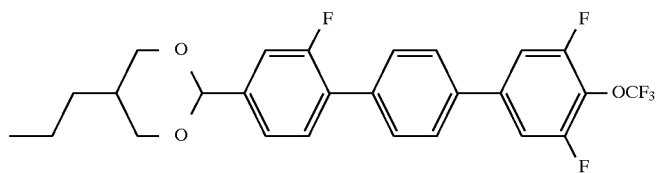
No. 113
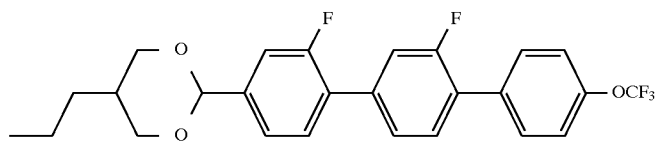
No. 114
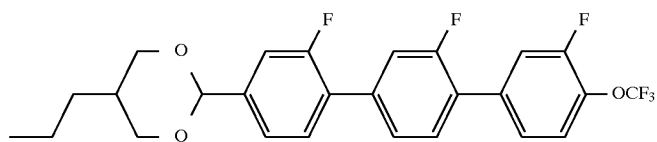
No. 115

-continued
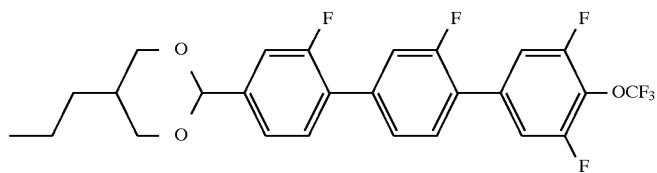
No. 116
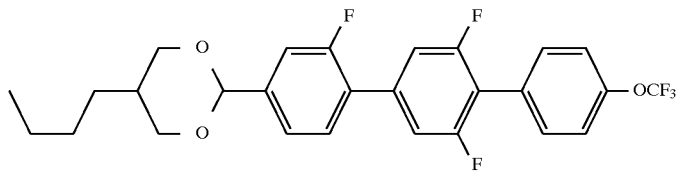
No. 117
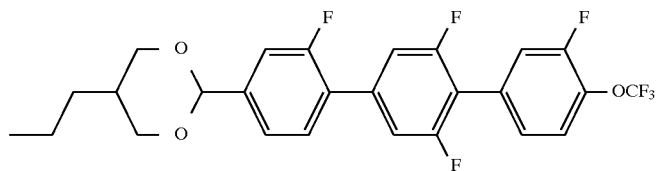
No. 118
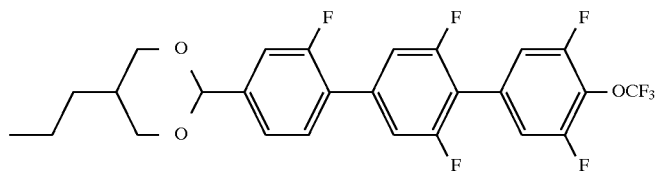
No. 119
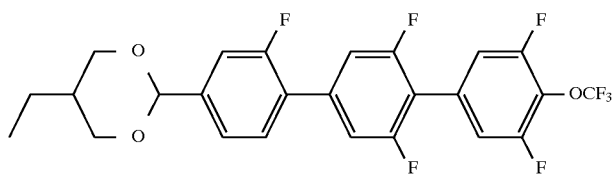
No. 120
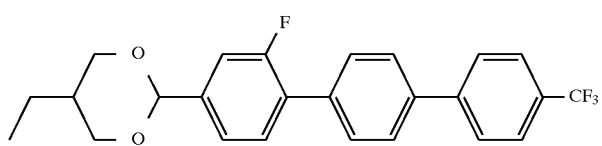
No. 121
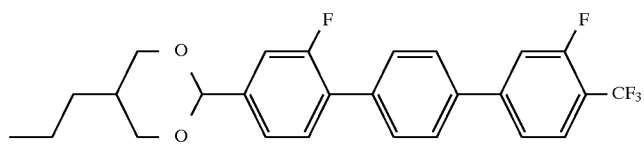
No. 122
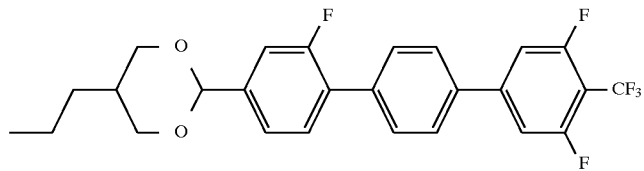
No. 123
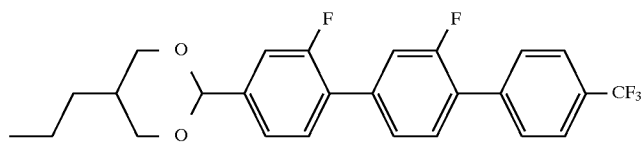
No. 124

-continued
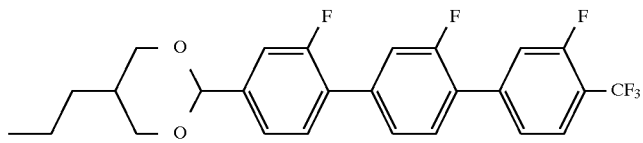 No. 125
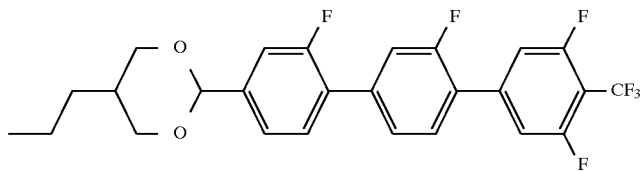 No. 126
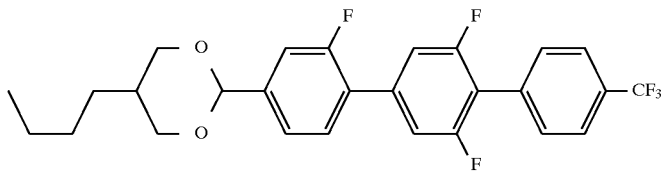 No. 127
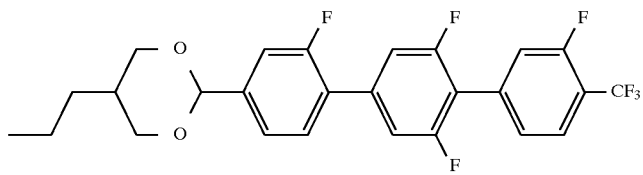 No. 128
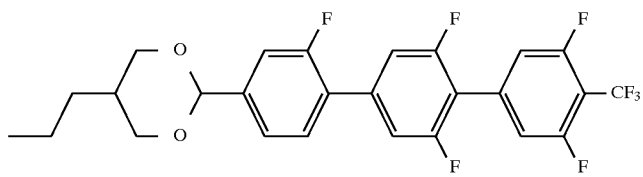 No. 129
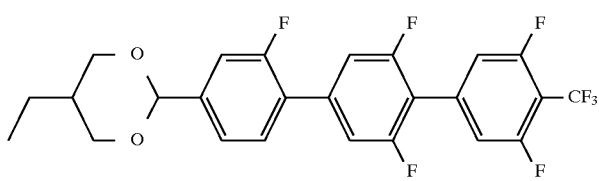 No. 130
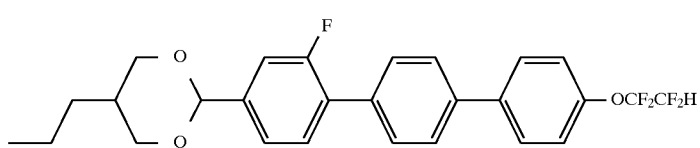 No. 131
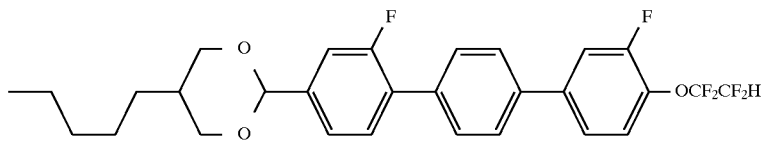 No. 132
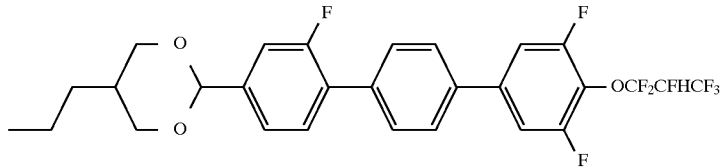 No. 133

-continued
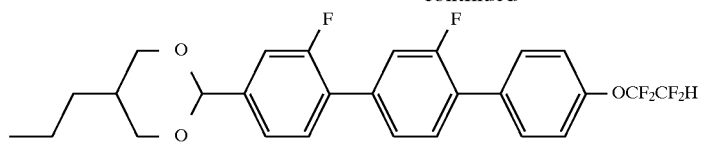 No. 134
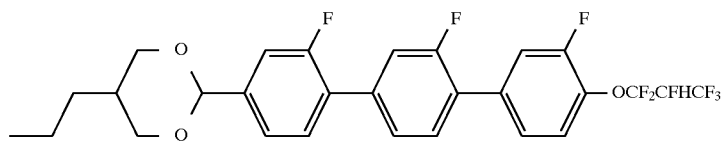 No. 135
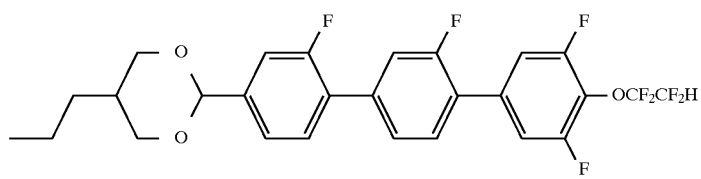 No. 136
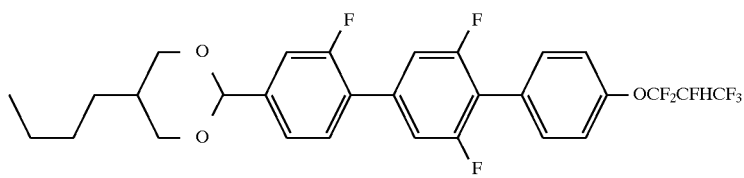 No. 137
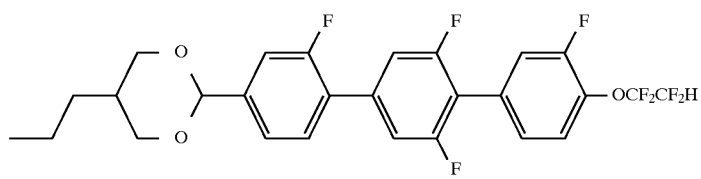 No. 138
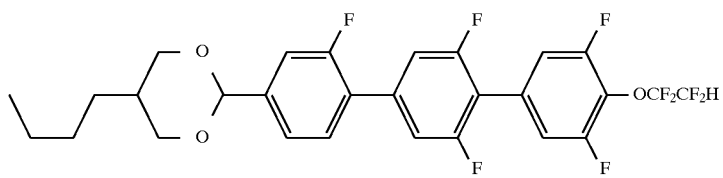 No. 139
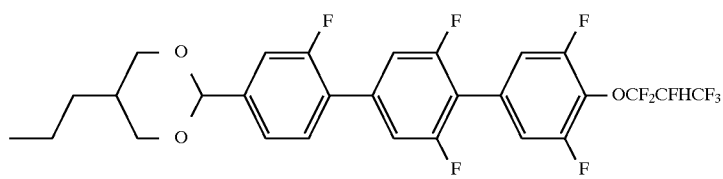 No. 140
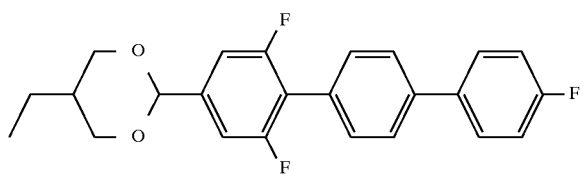 No. 141
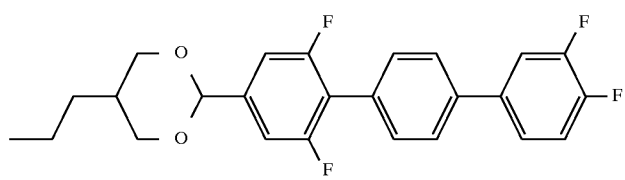 No. 142

-continued
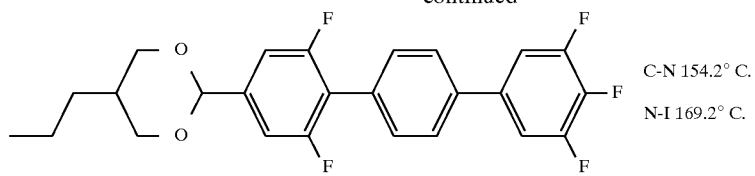
C-N 154.2° C.
N-I 169.2° C.
No. 143
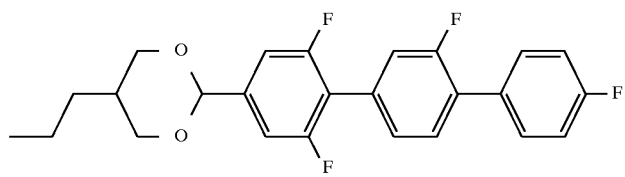
No. 144
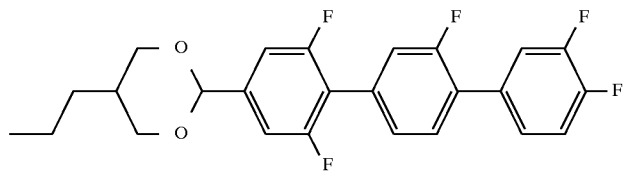
No. 145
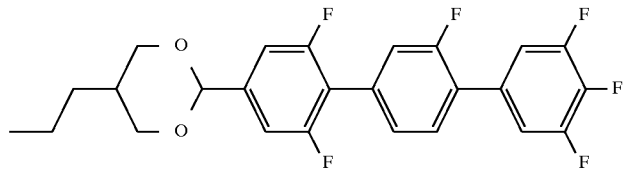
No. 146
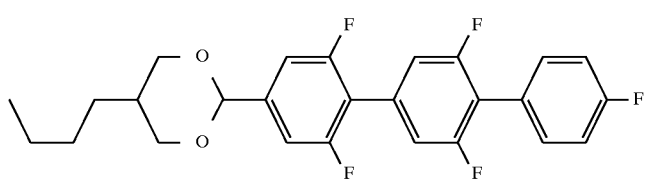
No. 147
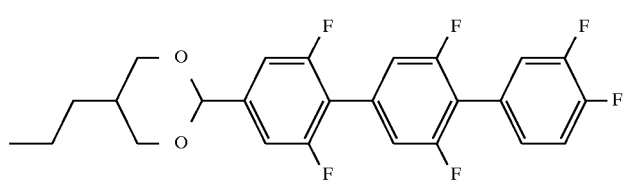
No. 148
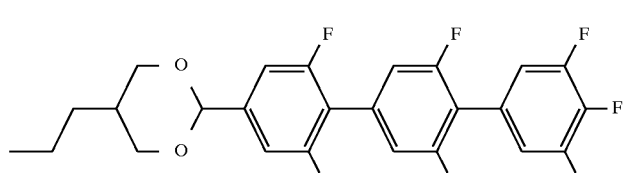
No. 149
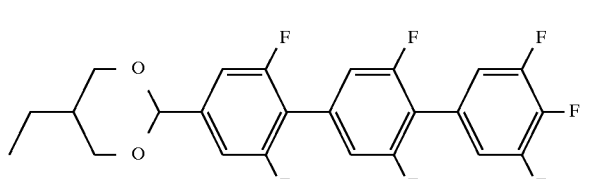
No. 150
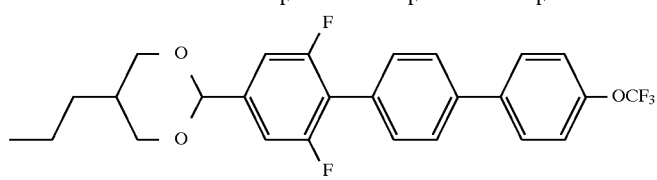
No. 151

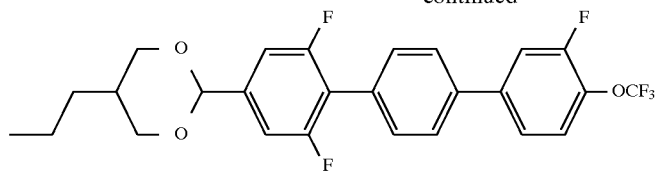
No. 152
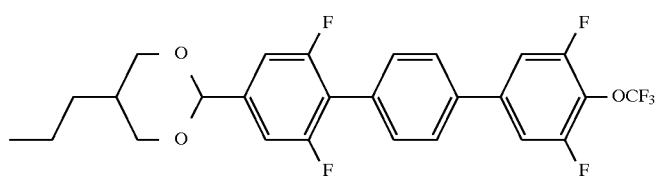
No. 153
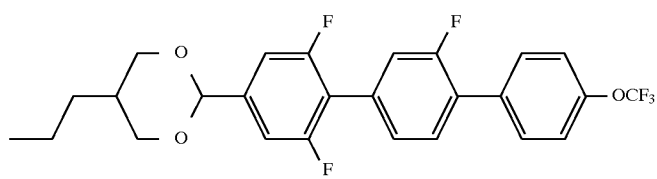
No. 154
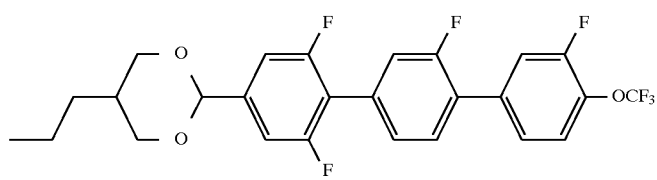
No. 155
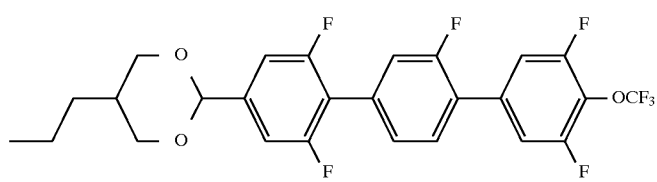
No. 156
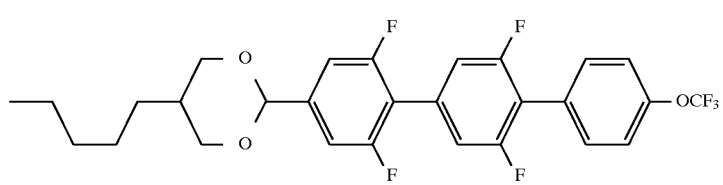
No. 157
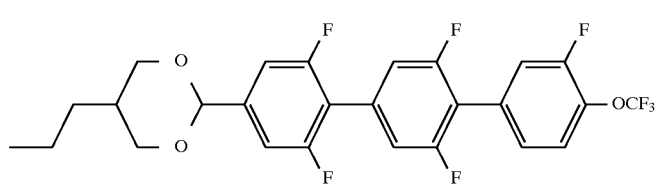
No. 158
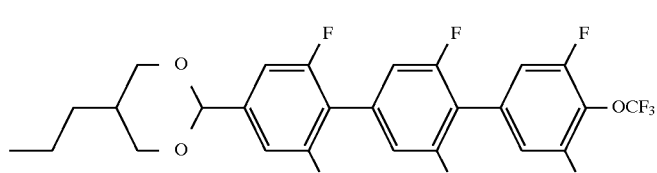
No. 159
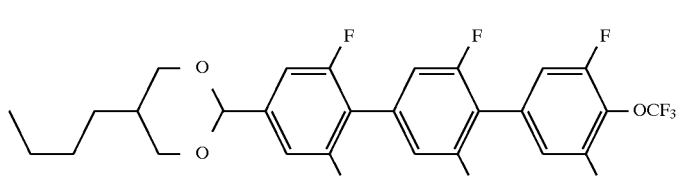
No. 160

-continued
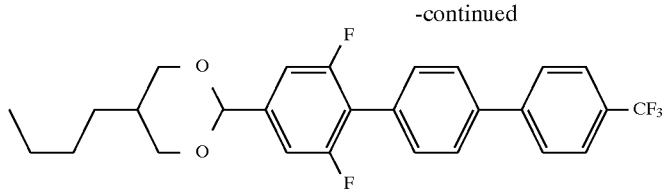 No. 161
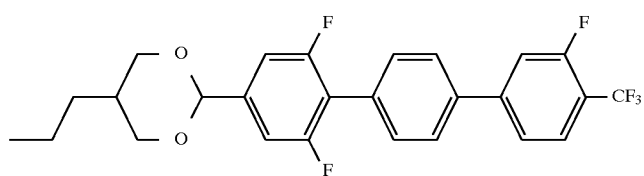 No. 162
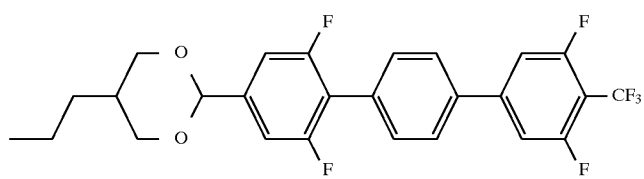 No. 163
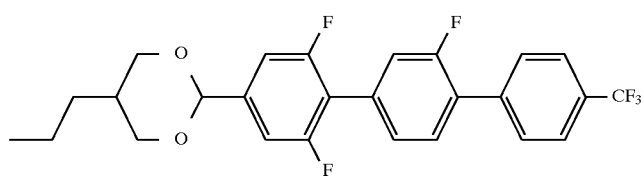 No. 164
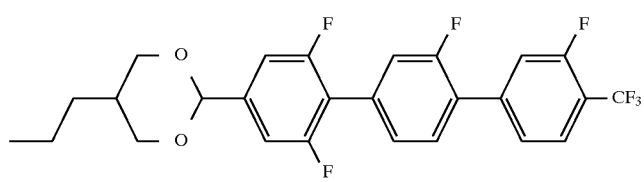 No. 165
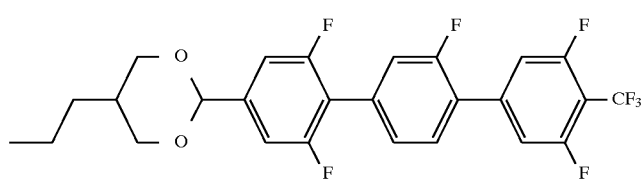 No. 166
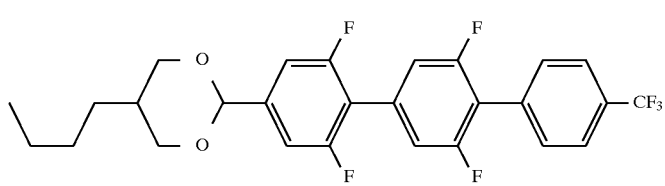 No. 167
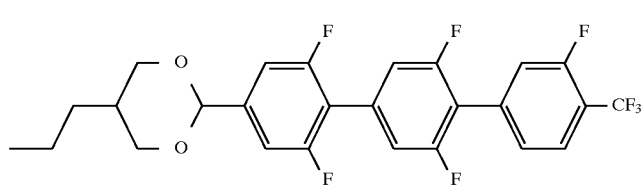 No. 168
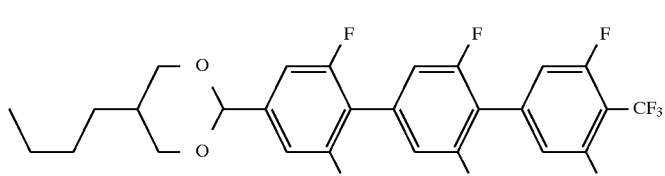 No. 169

-continued
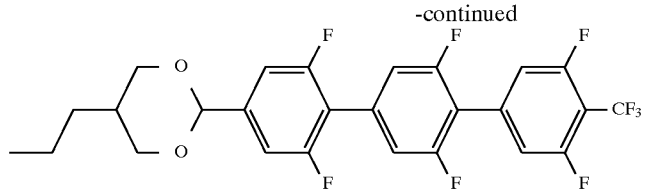 No. 170
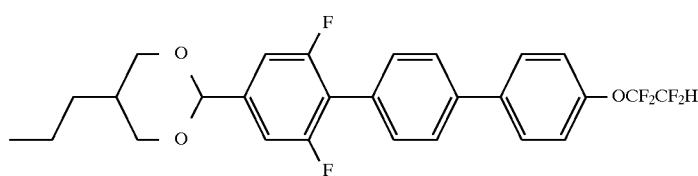 No. 171
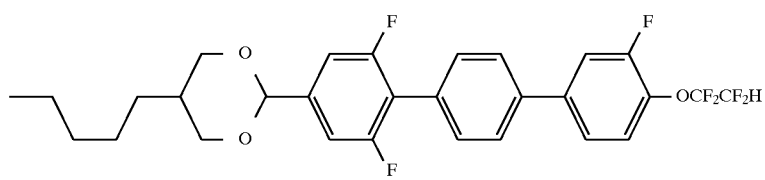 No. 172
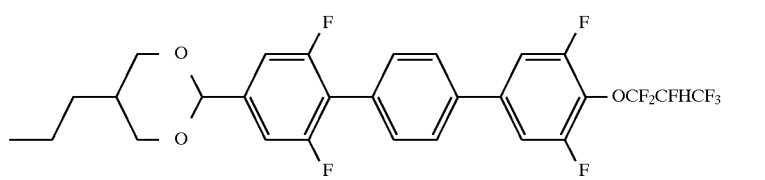 No. 173
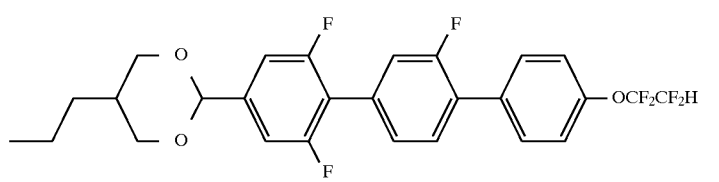 No. 174
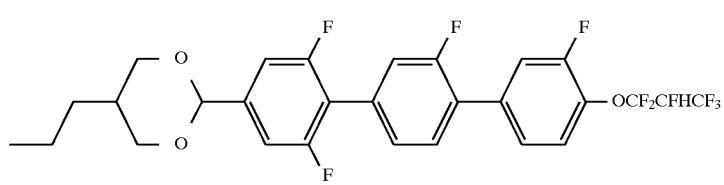 No. 175
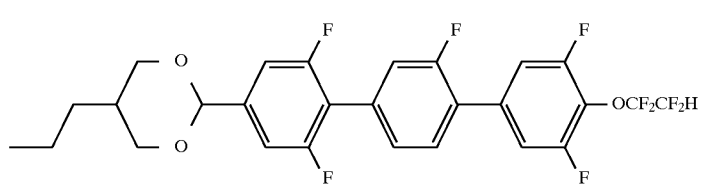 No. 176
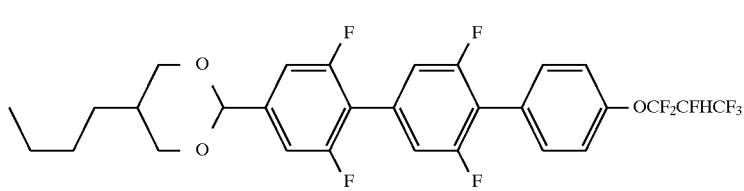 No. 177
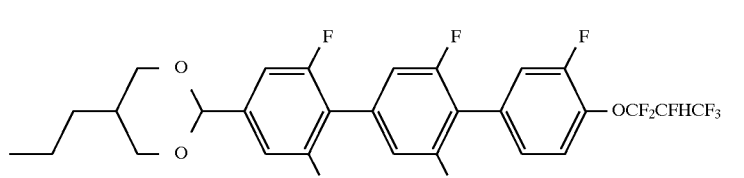 No. 178

-continued
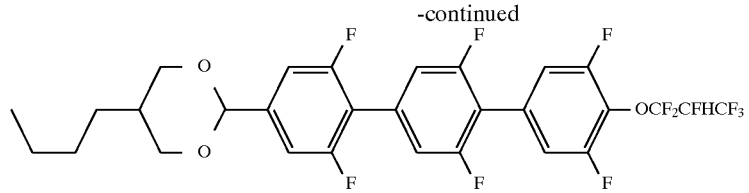
No. 179
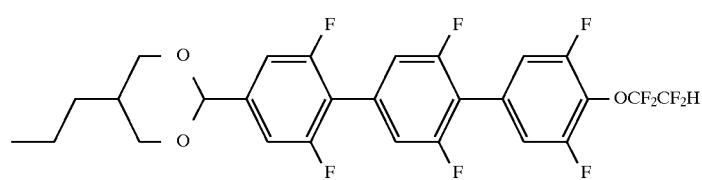
No. 180
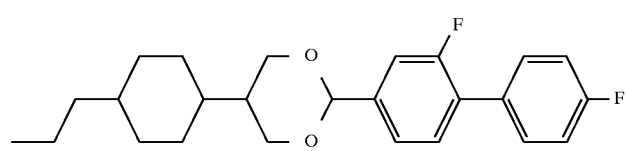
No. 181
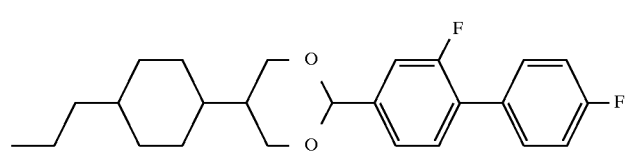
No. 182
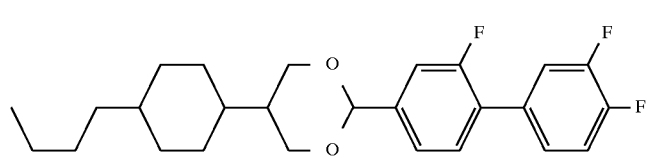
No. 183
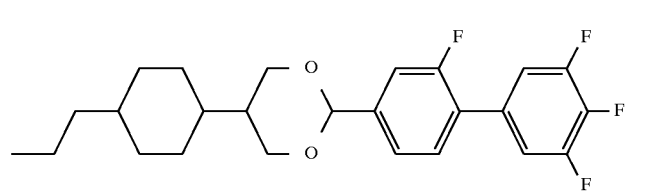
No. 184
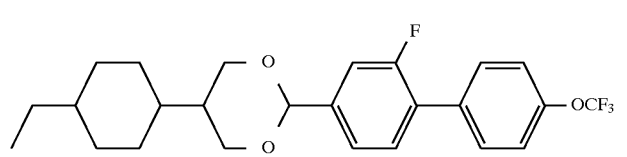
No. 185
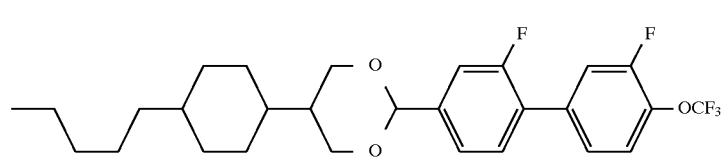
No. 186
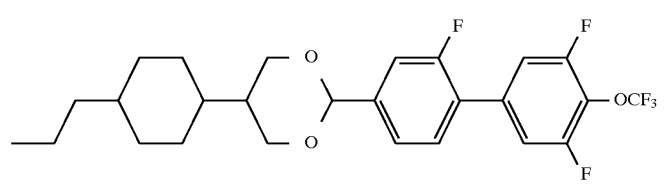
No. 187
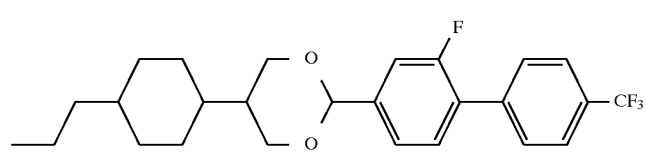
No. 188

-continued
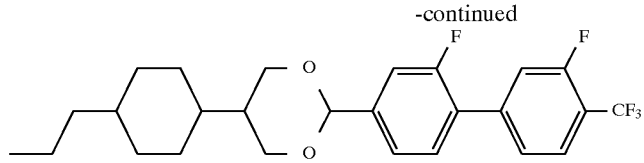 No. 189
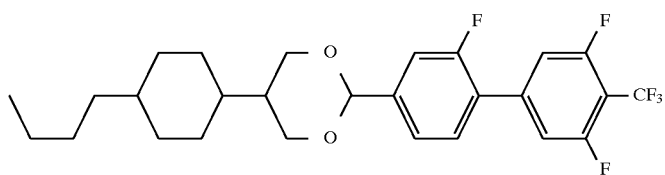 No. 190
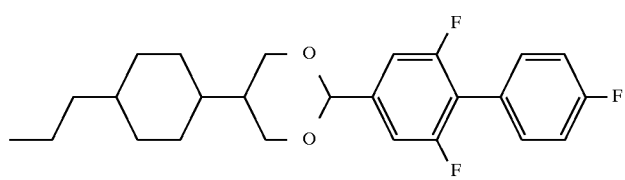 No. 191
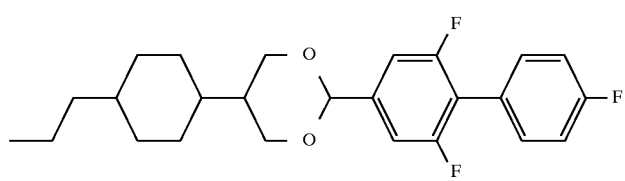 No. 192
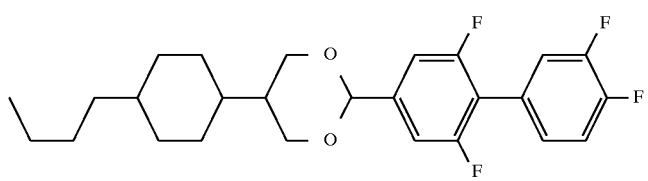 No. 193
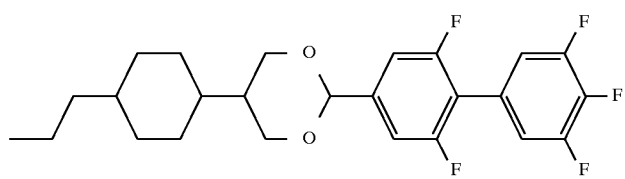 No. 194
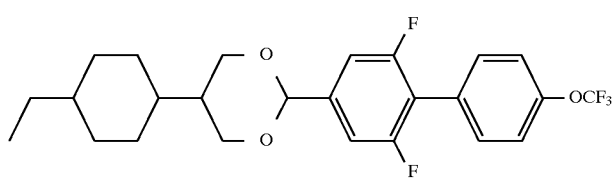 No. 195
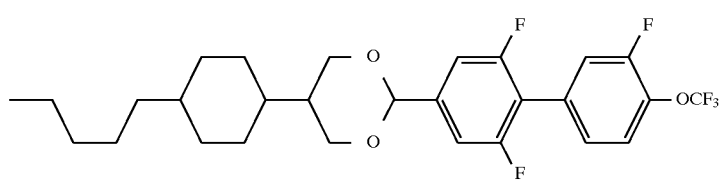 No. 196
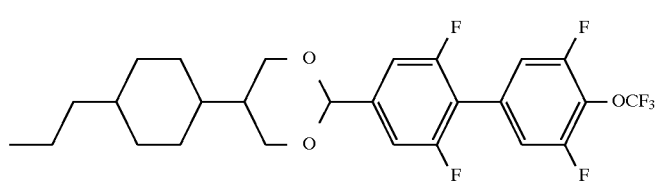 No. 197

-continued
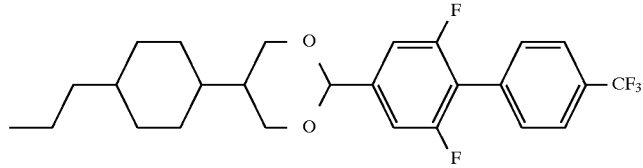
No. 198
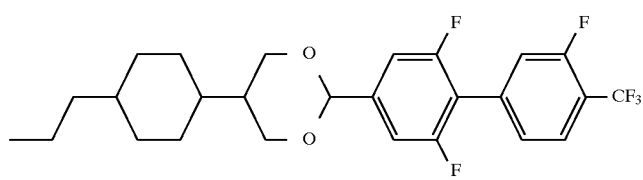
No. 199
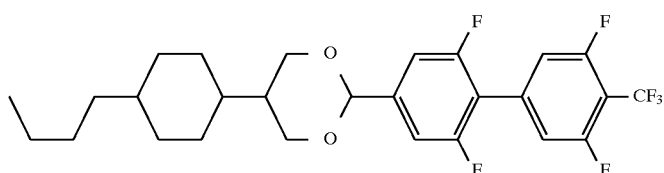
No. 200
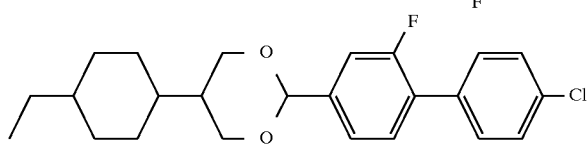
No. 201
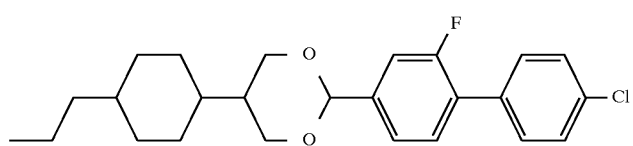
No. 202
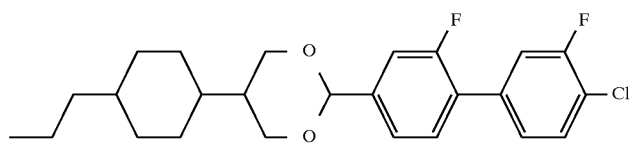
No. 203
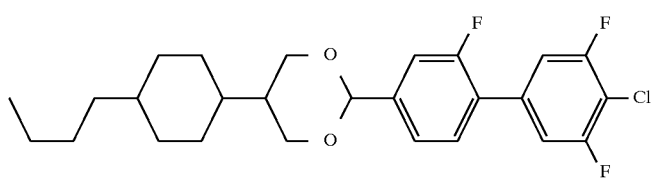
No. 204
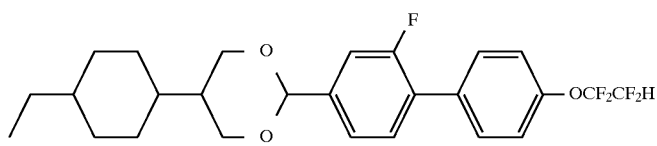
No. 205
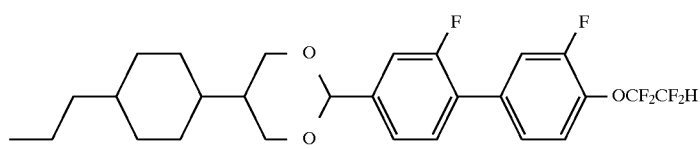
No. 206
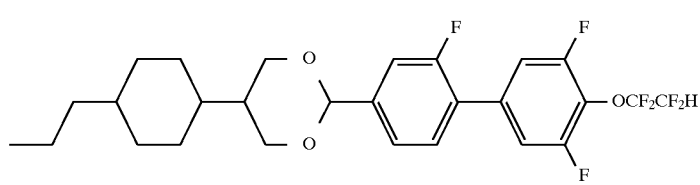
No. 207

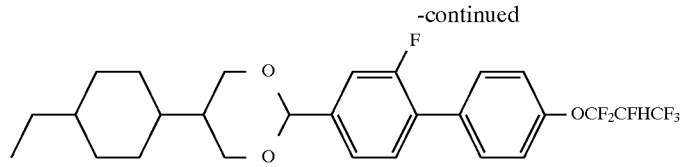
No. 208
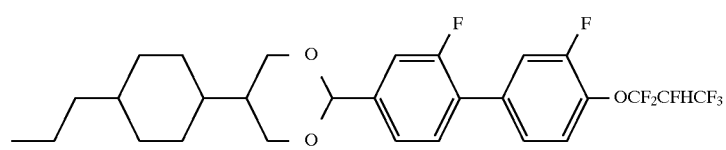
No. 209
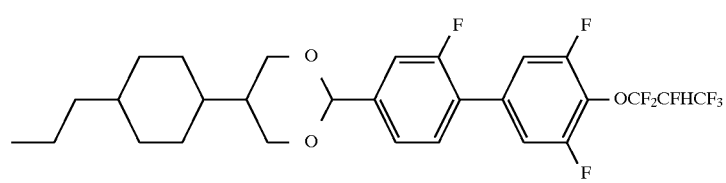
No. 210
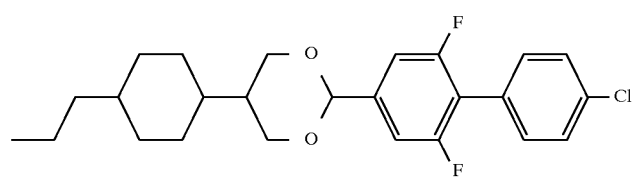
No. 211
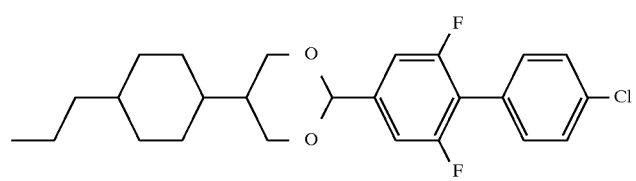
No. 212
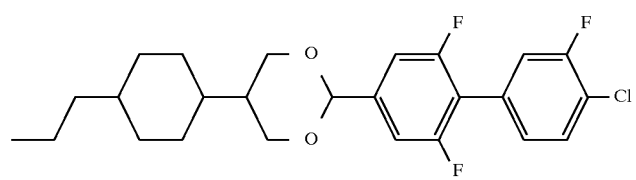
No. 213
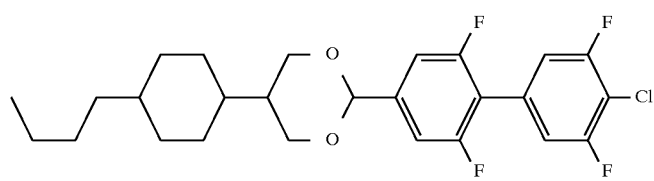
No. 214
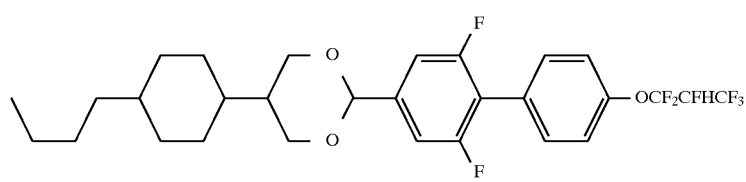
No. 215
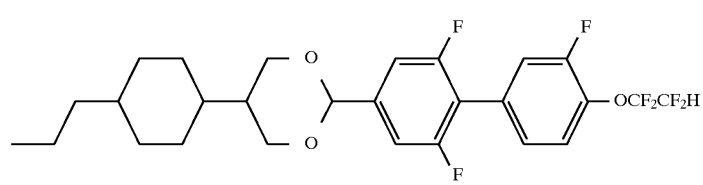
No. 216

-continued
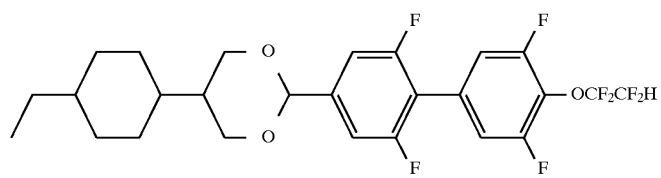 No. 217
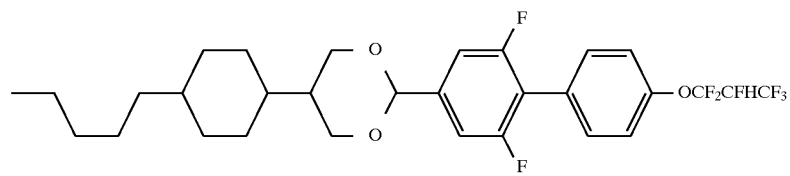 No. 218
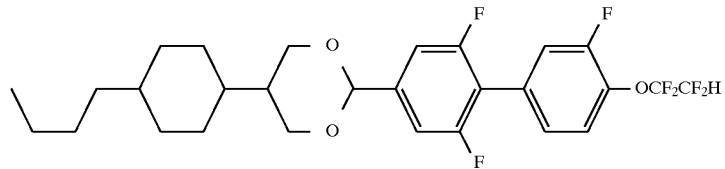 No. 219
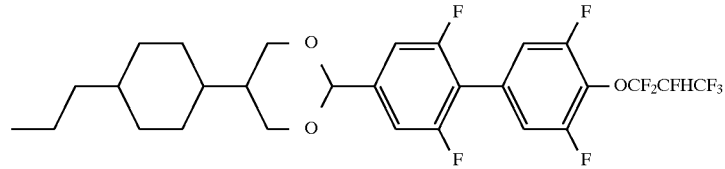 No. 220
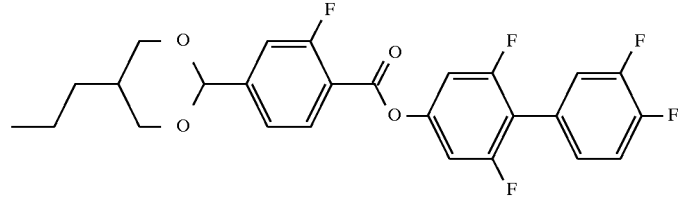 No. 221
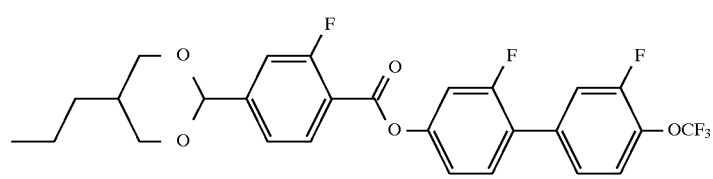 No. 222
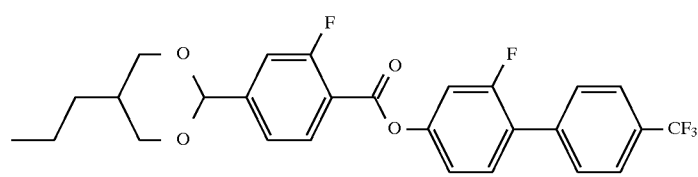 No. 223
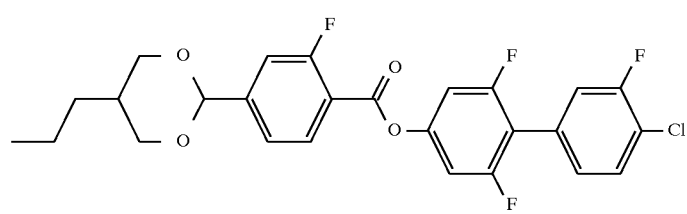 No. 224

-continued
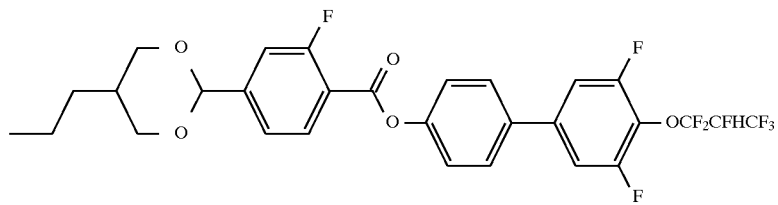
No. 225
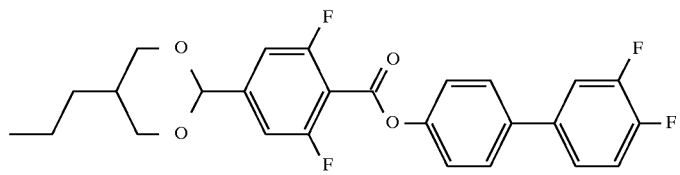
No. 226
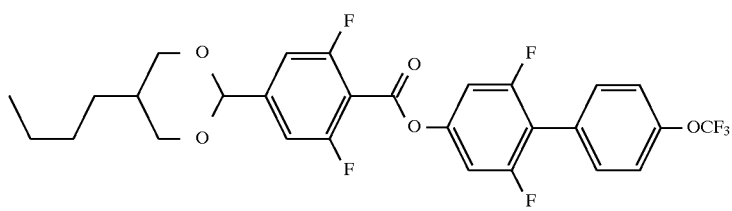
No. 227
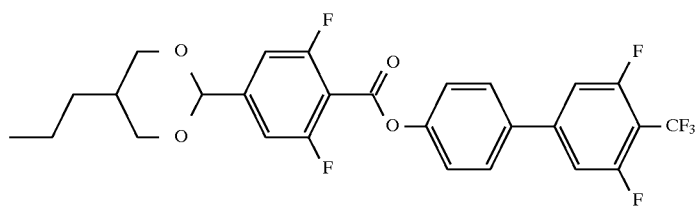
No. 228
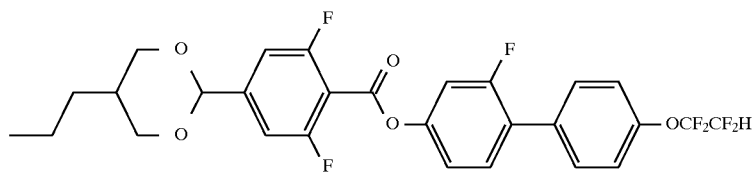
No. 229
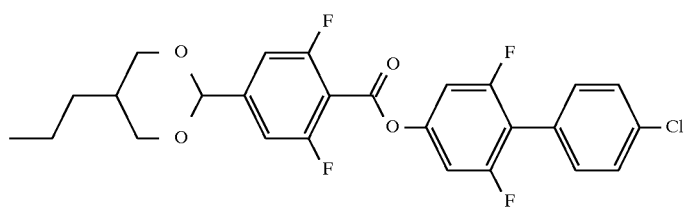
No. 230
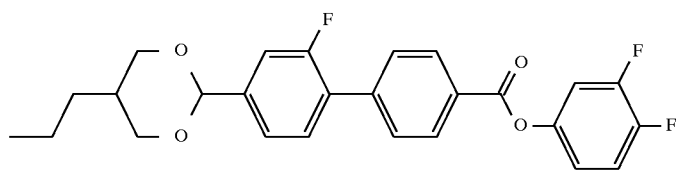
No. 231
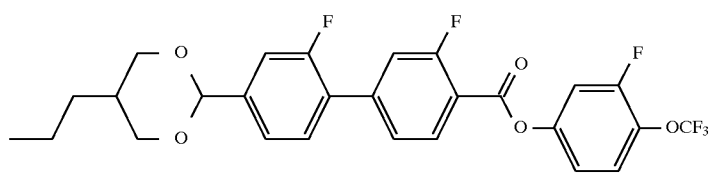
No. 232

-continued
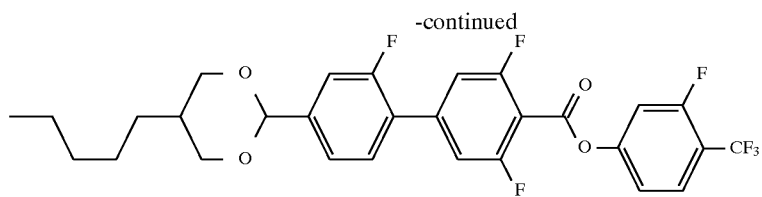
No. 233
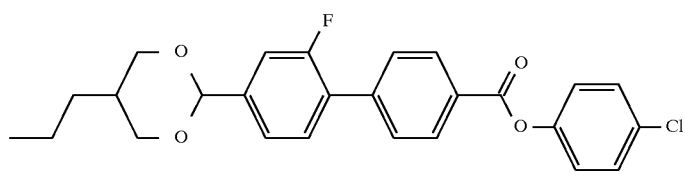
No. 234
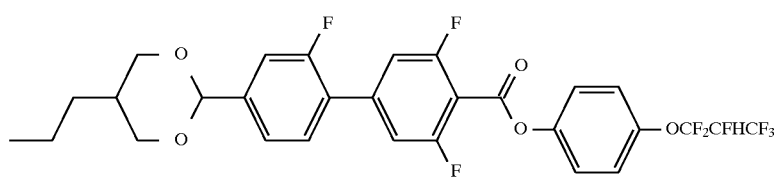
No. 235
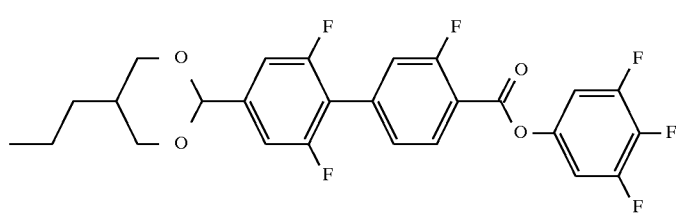
No. 236
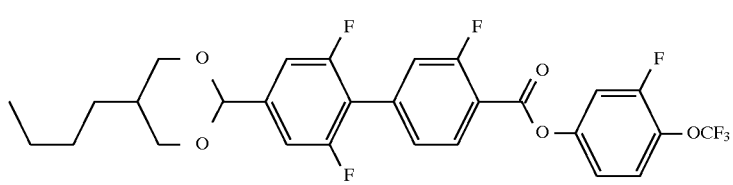
No. 237
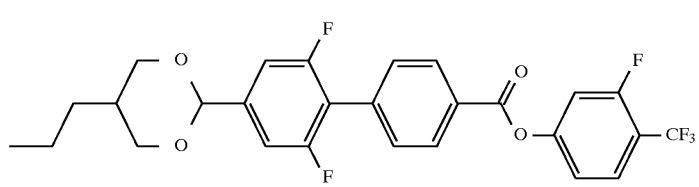
No. 238
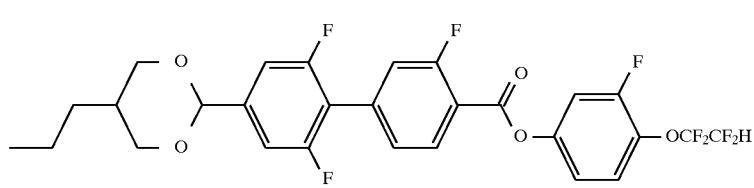
No. 239
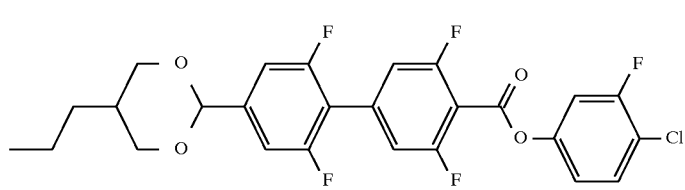
No. 240
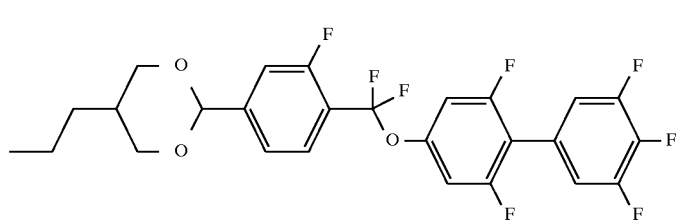
No. 241

-continued
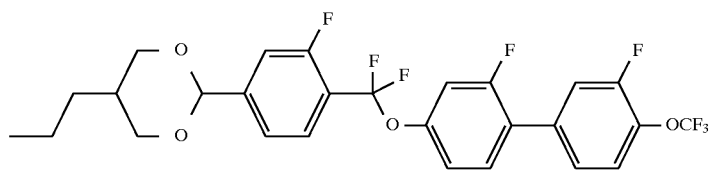
No. 242
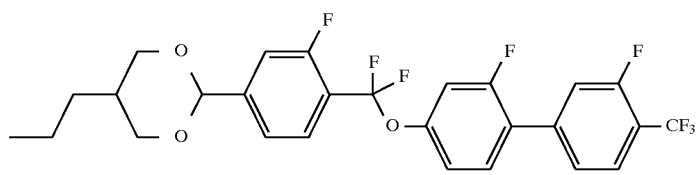
No. 243
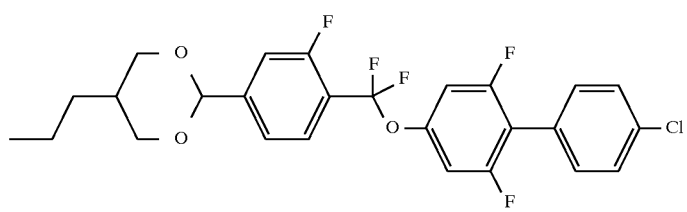
No. 244
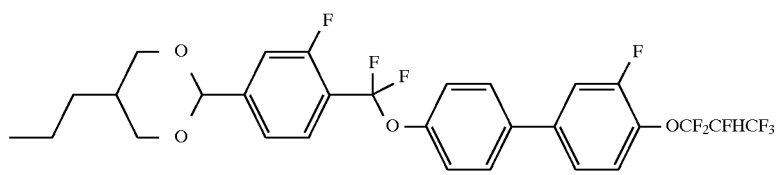
No. 245
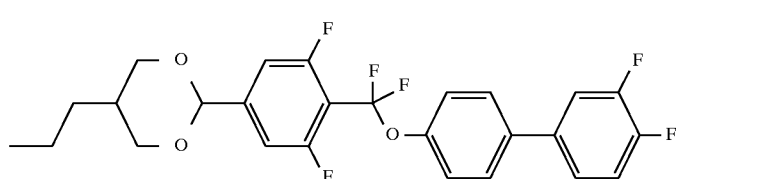
No. 246
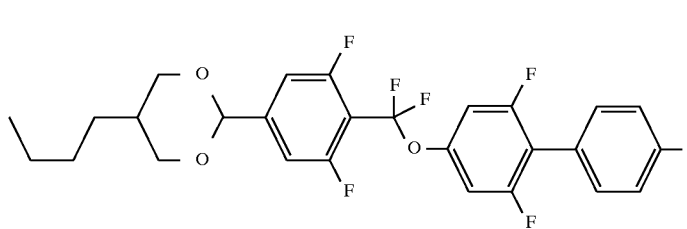
No. 247
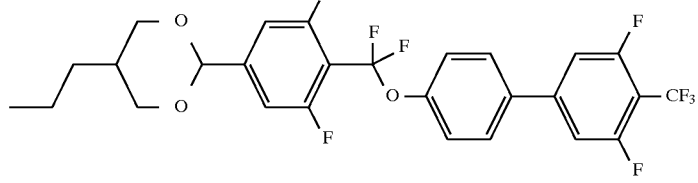
No. 248
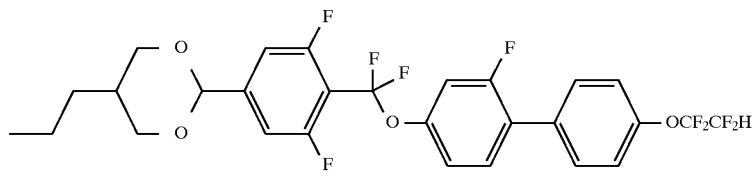
No. 249

-continued
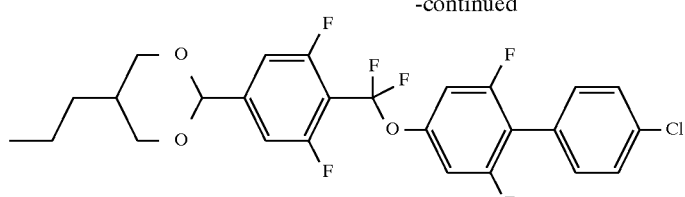 No. 250
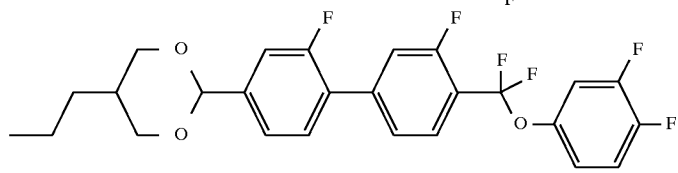 No. 251
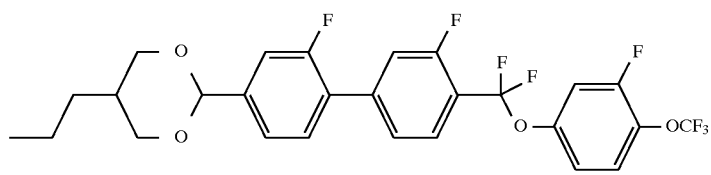 No. 252
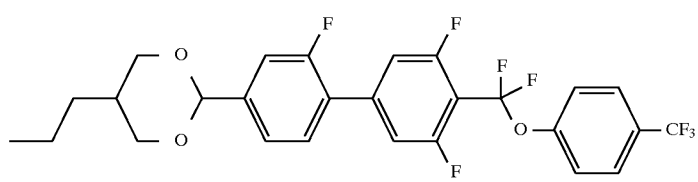 No. 253
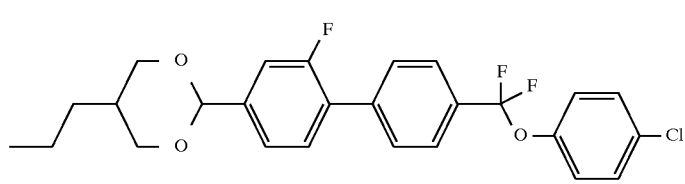 No. 254
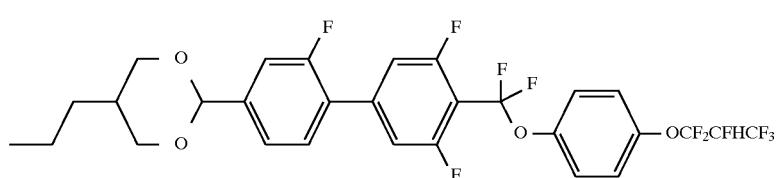 No. 255
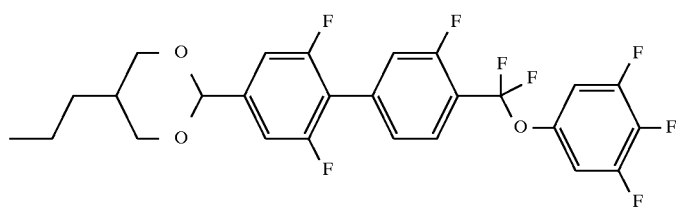 No. 256
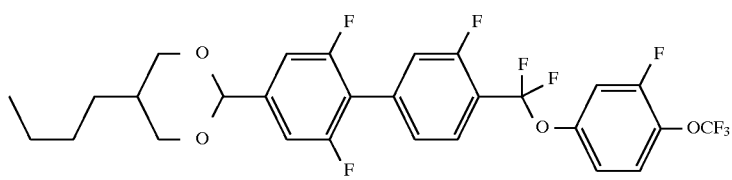 No. 257
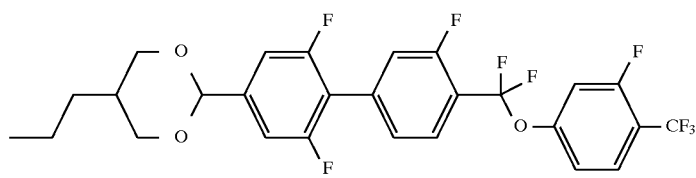 No. 258

-continued
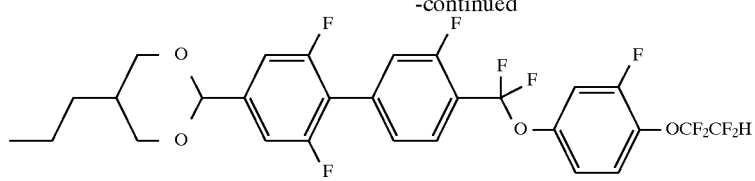 No. 259
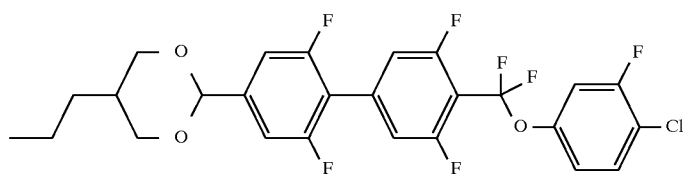 No. 260
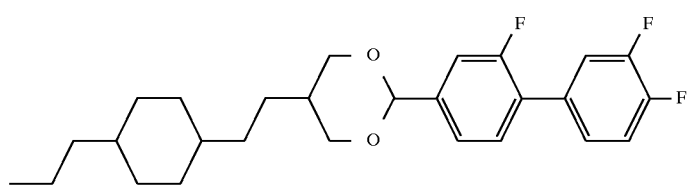 No. 261
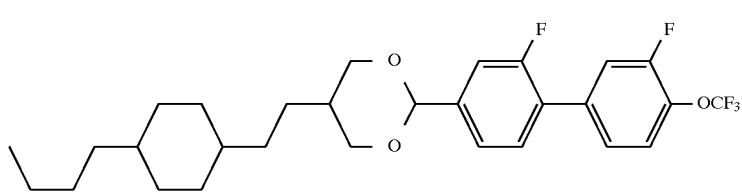 No. 262
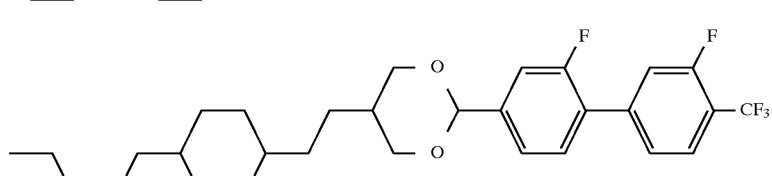 No. 263
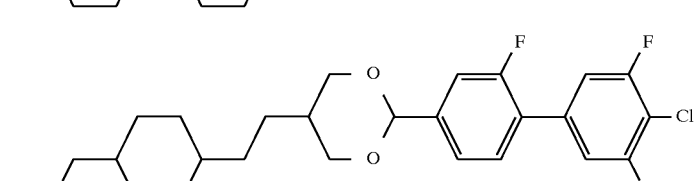 No. 264
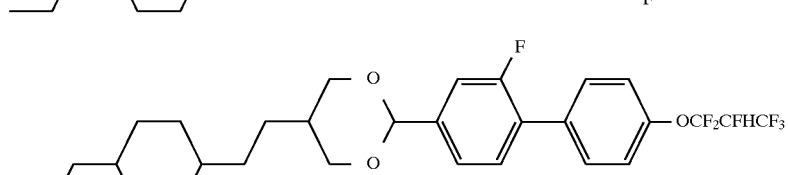 No. 265
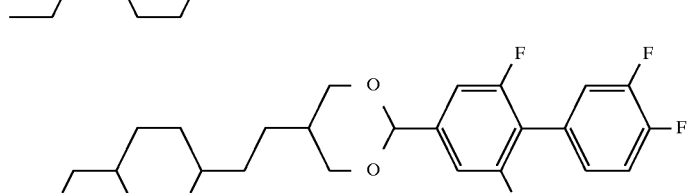 No. 266
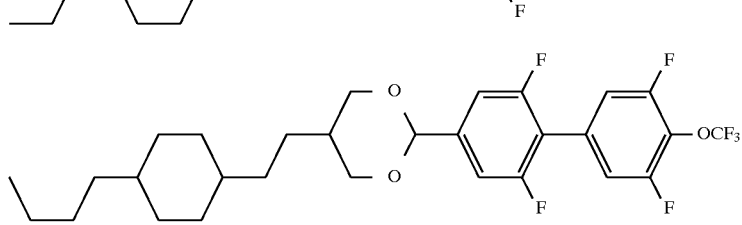 No. 267

-continued
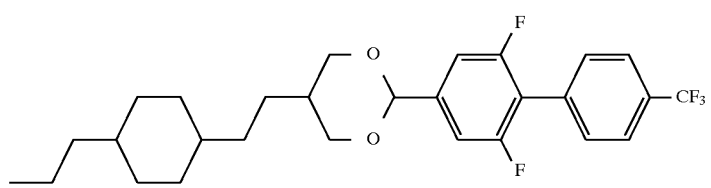 No. 268
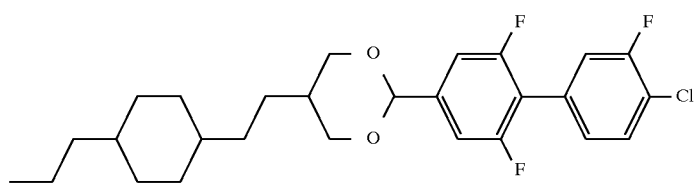 No. 269
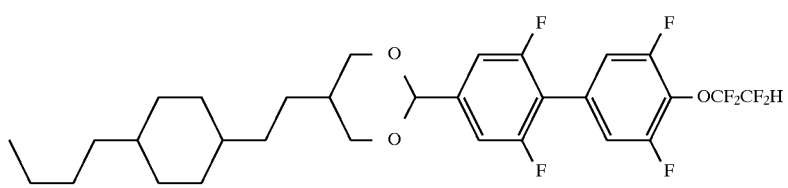 No. 270
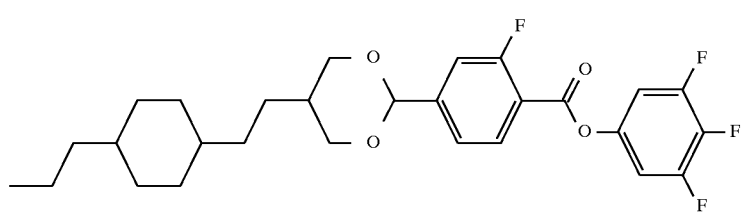 No. 271
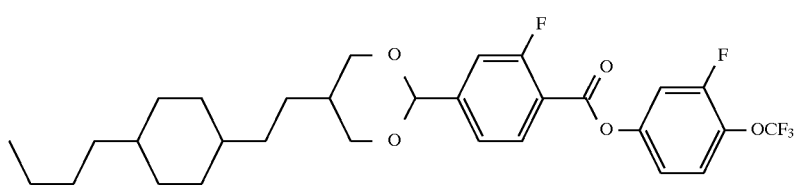 No. 272
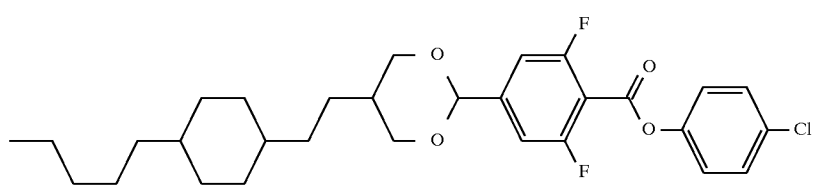 No. 273
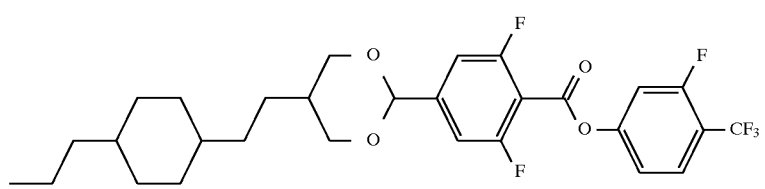 No. 274
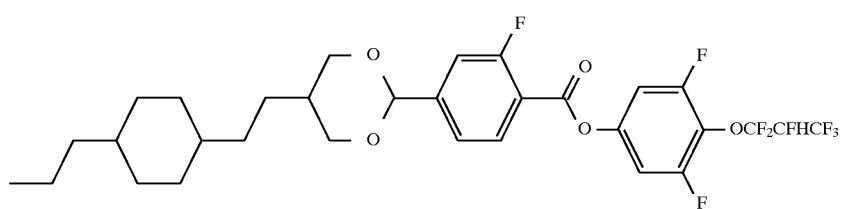 No. 275

-continued
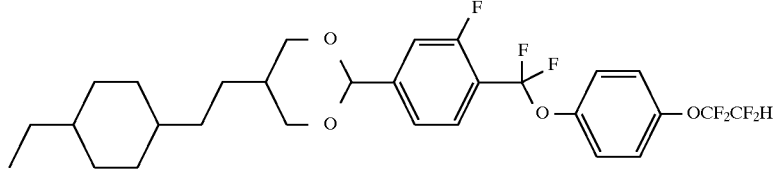
No. 276
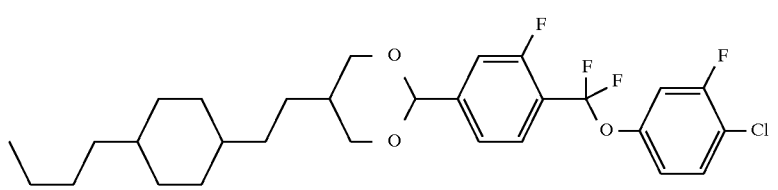
No. 277
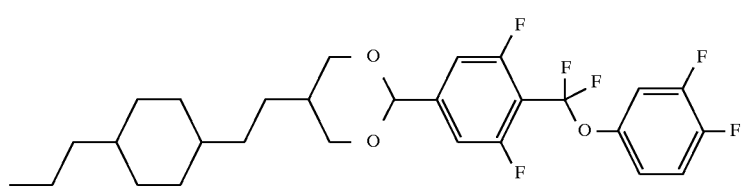
No. 278
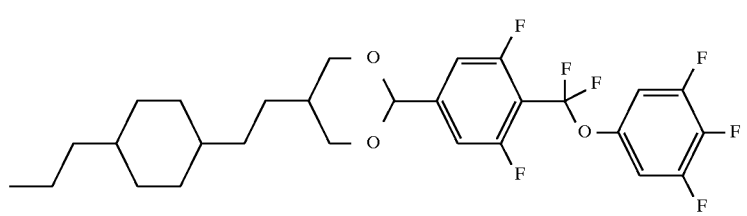
No. 279
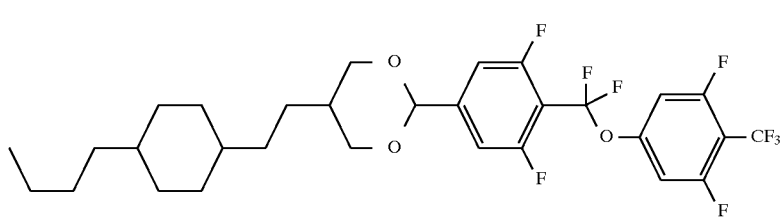
No. 280
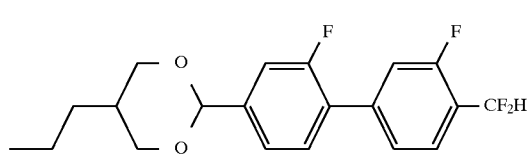
No. 281
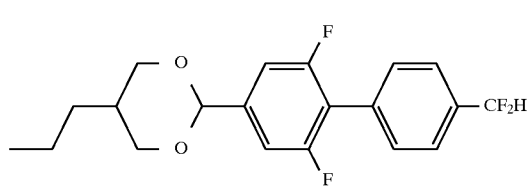
No. 282
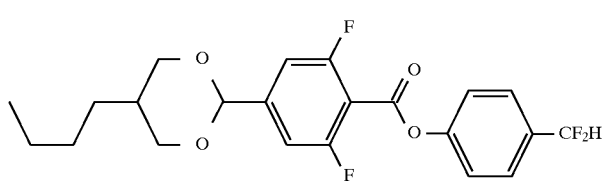
No. 283
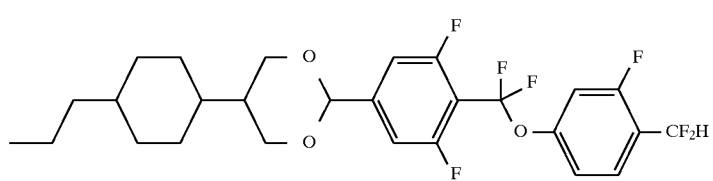
No. 284

-continued
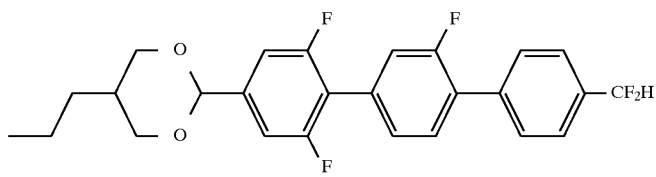
No. 285
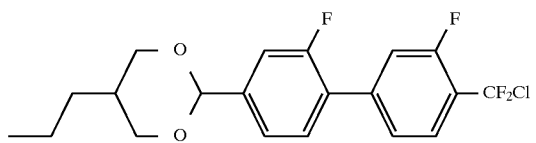
No. 286
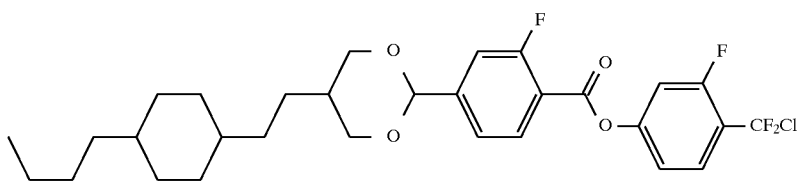
No. 287
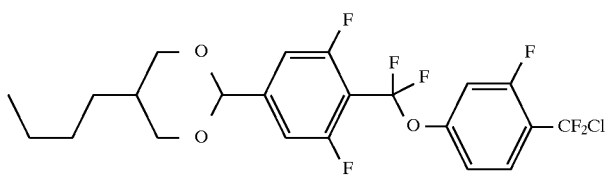
No. 288
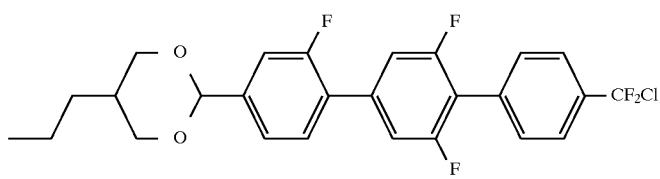
No. 289
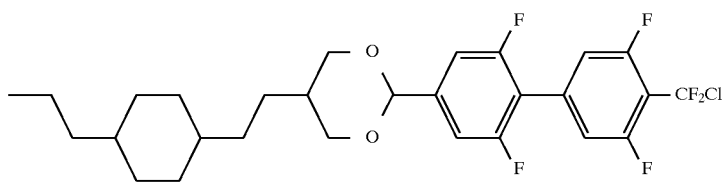
No. 290
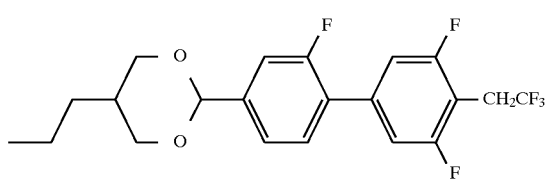
No. 291
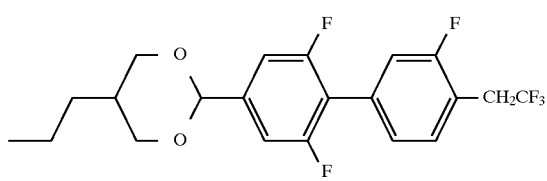
No. 292
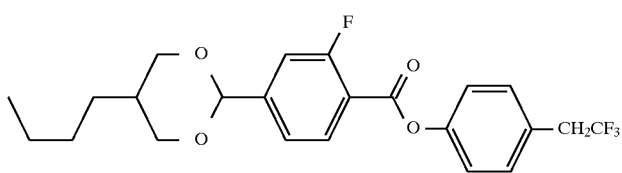
No. 293

-continued
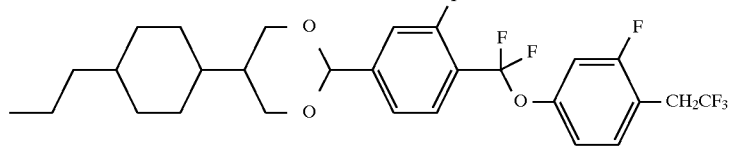 No. 294
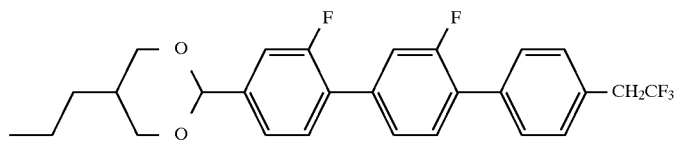 No. 295
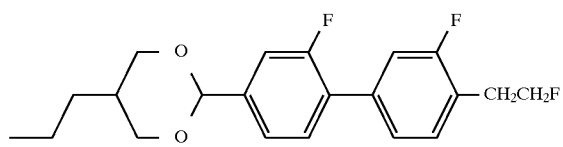 No. 296
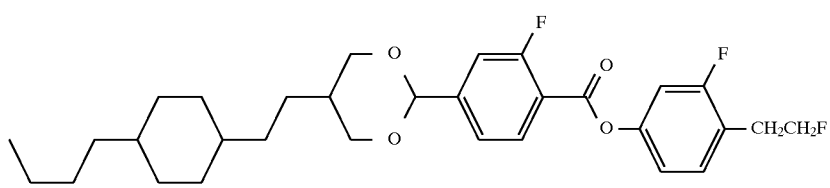 No. 297
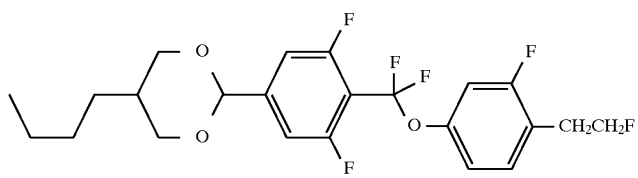 No. 298
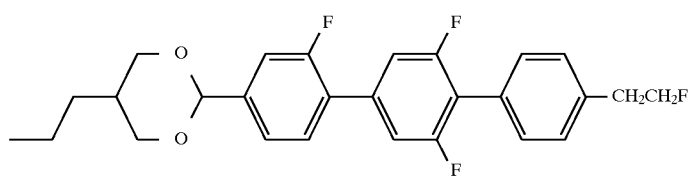 No. 299
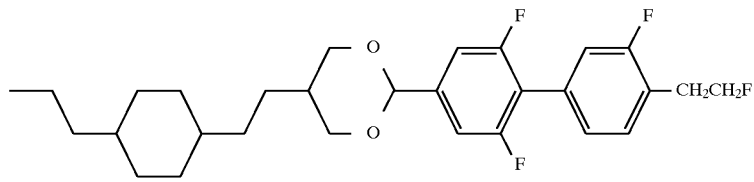 No. 300
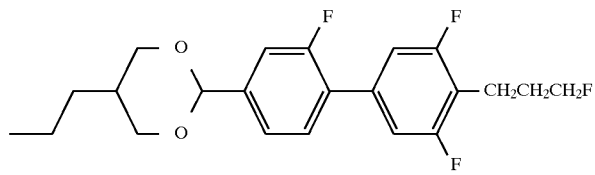 No. 301
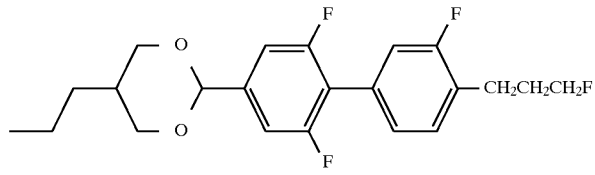 No. 302

-continued
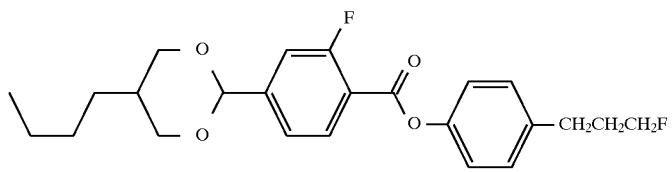 No. 303
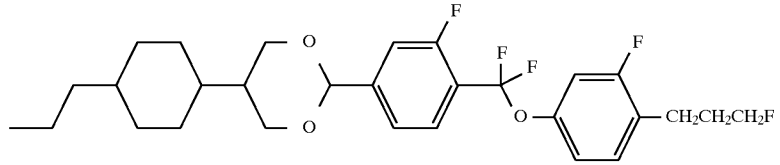 No. 304
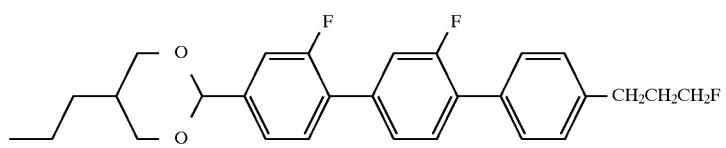 No. 305
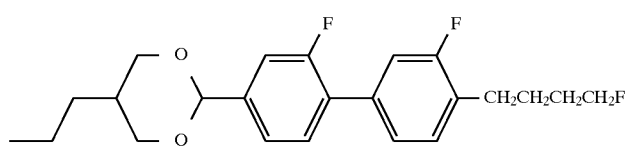 No. 306
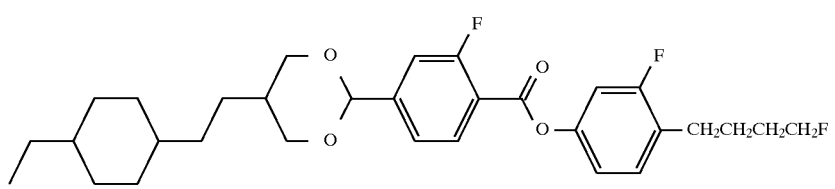 No. 307
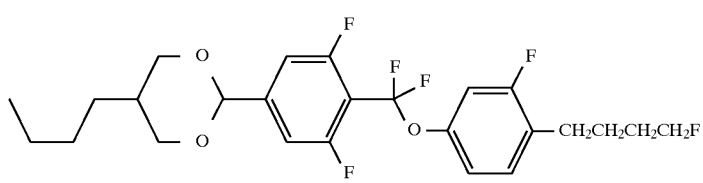 No. 308
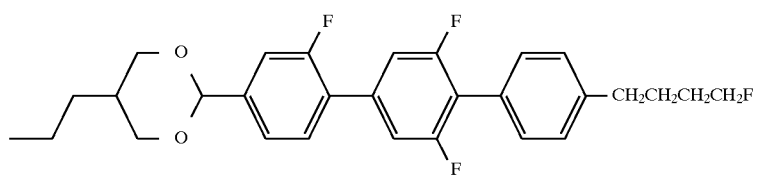 No. 309
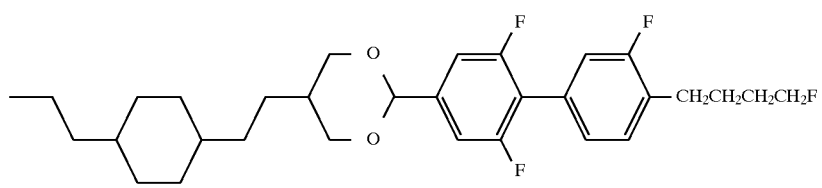 No. 310
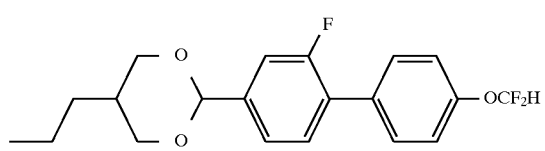 No. 311

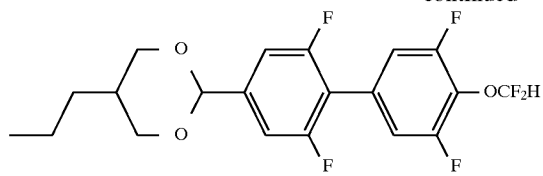
No. 312
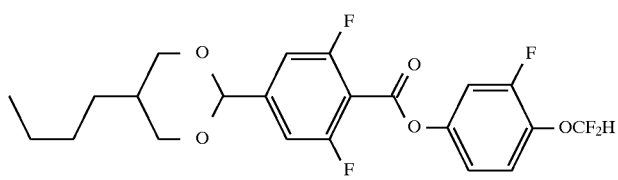
No. 313
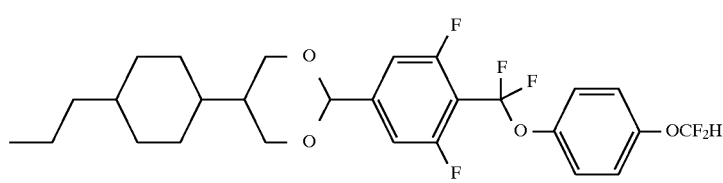
No. 314
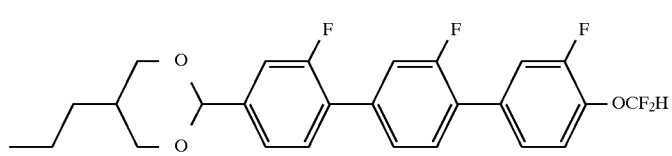
No. 315
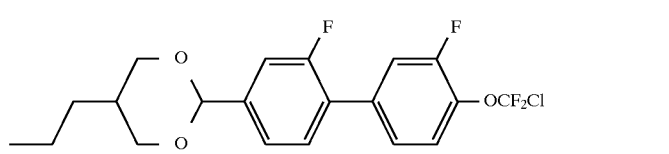
No. 316
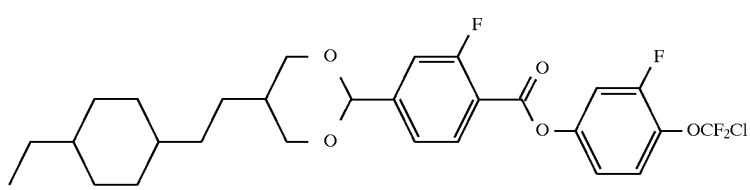
No. 317
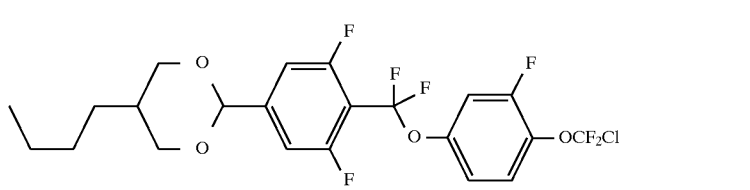
No. 318
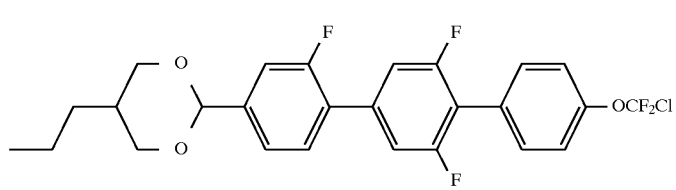
No. 319
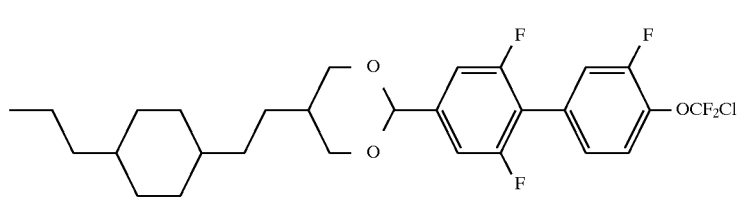
No. 320

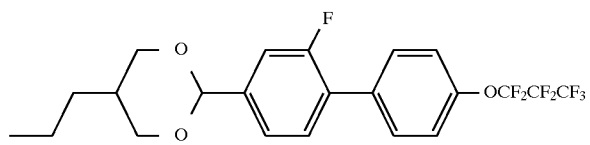
No. 321
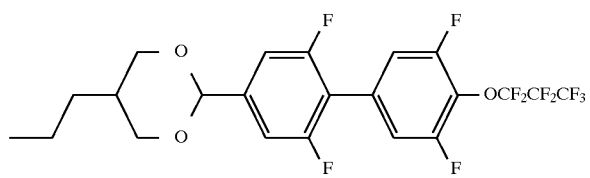
No. 322
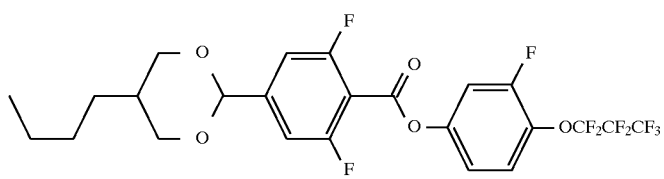
No. 323
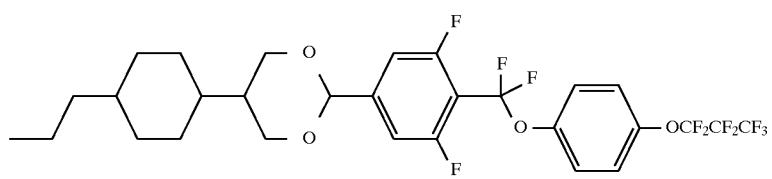
No. 324
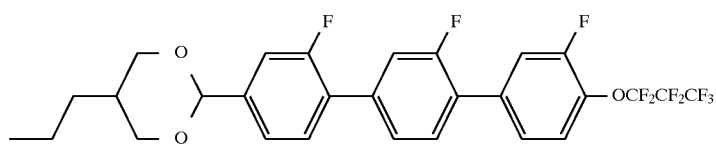
No. 325
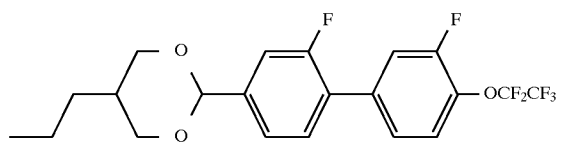
No. 326
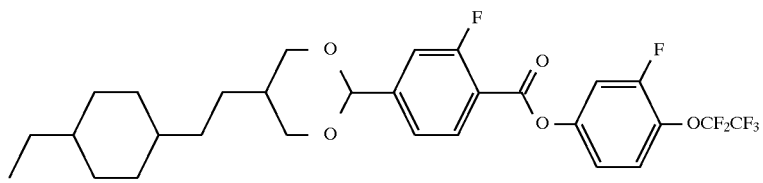
No. 327
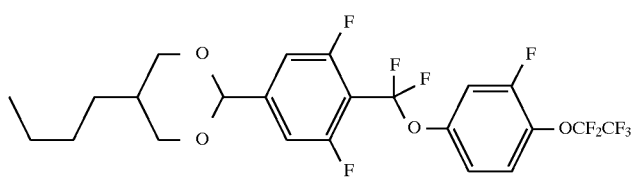
No. 328
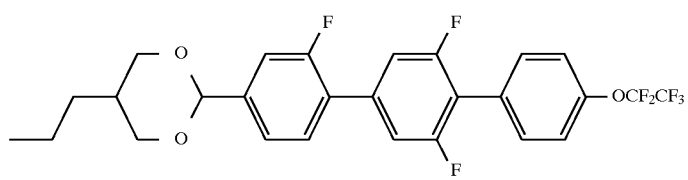
No. 329

-continued
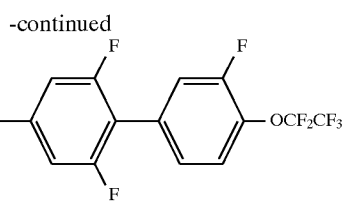
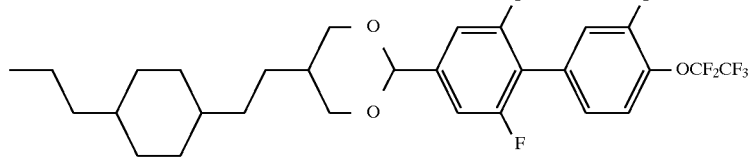
No. 330
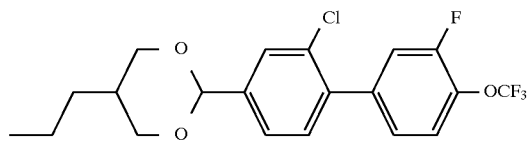
No. 331
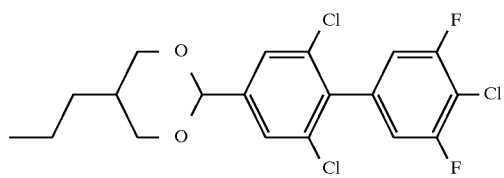
No. 332
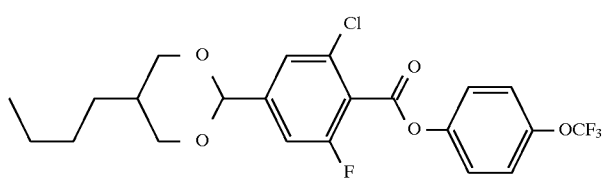
No. 333
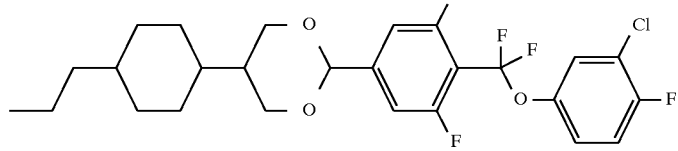
No. 334
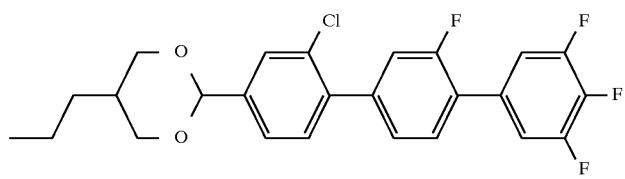
No. 335
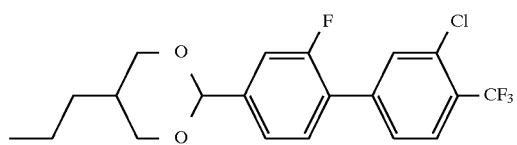
No. 336
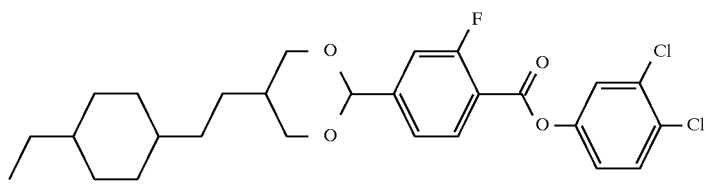
No. 337
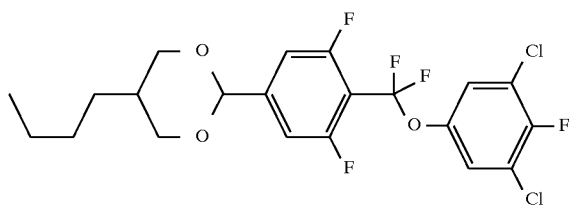
No. 338

-continued
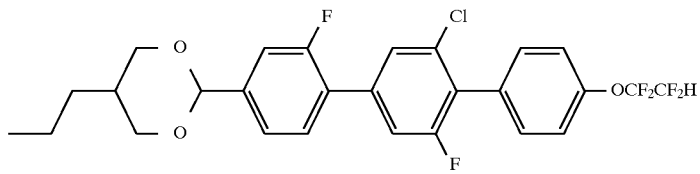 No. 339
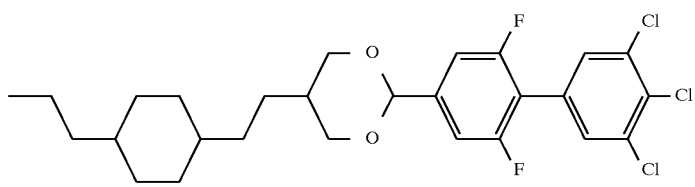 No. 340
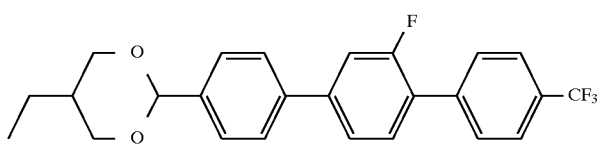 No. 341
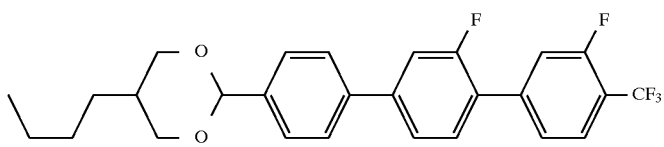 No. 342
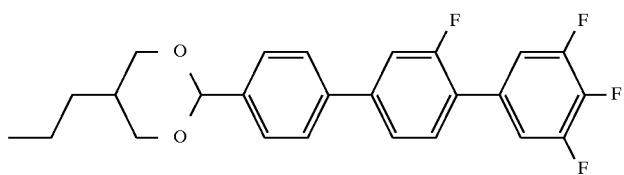 No. 343
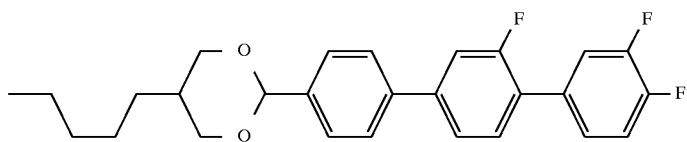 No. 344
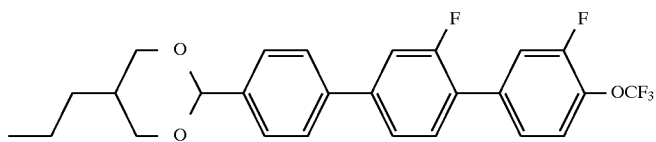 No. 345
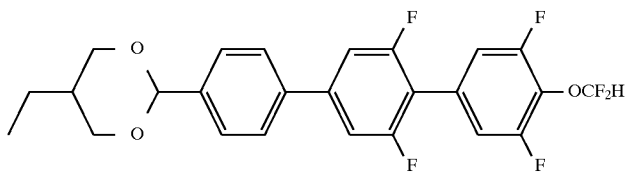 No. 346
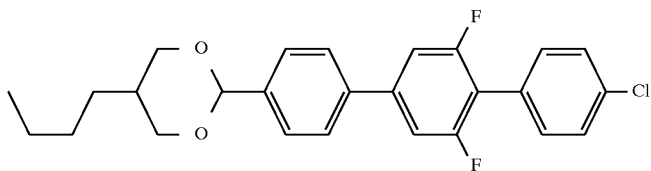 No. 347

-continued

No. 348

No. 349

No. 350

Example 10
(Application Example 1)

A nematic liquid crystal composition containing a cyanophenylcyclohexane-type liquid crystal compound (hereinafter may be referred to as liquid crystal composition A1):

| | |
|---|---|
| 4-(4-Propylcyclohexyl)benzonitrile | 24% |
| 4-(4-Pentylcyclohexyl)benzonitrile | 36% |
| 4-(4-Heptylcyclohexyl)benzonitrile | 25% |
| 4-(4-(4-Pentylcyclohexyl)phenylbenzonitrile | 15% |

The liquid crystal composition A1 has the following properties.

Clearing point ($T_{NI}$): 71.7° C.; threshold voltage ($V_{th}$) for a cell thickness of 8.8 μm: 1.78 V; $\Delta\epsilon 1$: 11.0; $\Delta n1$: 0.137; viscosity (η) at 20° C.: 26.3 mPa.s.

The liquid crystal composition A1 (85% by weight) and 5-propyl-2-(4-(3,4-difluorophenyl)-3,5-difluorophenyl)-1,3-dioxane obtained in Example 1 (Compound No. 23; 15% by weight) were mixed to thereby prepare liquid crystal composition B1. The liquid crystal composition B1 maintained the nematic phase even after being allowed to stand for 30 days at −20° C., and was found to have the following properties.

Clearing point ($T_{NI}$): 63.5° C.; threshold voltage ($V_{th}$) for a cell thickness of 9.2 μm: 1.40 V; $\Delta\epsilon 1$: 12.8; $\Delta n1$: 0.132; viscosity (η) at 20° C.: 33.2 mPa.s.

From properties of liquid crystal compositions A1 and B1 and the proportions of their components, properties of Compound No. 23 were calculated by extrapolation and found to be as follows:

Clearing point ($T_{NI}$): 17.0° C.; $\Delta\epsilon$: 23.0; $\Delta n$: 0.104; viscosity (η) at 20° C.: 72.6 mPa.s.

Example 11
(Application Example 2)

Liquid crystal composition B2 was prepared in a manner similar to that of Example 10 except that 5-propyl-2-(4-(4-fluorophenyl)-3,5-difluorophenyl)-1,3-dioxane (Compound No. 22) obtained in Example 3 was used in place of Compound No. 23. The liquid crystal composition B2 maintained the nematic phase even after being allowed to stand for 30 days at −20° C., and was found to have the following properties.

Clearing point ($T_{NI}$): 67.0° C.; threshold voltage ($V_{th}$) for a cell thickness of 9.1 μm: 1.49 V; $\Delta\epsilon 1$: 11.9; $\Delta n1$: 0.133; viscosity (η) at 20° C.: 30.2 mPa.s.

From properties of liquid crystal compositions A1 and B2 and the proportions of their components, properties of Compound No. 22 were calculated by extrapolation and found to be as follows:

Clearing point ($T_{NI}$): 40.4° C.; $\Delta\epsilon$: 17.0; $\Delta n$: 0.110; viscosity (η) at 20° C.: 52.3 mPa.s.

Example 12
(Application Example 3)

Liquid crystal composition B3 was prepared in a manner similar to that of Example 10 except that 5-propyl-2-(4-(3-fluoro-4-trifluoromethoxyphenyl)-3,5-difluorophenyl)-1,3-dioxane (Compound No. 26) obtained in Example 4 was used in place of Compound No. 23. The liquid crystal composition B3 maintained the nematic phase even after being allowed to stand for 30 days at −20° C., and was found to have the following properties.

Clearing point ($T_{NI}$): 65.1° C.; threshold voltage ($V_{th}$) for a cell thickness of 9.1 μm: 1.40 V; $\Delta\epsilon 1$: 13.2; $\Delta n1$: 0.133; viscosity (η) at 20° C.: 30.8 mPa.s.

From properties of liquid crystal compositions A1 and B3 and the proportions of their components, properties of Compound No. 26 were calculated by extrapolation and found to be as follows:

Clearing point ($T_{NI}$): 27.7° C.; $\Delta\epsilon$: 25.7; $\Delta n$: 0.110; viscosity (η) at 20° C.: 56.3 mPa.s.

Example 13
(Application Example 4)

Liquid crystal composition B4 was prepared in a manner similar to that of Example 10 except that 5-propyl-2-(4-(3,5-difluoro-4-trifluoromethylphenyl)-3,5-difluorophenyl)-1,3-dioxane (Compound No. 30) obtained in Example 5 was used in place of Compound No. 23 and that liquid crystal composition A1 (95% by weight) and Composition No. 30 (5% by weight) were mixed. The liquid crystal composition B4 maintained the nematic phase even after being allowed to stand for 30 days at −20° C., and was found to have the following properties.

Clearing point ($T_{NI}$): 68.0° C.; threshold voltage ($V_{th}$) for a cell thickness of 9.1 μm: 1.52 V; Δε1: 12.6; Δn1: 0.136; viscosity (η) at 20° C.: 28.2 mPa.s.

From properties of liquid crystal compositions A1 and B4 and the proportions of their components, properties of Compound No. 30 were calculated by extrapolation and found to be as follows:

Clearing point ($T_{NI}$): _2.3° C.; Δε: 43.0; Δn: 0.117; viscosity (η) at 20° C.: 64.3 mPa.s.

Example 14
(Application Example 5)

Liquid crystal composition B5 was prepared in a manner similar to that of Example 10 except that 5-propyl-2-(4-(4-chlorophenyl)-3,5-difluorophenyl)-1,3-dioxane (Compound No. 32) obtained in Example 6 was used in place of Compound No. 23. The liquid crystal composition B5 maintained the nematic phase even after being allowed to stand for 30 days at −20° C., and was found to have the following properties.

Clearing point ($T_{NI}$): 70.9° C.; threshold voltage ($V_{th}$) for a cell thickness of 9.0 μm: 1.57 V; Δε1: 12.3; Δn1: 0.140; viscosity (η) at 20° C.: 33.3 mPa.s.

From properties of liquid crystal compositions A1 and B5 and the proportions of their components, properties of Compound No. 32 were calculated by extrapolation and found to be as follows:

Clearing point ($T_{NI}$): 66.4° C.; Δε: 19.7; Δn: 0.157; viscosity (η) at 20° C.: 72.4 mPa.s.

Example 15
(Application Example 6)

Liquid crystal composition B6 was prepared in a manner similar to that of Example 10 except that 3,4-difluorophenyl-4-(5-propyl-(1,3-dioxane)-2-yl)-2,6-difluorophenylcarboxylate (Compound No. 63) obtained in Example 7 was used in place of Compound No. 23. The liquid crystal composition B6 maintained the nematic phase even after being allowed to stand for 30 days at −20° C., and was found to have the following properties.

Clearing point ($T_{NI}$): 66.8° C.; threshold voltage ($V_{th}$) for a cell thickness of 9.1 μm: 1.38 V; Δε1: 13.6; Δn1: 0.130; viscosity (η) at 20° C.: 31.4 mPa.s.

From properties of liquid crystal compositions A1 and B6 and the proportions of their components, properties of Compound No. 63 were calculated by extrapolation and found to be as follows:

Clearing point ($T_{NI}$): 39.0° C.; Δε: 28.3; Δn: 0.090; viscosity (η) at 20° C.: 61.4 mPa.s.

Example 16
(Application Example 7)

Liquid crystal composition B7 was prepared in a manner similar to that of Example 13 except that 5-propyl-2-(4-(4-(3,4,5-trifluorophenyl)phenyl)-3,5-difluorophenyl)-1,3-dioxane (Compound No. 143) obtained in Example 8 was used in place of Compound No. 30. The liquid crystal composition B7 was found to have the following properties.

Clearing point ($T_{NI}$): 73.6° C.; threshold voltage ($V_{th}$) for a cell thickness of 9.3 μm: 1.78 V; Δε1: 11.9; Δn1: 0.139; viscosity (η) at 20° C.: 30.2 mPa.s.

From properties of liquid, crystal compositions A1 and B7 and the proportions of their components, properties of Compound No. 143 were calculated by extrapolation and found to be as follows:

Clearing point ($T_{NI}$): 109.7° C.; Δε: 29.0; Δn: 0.177; viscosity (η) at 20° C.: 96.7 mPa.s.

Example 17
(Application Example 8)

Liquid crystal composition B8 was prepared in a manner similar to that of Example 10 except that 5-propyl-2-(4-(3-fluoro-4-trifluoromethylphenyl)-3,5-difluorophenyl)-1,3-dioxane (Compound No. 29) obtained in Example 9 was used in place of Compound No. 23. The liquid crystal composition B8 was found to have the following properties.

Clearing point ($T_{NI}$): 61.3° C.; threshold voltage ($V_{th}$) for a cell thickness of 9.0 μm: 1.44 V; Δε1: 13.7; Δn1: 0.131; viscosity (η) at 20° C.: 35.6 mPa.s.

From properties of liquid crystal compositions A1 and B8 and the proportions of their components, properties of Compound No. 29 were calculated by extrapolation and found to be as follows:

Clearing point ($T_{NI}$): 2.4° C.; Δε: 29.0; Δn: 0.097; viscosity (η) at 20° C.: 86.6 mPa.s.

Example 18

There was prepared a liquid crystal composition (A2) containing:

| | |
|---|---|
| 4-(2-(4-ethylcyclohexyl)ethyl)cyclohexyl-3,4-difluorobenzene | 40% |
| 4-(2-(4-propylcyclohexyl)ethyl)cyclohexyl-3,4-difluorobenzene | 20% |
| 4-(2-(4-pentylcyclohexyl)ethyl)cyclohexyl-3,4-difluorobenzene | 40% |

The liquid crystal composition A2 (80% by weight) and 5-propyl-2-(4-(3,4-difluorophenyl)-3,5-difluorophenyl)-1,3-dioxane (Compound No. 23; 20% by weight) were mixed to thereby prepare liquid crystal composition B9. The liquid crystal composition B9 was found to have a voltage holding ratio of 98% at 25° C. and 93% at 100° C.

Example 19

Liquid crystal composition B10 was prepared in a manner similar to that of Example 18 except that 5-propyl-2-(4-(3-fluoro-4-trifluoromethoxyphenyl)-3,5-difluorophenyl)-1,3-dioxane (Compound No. 26) was used in place of Compound No. 23. The liquid crystal composition B10 was found to have a voltage holding ratio of 98% at 25° C. and 92% at 100° C.

Example 20
(Comparative Example 1)

Liquid crystal composition C1 was prepared in a manner similar to that of Example 18 except that 5-propyl-2-(4-(3,4,5-trifluorophenyl)phenyl)-1,3-dioxane (a comparative compound) represented by TFT-mode aforementioned Formula (15) was used in place of Compound No. 23.

The liquid crystal composition C1 was found to have a voltage holding ratio of 97% at 25° C. and 89% at 100° C., indicating that liquid crystal composition C1 is inferior to the liquid crystal compositions of Examples 18 and 19 in a voltage holding ratio at high temperatures.

As described above, the liquid crystalline compounds of the present invention exhibit significantly large values of De and high voltage holding ratios, and are electrically and chemically stable. Moreover, they exhibit excellent compatibility with previously known liquid crystalline compounds.

Therefore, when the liquid crystalline compounds of the present invention are used as components of a liquid crystal composition, it is possible to attain low voltage driving of liquid crystal display elements, inter alia liquid crystal display elements for TFTs.

What is claimed is:

1. A phenyldioxane derivative expressed by the following formula (1):

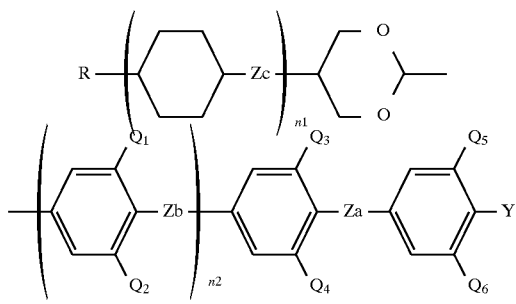

wherein R represents a C1–C 20 alkyl group; each of n1 and n2 represents 0 or 1; each of $Q_1$ through $Q_6$ represents a hydrogen atom, a fluorine atom, or a chlorine atom, provided that $Q_3$ is a fluorine atom or a chlorine atom when n2 is 0, and that at least one of $Q_1$ and $Q_3$ is a fluorine atom or a chlorine atom when n2 is 1; each of Za and Zb represents a single bond, —COO—, or —CF$_2$O—; Zc represents a single bond or —CH$_2$CH$_2$—; Y represents a hydrogen atom, a halogen atom, or a C1–C5 halogenated alkyl group in which one or more non-adjacent methylene groups may be replaced by oxygen atoms or sulfur atoms; and each of the elements that constitute the compound may comprise isotopes of the element.

2. The phenyldioxane derivative according to claim 1, in which n1 and n2 are both 0.

3. The phenyldioxane derivative according to claim 1, in which n1 is 0 and n2 is 1.

4. The phenyldioxane derivative according to claim 1, in which n1 is 1 and n2 is 0.

5. The phenyldioxane derivative according to claim 2, in which $Q_3$ and $Q_4$ are both fluorine atoms.

6. The phenyldioxane derivative according to claim 2, in which $Q_3$ is a fluorine atom and $Q_4$ is a hydrogen atom.

7. A liquid crystal composition comprising at least one species of the phenyldioxane derivative as described in one of claims 1 to 6.

8. A liquid crystal composition comprising a first component and a second component, the first component being at least one species of the phenyldioxane derivative as described in one of claims 1 to 6, and the second component being at least one compound selected from the group consisting of formula (2) compounds, formula (3) compounds, and formula (4) compounds:

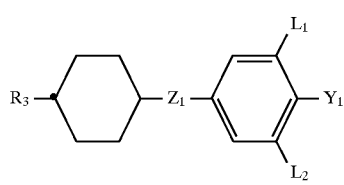

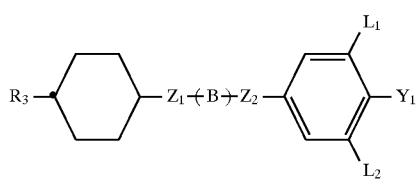

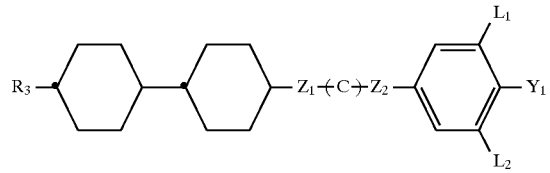

wherein $R_3$'s, $Y_1$'s, $L_1$'s, $L_2$'s, $Z_1$'s, and $Z_2$'s appearing in these formulas may respectively represent the same atom/group or different atoms/groups, $R_3$ represents a C1–C10 alkyl group in which one or more non-adjacent methylene groups may be replaced by oxygen atoms or —CH=CH— groups and hydrogen atoms may arbitrarily be substituted by fluorine atoms; $Y_1$ represents a fluorine atom, a chlorine atom, OCF$_3$, OCF$_2$H, CF$_3$, CF$_2$H, CFH$_2$, OCF$_2$CF$_2$H, or OCF$_2$CFHCF$_3$; each of $L_1$ and $L_2$ represents a hydrogen atom or a fluorine atom; each of $Z_1$ and $Z_2$ represents a 1,2-ethylene group, a 1,4-butylene group, —COO—, —CF$_2$O—, —OCF$_2$—, —CH=CH—, or a single bond; ring B represents trans-1,4-cyclohexylene, 1,3-dioxane-2,5-diyl, or 1,4-phenylene in which a hydrogen atom may be substituted by a fluorine atom; ring C represents trans-1,4-cyclohexylene or 1,4-phenylene in which a hydrogen atom may be substituted by a fluorine atom; and each of the elements that constitute the respective compounds of formulas (2), (3), and (4) may comprise isotopes of the element.

9. A liquid crystal composition comprising a first component and a second component, the first component being at least one species of the phenyldioxane derivative as described in one of claims 1 to 6, and the second component being at least one compound selected from the group consisting of formula (5) compounds and formula (6) compounds:

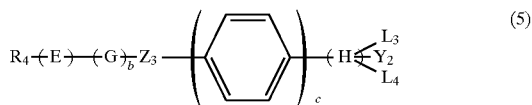

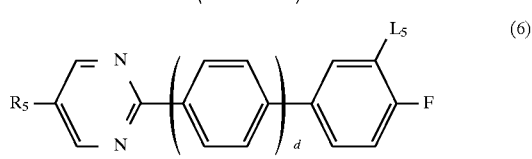

wherein each of $R_4$ and $R_5$ represents a C1–C10 alkyl group in which one or more non-adjacent methylene groups may be replaced by oxygen atoms or —CH=CH— groups, and hydrogen atoms may arbitrarily be substituted by fluorine atoms; $Y_2$ represents —CN or —C≡C—CN; ring E represents trans-1,4-cyclohexylene, 1,4-phenylene, 1,3-dioxane-2,5-diyl, or pyrimidine-2,5-diyl; ring G represents trans-1,4-cyclohexylene, 1,4-phenylene in which hydrogen atoms may be substituted by fluorine atoms, or pyrimidine-2,5-diyl; ring H represents trans-1,4-cyclohexylene or 1,4-phenylene; $Z_3$ represents a 1,2-ethylene group, —COO—, or a single bond; each of $L_3$, $L_4$, and $L_5$ represents a hydrogen atom or a fluorine atom; each of b, c, and d represents 0 or 1; and each of the elements that constitute the respective compounds of formulas (5) and (6) may comprise isotopes of the element.

10. A liquid crystal composition comprising a first component, a second component, and a third component, the first component being at least one species of the phenyldioxane derivative as described in one of claims 1 to 6, the second component being at least one compound selected from the group consisting of formula (2) compounds, formula (3) compounds, and formula (4) compounds:

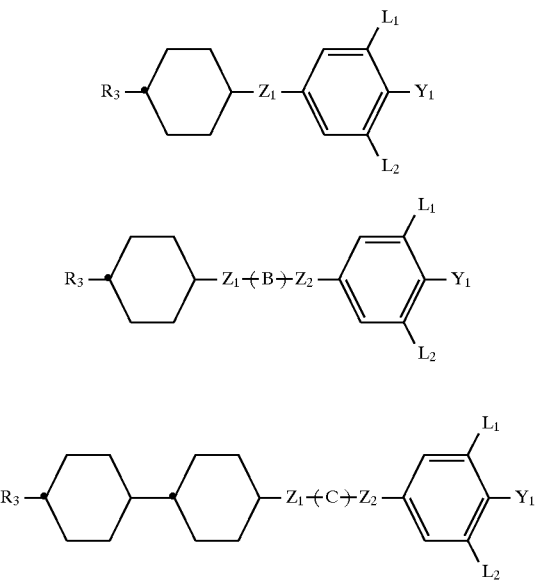

wherein $R_3$'s, $Y_1$'s, $L_1$'s, $L_2$'s, $Z_1$'s, and $Z_2$'s appearing in these formulas may respectively represent the same atom/group or different atoms/groups, $R_3$ represents a C1–C10 alkyl group in which one or more non-adjacent methylene groups may be replaced by oxygen atoms or —CH=CH— groups and hydrogen atoms may arbitrarily be substituted by fluorine atoms; $Y_1$ represents a fluorine atom, a chlorine atom, $OCF_3$, $OCF_2H$, $CF_3$, $CF_2H$, $CFH_2$, $OCF_2CF_2H$, or $OCF_2CFHCF_3$; each of $L_1$ and $L_2$ represents a hydrogen atom or a fluorine atom; each of $Z_1$ and $Z_2$ represents a 1,2-ethylene group, a 1,4-butylene group, —COO—, —$CF_2O$—, —$OCF_2$—, —CH=CH—, or a single bond; ring B represents trans-1,4-cyclohexylene, 1,3-dioxane-2,5-diyl, or 1,4-phenylene in which a hydrogen atom may be substituted by a fluorine atom; ring C represents trans-1,4-cyclohexylene or 1,4-phenylene in which a hydrogen atom may be substituted by a fluorine atom; and each of the elements that constitute the respective compounds of formulas (2), (3), and (4) may comprise isotopes of the element, and the third component being at least one compound selected from the group consisting of formula (7) compounds, formula (8) compounds, and formula (9) compounds:

 (7)

 (8)

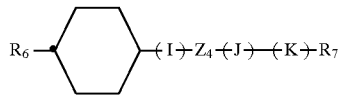 (9)

wherein $R_6$'s, $R_7$'s, I's, J's, and K's appearing in these formulas may respectively represent the same atom/group or different atoms/groups, each of $R_6$ and $R_7$ represents a C1–C10 alkyl group in which one or more non-adjacent methylene groups may be replaced by oxygen atoms or —CH=CH— groups and hydrogen atoms may arbitrarily be substituted by fluorine atoms; each of I, J, and K represents trans-1,4-cyclohexylene, pyrimidine-2,5-diyl, or 1,4-phenylene in which a hydrogen atom may be substituted by a fluorine atom; each of $Z_4$ and $Z_5$ represents —C≡C—, —COO—, —$CH_2CH_2$—, —CH=CH—, or a single bond; and each of the elements that constitute the respective compounds of formulas (7), (8), and (9) may comprise isotopes of the element.

11. A liquid crystal composition comprising a first component, a second component, and a third component,
the first component being at least one species of the phenyldioxane derivative as described in one of claims 1 to 6,
the second component being at least one compound selected from the group consisting of formula (5) compounds and formula (6) compounds:

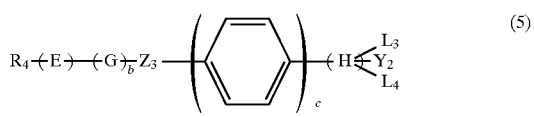

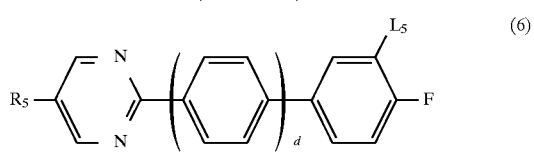

wherein each of $R_4$ and $R_5$ represents a C1–C10 alkyl group in which one or more non-adjacent methylene groups may be replaced by oxygen atoms or —CH=CH— groups, and hydrogen atoms may arbitrarily be substituted by fluorine atoms; $Y_2$ represents —CN or —C≡C—CN; ring E represents trans-1,4-cyclohexylene, 1,4-phenylene, 1,3-dioxane-2,5-diyl, or pyrimidine-2,5-diyl; ring G represents trans-1,4-cyclohexylene, 1,4-phenylene in which hydrogen atoms may be substituted by fluorine atoms, or pyrimidine-2,5-diyl; ring H represents trans-1,4-cyclohexylene or 1,4-phenylene; $Z_3$ represents a 1,2-ethylene group, —COO—, or a single bond; each of $L_3$, $L_4$, and $L_5$ represents a hydrogen atom or a fluorine atom; each of b, c, and d represents 0 or 1; and each of the elements that constitute the respective compounds of formulas (5) and (6) may comprise isotopes of the element, and
the third component being at least one compound selected from the group consisting of formula (7) compounds, formula (8) compounds, and formula (9) compounds:

 (7)

 (7)

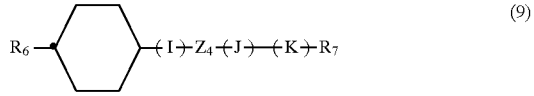 (9)

wherein $R_6$'s, $R_7$'s, I's, J's, and K's appearing in these formulas may respectively represent the same atom/group or different atoms/groups, each of $R_6$ and $R_7$ represents a C1–C10 alkyl group in which one or more non-adjacent methylene groups may be replaced by oxygen atoms or —CH=CH— groups and hydrogen atoms may arbitrarily be substituted by fluorine atoms; each of I, J, and K represents trans-1,4-cyclohexylene, pyrimidine-2,5-diyl, or 1,4-phenylene in which a hydrogen atom may be substituted by a fluorine atom; each of $Z_4$ and $Z_5$ represents —C≡C—, COO—, —$CH_2CH_2$—, —CH=CH—, or a single bond; and each of the elements that constitute the respective compounds of formulas (7), (8), and (9) may comprise isotopes of the element.

12. A liquid crystal composition comprising first, second, and third components, the first component being at least one species of phenyl-dioxane derivative as described in one of claims 1 to 6, part of the second component being at least one compound selected from the group consisting of the following formula (2) compounds, formula (3) compounds, and formula (4) compounds:

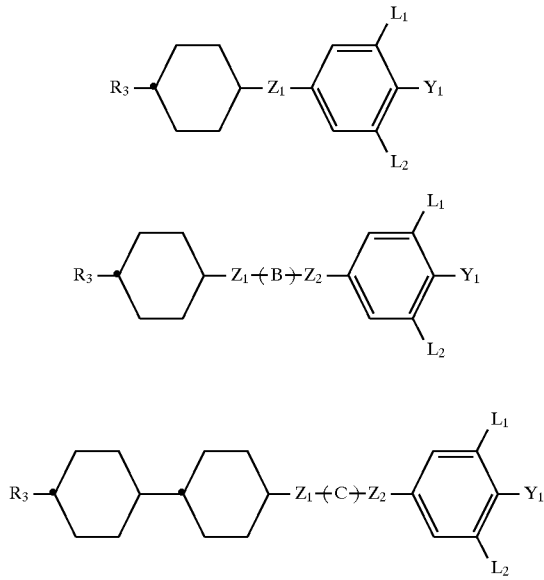

wherein $R_3$'s, $Y_1$'s, $L_1$'s, $L_2$'s, $Z_1$'s, and $Z_2$'s appearing in these formulas may respectively represent the same atom/group or different atoms/groups, $R_3$ represents a C1–C 10 alkyl group in which one or more non-adjacent methylene groups may be replaced by oxygen atoms or —CH=CH— groups and hydrogen atoms may arbitrarily be substituted by fluorine atoms; $Y_1$ represents a fluorine atom, a chlorine atom, $OCF_3$, $OCF_2H$, $CF_3$, $CF_2H$, $CFH_2$, $OCF_2CF_2H$, or $OCF_2CFHCF_3$; each of $L_1$ and $L_2$ represents a hydrogen atom or a fluorine atom; each of $Z_1$ and $Z_2$ represents a 1,2-ethylene group, a 1,4-butylene group, —COO—, —CF$_2$O—, —OCF$_2$—, —CH=CH—, or a single bond; ring B represents trans-1,4-cyclohexylene, 1,3-dioxane-2,5-diyl, or 1,4-phenylene in which a hydrogen atom may be substituted by a fluorine atom; ring C represents trans-1,4-cyclohexylene or 1,4-phenylene in which a hydrogen atom may be substituted by a fluorine atom; and each of the elements that constitute the respective compounds of formulas (2), (3), and (4) may comprise isotopes of the element,
the remaining part of the second component being at least one compound selected from the group consisting of the following formula (5) and formula (6) compounds,

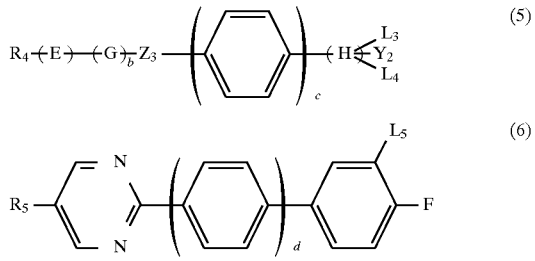

wherein each of $R_4$ and $R_5$ represents a C1–C10 alkyl group in which one or more non-adjacent methylene groups may be replaced by oxygen atoms or —CH=CH— groups, and hydrogen atoms may arbitrarily be substituted by fluorine atoms; $Y_2$ represents —CN or —C≡C—CN; ring E represents trans-1,4-cyclohexylene, 1,4-phenylene; 1,3-dioxane-2,5-diyl, or pyrimidine-2,5-diyl; ring G represents trans-1,4-cyclohexylene, 1,4-phenylene in which hydrogen atoms may be substituted by fluorine atoms, or pyrimidine-2,5-diyl; ring H represents trans-1,4-cyclohexylene or 1,4-phenylene; $Z_3$ represents a 1,2-ethylene group, —COO—, or a single bond; each of $L_3$, $L_4$, and $L_5$ represents a hydrogen atom or a fluorine atom; each of b, c, and d represents 0 or 1; and each of the elements that constitute the respective compounds of formulas (5) and (6) may comprise isotopes of the element, and the third component being at least one compound selected from the group consisting of formula (7) compounds, formula (8) compounds, and formula (9) compounds:

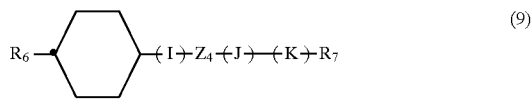

wherein $R_6$'s, $R_7$'s, I's, J's, and K's appearing in these formulas may respectively represent the same atom/group or different atoms/groups, each of $R_6$ and $R_7$ represents a C1–C10 alkyl group in which one or more non-adjacent methylene groups may be replaced by oxygen atoms or —CH=CH— groups and hydrogen atoms may arbitrarily be substituted by fluorine atoms; each of I, J, and K represents trans-1,4-cyclohexylene, pyrimidine-2,5-diyl, or 1,4-phenylene in which a hydrogen atom may be substituted by a fluorine atom; each of $Z_4$ and $Z_5$ represents —C≡C—, —COO—, —CH$_2$CH$_2$—, —CH=CH—, or a single bond; and each of the elements that constitute the respective compounds of formulas (7), (8), and (9) may comprise isotopes of the element.

13. The liquid crystal composition according to claim 7, further containing an optically active compound.
14. The liquid crystal composition according to claim 8, further containing an optically active compound.
15. The liquid crystal composition according to claim 9, further containing an optically active compound.
16. The liquid crystal composition according to claim 10, further containing an optically active compound.
17. The liquid crystal composition according to claim 11, further containing an optically active compound.
18. The liquid crystal composition according to claim 12, further containing an optically active compound.
19. A liquid crystal display element comprising the liquid crystal composition as described in claim 7.
20. A liquid crystal display element comprising the liquid crystal composition as described in claim 8.
21. A liquid crystal display element comprising the liquid crystal composition as described in claim 9.
22. A liquid crystal display element comprising the liquid crystal composition as described in claim 10.
23. A liquid crystal display element comprising the liquid crystal composition as described in claim 11.
24. A liquid crystal display element comprising the liquid crystal composition as described in claim 12.
25. A liquid crystal display element comprising the liquid crystal composition as described in claim 13.

26. A liquid crystal display element comprising the liquid crystal composition as described in claim 14.

27. A liquid crystal display element comprising the liquid crystal composition as described in claim 15.

28. A liquid crystal display element comprising the liquid crystal composition as described in claim 16.

29. A liquid crystal display element comprising the liquid crystal composition as described in claim 17.

30. A liquid crystal display element comprising the liquid crystal composition as described in claim 18.

* * * * *